(12) United States Patent
Thuering et al.

(10) Patent No.: US 11,896,352 B2
(45) Date of Patent: Feb. 13, 2024

(54) SYSTEM, DEVICE AND METHOD FOR SAFEGUARDING THE WELLBEING OF PATIENTS FOR FLUID INJECTION

(71) Applicant: BAYER HEALTHCARE LLC, Whippany, NJ (US)

(72) Inventors: Johannes Anton Thuering, Frechen (DE); Arthur Uber, III, Pittsburgh, PA (US); David Griffiths, Pittsburgh, PA (US); Michael McDermott, Berlin (DE); Charles Lang, Pittsburgh, PA (US); Linda Van Roosmalen, Gibsonia, PA (US); Barry Skirble, Allison Park, PA (US); Adam Czibur, Pittsburgh, PA (US); Daniel Moore, Pittsburgh, PA (US); Vincenzo Caruso, Ashbury (AU); Brandon Clarke, Boardman, OH (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 17/921,245

(22) PCT Filed: Apr. 30, 2021

(86) PCT No.: PCT/US2021/030210
§ 371 (c)(1),
(2) Date: Oct. 25, 2022

(87) PCT Pub. No.: WO2021/222771
PCT Pub. Date: Nov. 4, 2021

(65) Prior Publication Data
US 2023/0157552 A1 May 25, 2023

Related U.S. Application Data

(60) Provisional application No. 62/706,597, filed on Aug. 27, 2020, provisional application No. 62/705,613, (Continued)

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/4848* (2013.01); *A61B 5/7275* (2013.01);
(Continued)

(58) Field of Classification Search
CPC ... A61B 5/0205; A61B 5/4848; A61B 5/7275; A61B 5/28; A61B 5/296; A61M 5/007;
(Continued)

(56) References Cited

U.S. PATENT DOCUMENTS 383,858 A  6/1888 Campbell
3,156,236 A  11/1964 Williamson
(Continued)

FOREIGN PATENT DOCUMENTS

EP  1800704 A1  6/2007
EP  2692375 A1  2/2014
(Continued)

OTHER PUBLICATIONS

McCullough et al. 2006 Am. J. Cardiol. 98:suppl. 27K-36K (Year: 2006).*

(Continued)

*Primary Examiner* — Keith M Raymond
*Assistant Examiner* — Patrick M Mehl
(74) *Attorney, Agent, or Firm* — James R. Stevenson; Aaron Mace

(57) ABSTRACT

A system and method for promoting and safeguarding the wellbeing of patients in relation to a fluid injection may obtain patient data; determine, based on the patient data, an initial risk prediction for a patient for a fluid injection to be administered to the patient, the initial risk prediction including a probability that the patient experiences at least one adverse event in response to the fluid injection; provide, to a user device, before the fluid injection is administered to the patient, the initial risk prediction; determine, after the fluid injection is started, sensor data associated with the patient; determine, based on the sensor data determined after the fluid injection is started, a current risk prediction including a probability that the patient experiences the at least one adverse event in response to the fluid injection; and provide, to the user device, the current risk prediction.

21 Claims, 24 Drawing Sheets

Related U.S. Application Data filed on Jul. 7, 2020, provisional application No. 62/704,954, filed on Jun. 4, 2020, provisional application No. 63/017,942, filed on Apr. 30, 2020.

(51) Int. Cl.

| | | |
|---|---|---|
| A61M 5/00 | (2006.01) | |
| A61M 5/172 | (2006.01) | |
| A61B 5/296 | (2021.01) | |
| A61B 5/28 | (2021.01) | |
| G16H 50/30 | (2018.01) | |

(52) U.S. Cl.
CPC .......... *A61M 5/007* (2013.01); *A61M 5/1723* (2013.01); *A61B 5/28* (2021.01); *A61B 5/296* (2021.01); *A61M 2205/33* (2013.01); *G16H 50/30* (2018.01)

(58) Field of Classification Search
CPC A61M 5/1723; A61M 2205/33; G16H 50/30; G16H 20/17; G16H 50/20
See application file for complete search history.

(56) References Cited

U.S. PATENT DOCUMENTS

| | | |
|---|---|---|
| 4,610,665 A | 9/1986 | Matsumoto et al. |
| 5,026,348 A | 6/1991 | Venegas |
| 5,163,928 A | 11/1992 | Hobbs et al. |
| 5,334,141 A | 8/1994 | Carr et al. |
| 5,651,776 A | 7/1997 | Appling et al. |
| 5,954,668 A | 9/1999 | Uber, III et al. |
| 5,964,703 A | 10/1999 | Goodman et al. |
| 6,375,624 B1 | 4/2002 | Uber, III et al. |
| 6,408,204 B1 | 6/2002 | Hirschman |
| 6,459,931 B1 | 10/2002 | Hirschman |
| 6,643,537 B1 | 11/2003 | Zatezalo et al. |
| 6,751,500 B2 | 6/2004 | Hirschman |
| 7,047,058 B1 | 5/2006 | Dvorsky et al. |
| 7,122,012 B2 | 10/2006 | Bouton et al. |
| 7,553,294 B2 | 6/2009 | Lazzaro et al. |
| 7,563,249 B2 | 7/2009 | Schriver et al. |
| 7,591,792 B2 | 9/2009 | Bouton |
| 7,666,169 B2 | 2/2010 | Cowan et al. |
| 7,674,244 B2 | 3/2010 | Kalafut et al. |
| 7,937,134 B2 | 5/2011 | Uber et al. |
| 8,057,406 B2 | 11/2011 | Mohiuddin |
| 8,235,949 B2 | 8/2012 | Hack et al. |
| 8,295,920 B2 | 10/2012 | Bouton et al. |
| 8,403,909 B2 | 3/2013 | Spohn et al. |
| 8,439,863 B2 | 5/2013 | Fago et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,259,527 B2 | 2/2016 | Spohn et al. |
| 9,289,550 B1 | 3/2016 | Dvorsky et al. |
| 9,326,686 B2 | 5/2016 | Warren et al. |
| 9,333,293 B2 | 5/2016 | Williams, Jr. et al. |
| 9,474,857 B2 | 10/2016 | Riley et al. |
| 9,901,671 B2 | 2/2018 | Toews et al. |
| 10,124,110 B2 | 11/2018 | Dedig et al. |
| 10,398,353 B2 | 9/2019 | Addison et al. |
| 10,507,319 B2 | 12/2019 | Haury et al. |
| 10,583,256 B2 | 3/2020 | Berry et al. |
| 10,933,190 B2 | 3/2021 | Berry et al. |
| 11,141,535 B2 | 10/2021 | Uber, III et al. |
| 11,478,581 B2 | 10/2022 | McDermott et al. |
| 2002/0007116 A1 | 1/2002 | Zatezalo et al. |
| 2004/0171923 A1 | 9/2004 | Kalafut et al. |
| 2004/0253183 A1 | 12/2004 | Uber et al. |
| 2005/0107697 A1 | 5/2005 | Berke et al. |
| 2006/0079843 A1 | 4/2006 | Brooks et al. |
| 2006/0173360 A1 | 8/2006 | Kalafut et al. |
| 2006/0211970 A1 | 9/2006 | Sciulli |
| 2007/0219496 A1 | 9/2007 | Kamen et al. |
| 2007/0276327 A1 | 11/2007 | Kalafut et al. |
| 2008/0147147 A1 | 6/2008 | Griffiths et al. |
| 2009/0112164 A1 | 4/2009 | Reilly et al. |
| 2009/0216192 A1 | 8/2009 | Schriver et al. |
| 2009/0234226 A1 | 9/2009 | Nemoto |
| 2009/0247961 A1 | 10/2009 | Carlyon |
| 2010/0114064 A1* | 5/2010 | Kalafut ............ G16H 20/17 604/118 |
| 2010/0249586 A1 | 9/2010 | Cocker et al. |
| 2012/0089114 A1 | 4/2012 | Hemond et al. |
| 2012/0203177 A1 | 8/2012 | Lanier, Jr. et al. |
| 2012/0204997 A1 | 8/2012 | Winn et al. |
| 2013/0245604 A1 | 9/2013 | Kouyoumjian et al. |
| 2013/0261993 A1 | 10/2013 | Ruchti et al. |
| 2013/0274599 A1 | 10/2013 | Bouton et al. |
| 2014/0027009 A1 | 1/2014 | Riley et al. |
| 2014/0142537 A1 | 5/2014 | Gibson et al. |
| 2014/0276550 A1 | 9/2014 | Uram et al. |
| 2016/0224750 A1 | 8/2016 | Kethman et al. |
| 2016/0278725 A1 | 9/2016 | Van Nijnatten |
| 2016/0331896 A1 | 11/2016 | Nemoto et al. |
| 2016/0331951 A1 | 11/2016 | Sokolov et al. |
| 2017/0035974 A1 | 2/2017 | Berry et al. |
| 2017/0100534 A1 | 4/2017 | Fukikoshi et al. |
| 2017/0143898 A1 | 5/2017 | Grosse-Wentrup et al. |
| 2019/0083699 A1 | 3/2019 | Spohn et al. |
| 2020/0114074 A1 | 4/2020 | Barone et al. |
| 2020/0146647 A1 | 5/2020 | Uber, III et al. |
| 2020/0149948 A1 | 5/2020 | McDermott et al. |
| 2020/0179595 A1 | 6/2020 | McDermott et al. |
| 2020/0206414 A1 | 7/2020 | Marsh et al. |
| 2020/0246541 A1 | 8/2020 | Neftel et al. |
| 2020/0323546 A1 | 10/2020 | Skujins et al. |
| 2021/0146063 A1 | 5/2021 | McDermott et al. |
| 2021/0220556 A1 | 7/2021 | McDermott et al. |
| 2021/0220557 A1 | 7/2021 | Chaya |
| 2022/0392602 A1 | 12/2022 | McDermott |
| 2022/0395634 A1 | 12/2022 | McDermott |

FOREIGN PATENT DOCUMENTS

| | | |
|---|---|---|
| JP | 5485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| WO | 2006074415 A2 | 7/2006 |
| WO | 2009042577 A2 | 4/2009 |
| WO | 2009042577 A3 | 5/2009 |
| WO | 2012155035 A1 | 11/2012 |
| WO | 2016112163 A1 | 7/2016 |

(56) References Cited

FOREIGN PATENT DOCUMENTS

| | | |
|---|---|---|
| WO | 2017152036 A1 | 9/2017 |
| WO | 2018075386 A1 | 4/2018 |
| WO | 2019046299 A1 | 3/2019 |
| WO | 2020046869 A1 | 3/2020 |
| WO | 2021102242 A1 | 5/2021 |
| WO | 2021108286 A1 | 6/2021 |
| WO | 2021202359 A1 | 10/2021 |
| WO | 2021247595 A1 | 12/2021 |
| WO | 2021257699 A1 | 12/2021 |
| WO | 2022265695 A1 | 12/2022 |

OTHER PUBLICATIONS

European Society of Radiology 2019 Insights Into Imaging 10: article 45 with 17 pages (Year: 2019).*
Nouh et al. 2017 World J. Radiol. 28:339-349 (Year: 2017).*
Behzadi; et al., "MR and CT contrast media extravasation.", Medicine, 2018, 97, 9.
Brenner; et al, "Radiation Exposure From Medical Imaging: Time to Regulate?", JAMA, Jul. 14, 2010, vol. 304 No 2, 208-209.
"Extravasation Sensor Support System LD Operation Manual", Nemoto Kyorindo Co Ltd, Sep. 13, 2012, Rev 4.
"International Preliminary Report on Patentability from PCT Application No. PCT/US2021/030210", dated Nov. 10, 2022.
"ivWatch Model 400 to aid in intravenous infiltration detection user manual Rx only", ivWatch LLC, 2019, Rev 3.
Kern; et al., "Multi-Sensor Activity Context Detection for Wearable Computing", 2016.
Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.
Sachiko; T. Cochran et al, "Trends in Adverse Events After IV Administration of Contrast Media", Am. J. of Roentgenology, Jun. 2001, 176, 1385-1388.
Shaqdan; et al., "Incidence of contrast medium extravastion for CT and MRI in a large academic medical centre: A report on 502,391 injections", Clinical Radiology, Elsevier, 2014, 69, 1264-1272.
Turakhia; Et Eal., "Rationale and design of a large-scale, app-based study to identify cardiac arrhythmias using a smartwatch: The Apple Watch Study", Am Heart J, Jan. 2019, 207, 66-75.
Vinod; et al, "Acute compartment syndrome of hand resulting from radiograph contrast iohexol exravasation", Journal of Pharmacology and Pharmacotherapeutics, 2016, 44-7, 7-44.

* cited by examiner

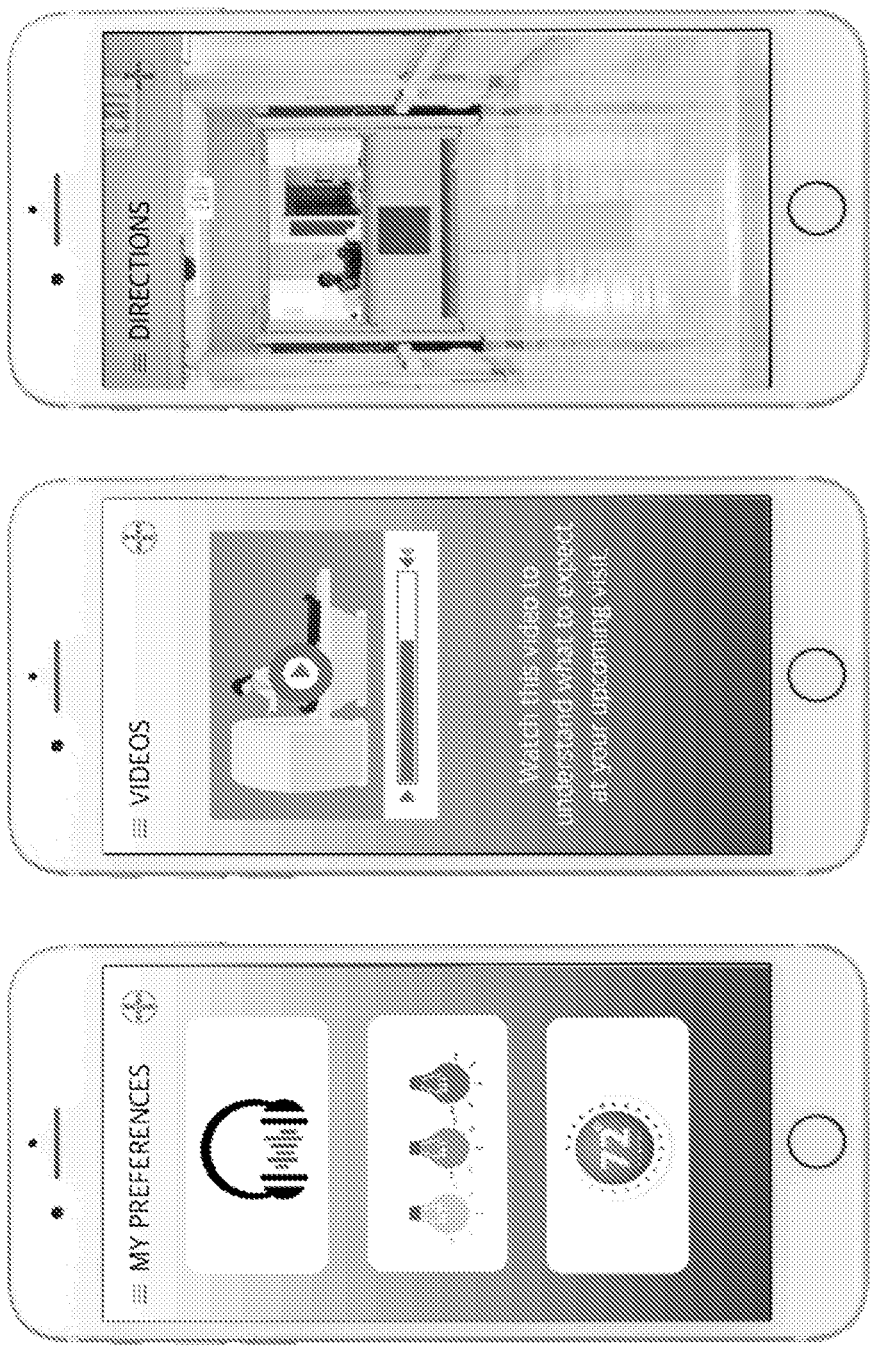

FIG. 15A

 REGISTRATION

PROCEDURES SECTION
Magnetic Resonance Imaging (MRI) scans create images of the body using a magnet and radio waves. While the procedure is much like CT scan, there is no radiation involved in an MRI exam. The MRI exam(s) in this study will take about ____ minutes.

To be sure that it is safe for you to have an MRI exam, you will be asked to complete standard MRI screening questionnares.

Since the MRI machine uses a strong magnet that will attract other metals, you may not take part in this study if you have a pacemaker, an implanted defibrillator, or certain other implanted electronic or metallic devices, shrapnel, or other metal.

Choose a or b:

(a) If you have a history of metal in your head or eyes, you cannot take part in this study.

(b) If you have a history of metal in your head or eyes, you cannot take part in this study.

Although the MRI machine is open at both ends, you may still feel confined (claustrophobic). If this bothers you, please tell the MRI staff. The MRI machine periodically makes loud banging noises. We will provide earplugs or headphones for you to wear during the MRI exam.

During the exam, you will be able to hear the MRI staff. They will be able to see and hear you.

If contrast will be used for the MRI exam, add the following language:
At some point during the MRI exam, the scanning procedure will be interrupted to give you a contrast agent through a needle in your arm.

RISKS SECTION
While no significant risks have been found from the use of the MRI scans, you may be bothered by the MRI machine noise and by feelings of being closed in (claustrophobia).

If gadolinium contrast will be used for the MRI exam, add the following language:
The contrast agent you will receive is FDA-approved and used routinely for MRI exams. It contains a material called gadolinium.

About 1 in 100 people may notice discomfort, tingling or warmth in the lips, metallic taste in the mouth, tingling in the arm, nausea, or headache. These symptoms go away quickly.
There is a small risk of an allergic reaction to gadolinium. However, a severe allergic reaction occurs in less than one in 300,000 people.
The placement of the needle (small plastic tube) to give you the gadolinium may cause minor pain, bruising and/or infection at the injection site.
People with severe kidney failure who receive gadolinium are at risk of developling Nephrogenic Systemimuch

SIGNATURE:

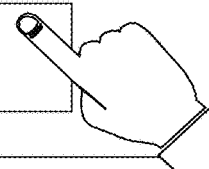

FIG. 15B

SYSTEM, DEVICE AND METHOD FOR SAFEGUARDING THE WELLBEING OF PATIENTS FOR FLUID INJECTION

CROSS REFERENCE TO RELATED APPLICATIONS

This application is a U.S. national phase application under 35 U.S.C. § 371 of International Application No. PCT/US2021/030210, filed Apr. 30, 2021, which claims priority to U.S. Provisional Patent Application No. 63/017,942, filed Apr. 30, 2020; U.S. Provisional Patent Application No. 62/706,597, filed Aug. 27, 2020; U.S. Provisional Patent Application No. 62/704,954, filed Jun. 4, 2020; and U.S. Provisional Patent Application No. 62/705,613, filed Jul. 7, 2020, the disclosures of which are incorporated by reference in their entireties.

BACKGROUND

The increase of medical imaging during the last decades has resulted in a substantial increase in the use of radiologic contrast media, across all modalities. Typically, 76 million computed tomographic (CT) and 34 million magnetic resonance (MR) imaging examinations are performed each year and about half of these examinations include the use of intravenous contrast agents. The use of intravenous contrast agents is well accepted in radiological society and the contrast media substances per se are accepted as safe. Besides the pharmacovigilance of contrast media, their practical use, by means of the application itself, may be associated with different risks.

For example, issues that exist in the context of patient safety and contrast media injection include at least the following: (i) extravasation prevention, detection, and minimization of extravasated substances; (ii) minimization of acute adverse events in each of contrast media naïve patients and patients with known atopy or a recorded acute adverse event due to a contrast media injection; (iii) prevention of a contrast media induced nephrotoxicity and/or a post contrast kidney injury; (iv) management of patients to prevent a thyroid disorder, such as thyrotoxicosis (TX), and/or the like.

Extravasation is an infrequent but significant problem in contrast enhanced medical imaging procedures. An extravasation occurs when contrast that is to be delivered to the central circulation through a peripheral vascular access instead enters the peripheral tissue (e.g., when contrast material escapes the vascular lumen and infiltrates the interstitial tissue during injection, etc.). The incidence of intravenous contrast material extravasation is typically reported as less than 1% and is not directly correlated with injection flow rate. However, some patients with extravasation may remain asymptomatic, while others may report swelling, tightness, stinging, or burning pain and may demonstrate edema, erythema, or tenderness at the injection site. Severe complications of extravasation include compartment syndrome, skin ulceration, and/or tissue necrosis.

Acute adverse events are dependent on applicated substances. The rate of acute adverse events for low osmolar iodinated contrast agents is approximately 0.2%-0.7%, and for severe acute reactions, 0.04%. The incidence of acute adverse events to gadolinium-based contrast agents (GBCAs) is low, occurring in approximately one in 10,000-40,000 injections. Most reactions are mild and transient, with skin reactions most frequently seen. Severe, life-threatening anaphylactoid reactions to GBCAs are rare. Risk factors for acute adverse events to contrast agents may include previous reactions to iodinated contrast agents, severe allergies and reactions to medications and/or foods, a history of asthma, bronchospasm, and/or atopy, a history of cardiac or renal disease, and/or the like.

A contrast media induced nephrotoxicity may be defined as "a sudden deterioration in renal function (e.g., acute kidney injury, etc.) following a recent intravascular administration of contrast media in the absence of another nephrotoxic event". Risk factors for a contrast media induced nephrotoxicity may include hypertension, proteinuria, gout, and/or previous renal surgery. A risk for a contrast media induced nephrotoxicity is considered low in patients with normal, stable renal function. Similarly, a post-contrast acute kidney injury is a general term used to indicate a sudden deterioration in renal function within 48 hours of the intravascular administration of iodine-based contrast media.

In a case of iodinated contrast media application, which reflects the majority of contrast media usage, patients with untreated Graves' disease and/or multinodular goiter and thyroid autonomy, the elderly, and patients living in areas where dietary iodine deficiency is common may be at increased risk of thyrotoxicosis through excess iodine absorption. Moreover, the use of iodinated contrast agents before any planned radioactive iodine imaging or therapy may reduce the radioactive iodine uptake.

An additional issue is that, because adverse events are relatively rare, it is hard to justify the cost and time to use the existing devices to monitor injections for adverse events and it is a challenge for healthcare professionals to be alert and diligent to manually discern the very few patients who may have an adverse event. In addition, in recent years, patient satisfaction is becoming an important factor in monetary reimbursement of healthcare providers.

SUMMARY

Accordingly, provided are improved systems, devices, products, apparatus, and/or methods for assessing, promoting, and safeguarding the wellbeing of patients for fluid injections (e.g., before, during, and/or after contrast media injection, etc.), which may provide a sensing and/or interpreting capability that utilizes multiple data sources to at least one of assess the wellbeing of a patient, the risk of an adverse event, recommend or take actions to maintain patient wellbeing and/or reduce or prevent the occurrence of an adverse event, minimize occurrence or severity of an adverse event, detect an adverse event, and/or manage an adverse event, for example extravasation, acute adverse events, contrast media induced nephrotoxicity and/or post contrast kidney injury, and/or thyroid disorders, thereby improving patient satisfaction, reimbursement, and reducing an occurrence of complications associated with contrast media injection. A further advantage of provided systems, devices, products, apparatus, and/or methods may be that by assessing and assisting in the promotion of the overall wellbeing of patients, they are applicable and useful in the medical care of all patients, not just in preventing or reducing harm to the few who might experience significant adverse events. Thus, provided systems, devices, products, apparatus, and/or methods may be more likely to become a part of the normal workflow and be used on all patients, thereby providing these benefits to all patients.

Non-limiting embodiments or aspects are set forth in the following numbered clauses:

Clause 1. A system comprising: at least one processor programmed and/or configured to: obtain patient data associated with the patient; determine, based on the patient data, an initial risk prediction for the patient associated with a fluid injection to be administered to the patient, wherein the initial risk prediction includes a probability that the patient experiences at least one adverse event in response to the fluid injection; provide, to a user device, before the fluid injection is administered to the patient, the initial risk prediction; obtain sensor data associated with the patient and determined after the fluid injection is started; determine, based on the sensor data determined after the fluid injection is started, a current risk prediction for the patient associated with the fluid injection, wherein the current risk prediction includes a probability that the patient experiences the at least one adverse event in response to the fluid injection; and provide, to the user device, the current risk prediction.

Clause 2. The system of clause 1, wherein the at least one processor is further programmed and/or configured to: automatically control, based on the current risk prediction, at least one of: (i) a fluid injection system to stop the fluid injection; and (ii) an imaging system to adjust a timing of an imaging operation.

Clause 3. The system of any of clauses 1 and 2, wherein the patient data includes at least one of the following parameters associated with the patient: an age; a gender; a weight; a prior chemotherapy status; an estimated glomerular filtration rate (eGFR); a thyroid stimulating hormone (TSH) level; a Triiodothyronine (FT3) Thyroxine (FT4) ratio (FT3/FT4); a level of an environmental influence; a prior reaction to a previous fluid injection status; an atopic disorder status; a medical status associated with at least one of diabetes and hypertension; a congestive heart failure status; a hematocrit level; a renal failure status; a malignancy status; an implanted device for a central venous access status; a type of a medication; a type of fluid media to be administered in the fluid injection; an injection protocol associated with a fluid injection; a type of an imaging exam; a flow rate associated with the fluid injection; a catheter gauge associated with the fluid injection; a total volume of fluid associated with the fluid injection; a pressure curve associated with the fluid injection, a pressure limit curve associated with a fluid injection, an injection site location associated with the fluid injection; or any combination thereof.

Clause 4. The system of any of clauses 1-3, wherein the at least one adverse event includes at least one of the following adverse events: an extravasation, a post-contrast acute kidney injury, an acute adverse event, a contrast media induced nephrotoxicity, a thyrotoxicosis, or any combination thereof.

Clause 5. The system of any of clauses 1-4, wherein the initial risk prediction further includes at least one of the following: a prompt to administer a medication to the patient before the fluid injection, a prompt to adjust an injection protocol for the fluid injection, a prompt to adjust an imaging protocol for an imaging scan; a prompt to prepare the patient before the fluid injection, a prompt to observe and/or follow-up with the patient after the fluid injection, or any combination thereof.

Clause 6. The system of any of clauses 1-5, wherein the sensor data includes at least one of the following parameters associated with the patient: a heart rate; a sound or vibration; a temperature; an oxygen saturation level; an ECG; a body fat/water-content ratio; a tissue impedance; a vessel distribution level; a vessel diameter; a hydration level; a hematocrit level; a skin resistivity; a blood pressure; a muscle tension level; a light absorptivity level; a motion level; an arm position; an arm circumference; a respiration rate; an amount of absorbed radiation; an EMG; a skin color; a surface vessel dilation amount; a bio-impedance; a light absorptivity; a hemoglobin level; an inflammation level; an environmental temperature of an environment surrounding the patient, a barometric pressure in an environment surrounding the patient; an ambient light level; an ambient sound level; or any combination thereof.

Clause 7. The system of any of clauses 1-6, further comprising: at least one sensor configured to determine, after the fluid injection is started, the sensor data associated with a patient.

Clause 8. The system of any of clauses 1-7, wherein the at least one sensor is further configured to: determine, during a test injection administered to the patient before the fluid injection, the sensor data, and wherein the at least one processor is further programmed and/or configured to: determine, based on the sensor data determined during the test injection, a test prediction, wherein the test prediction includes a probability that the patient experiences an extravasation in response to the fluid injection; and provide, to the user device, the test prediction.

Clause 9. The system of any of clauses 1-8, wherein the at least one sensor includes three sound or vibration sensors placed in three different locations on an extremity of the patient proximate an injection site for the test injection, and wherein the at least one processor is further programmed and/or configured to: combine, through triangulation, from each sound or vibration sensor of the three sound or vibration sensors, a data stream of the sensor data to create a combined data stream; and determine, based on the combined data stream, the test prediction.

Clause 10. The system of any of clauses 1-9, wherein the at least one sensor is further configured to: determine, before the test injection, the sensor data, wherein determining the initial risk prediction is further based on the sensor data determined before the test injection.

Clause 11. The system of any of clauses 1-10, wherein the at least one sensor is further configured to: determine, during the fluid injection, the sensor data, and wherein the at least one processor is further programmed and/or configured to: determine, based on the sensor data determined during the fluid injection, the current risk prediction; and provide, to the user device, during the fluid injection, the current risk prediction.

Clause 12. The system of any of clauses 1-11, wherein the at least one sensor is further configured to: determine, after the fluid injection, the sensor data, and wherein the at least one processor is further programmed and/or configured to: determine, based on the sensor data determined after the fluid injection, the current risk prediction; and provide, to the user device, after the fluid injection, the current risk prediction.

Clause 13. The system of any of clauses 1-12, wherein the at least one adverse event includes an extravasation, and wherein the at least one processor is further programmed and/or configured to provide the current risk prediction by automatically controlling, in response to determining that the patient experiences the extravasation, a fluid injection system to stop the fluid injection.

Clause 14. The system of any of clauses 1-13, wherein the at least one sensor includes at least one of the following sensors: an image capture device; an accelerometer; a strain gauge; a global positioning system (GPS); a skin resistivity or conductance sensor; a heart rate monitor; a microphone; a thermal or temperature sensor; a pulse oximeter; a hydration sensor; a dosimeter; an ultrasound sensor; an acoustic sensor; one or more electrodes configured to measure at least one of a tissue impedance, an electromyogram (EMG), and an electrocardiogram (ECG); a microwave sensor; a mechanical impedance sensor; a chemical sensor; a force or pressure sensor; or any combination thereof.

Clause 15. The system of any of clauses 1-14, further comprising: a sensor device, wherein the at least one sensor is included in the sensor device, and wherein the sensor device includes: an elongated housing extending between a first end and a second end, wherein the elongated housing is configured to surround an extremity of a patient, wherein the elongated housing includes a flexible exterior, wherein an interior of the elongated housing includes: the at least one sensor; and a wireless communication device, and wherein the wireless communication device is configured to wirelessly transmit the sensor data to an external device.

Clause 16. The system of any of clauses 1-15, wherein the interior of the elongated housing including the at least one sensor and the wireless communication device is fluidically sealed from an external environment by the flexible exterior of the elongated housing.

Clause 17. The system of any of clauses 1-16, wherein the at least one sensor includes a plurality of sensors, and wherein the plurality of sensors is spaced apart from each other along a length of the elongated housing extending from the first end of the elongated housing to the second end of the elongated housing such that the plurality of sensors is oriented in a pattern circumferentially around the extremity of the patient when the elongated housing surrounds the extremity of the patient, and wherein the plurality of sensors is configured to determine the sensor data in a transverse cross-section of the extremity of the patient.

Clause 18. The system of any of clauses 1-17, wherein the at least one adverse event includes an extravasation, wherein the at least one sensor includes an image capture device, wherein the image capture device is configured to: determine the sensor data, wherein the sensor data determined by the image capture device is associated with a plurality of images of the patient over a period of time, and wherein the at least one processor is further programmed and/or configured to: determine, based on the plurality of images of the patient over the period of time, the current risk prediction including the probability that the patient experiences the extravasation.

Clause 19. The system of any of clauses 1-18, wherein the at least one processor is further programmed and/or configured to: process the plurality of images of the patient over the period of time to enhance a change in at least one of a color and a motion between the plurality of images; and at least one of: display, with a display, to a user, the plurality of images including the enhanced change; and determine, based on the enhanced change, the current risk prediction including the probability that the patient experiences the extravasation, and, in response to determining that the current risk prediction including the probability that the patient experiences the extravasation satisfies a threshold probability, automatically controlling, with the at least one processor, a fluid injection system to stop the fluid injection.

Clause 20. The system of any of clauses 1-19, wherein the image capture device includes an infrared (IR) camera, and wherein the at least one processor is further programmed and/or configured to: process the plurality of images to determine a difference in absorption spectra between a first location on the patient and a second location on the patient in the plurality of images; and at least one of: display, with a display, to a user, the difference in absorption spectra between the first location on the patient and the second location on the patient; and determine, based on the difference in absorption spectra between the first location on the patient and the second location on the patient, the current risk prediction including the probability that the patient experiences the extravasation, and in response to determining that the current risk prediction including the probability that the patient experiences the extravasation satisfies a threshold probability, automatically control a fluid injection system to stop the fluid injection.

Clause 21. The system of any of clauses 1-20, wherein the first location on the patient includes a vessel of the patient, and wherein the second location on the patient includes tissue of the patient surrounding the vessel of the patient.

Clause 22. The system of any of clauses 1-21, further comprising: a sound generation device configured to induce, during the fluid injection, a sound signal into fluid delivered to the patient during the fluid injection, wherein the at least one sensor includes a sound or vibration sensor.

Clause 23. The system of any of clauses 1-22, wherein the sound generation device includes an oscillator connected to at least one of a syringe and a fluid path element that delivers the fluid to the patient during the fluid injection.

Clause 24. The system of any of clauses 1-23, wherein at least one of a frequency and an amplitude of the sound signal is tuned to enhance detection by the at least one sensor.

Clause 25. The system of any of clauses 1-24, wherein the at least one sensor includes a sound or vibration sensor, and wherein the sound or vibration sensor is configured to measure at least one of a frequency and an amplitude of a sound or vibration of the patient, wherein the at least one processor is further programmed and/or configured to: determine, based on the at least one of the frequency and the amplitude of the measured sound or vibration of the patient, the current risk prediction including the probability that the patient experiences an extravasation; and in response to determining that the current risk prediction including the probability that the patient experiences the extravasation satisfies a threshold probability, automatically control, with the at least one processor, a fluid injection system to stop the fluid injection.

Clause 26. The system of any of clauses 1-25, wherein the at least one processor is further programmed and/or configured to: determine, based on the sensor data determined after the fluid injection is started, a patient distress level; and provide, to the user device, the patient distress level.

Clause 27. The system of any of clauses 1-26, wherein the at least one processor is further programmed and/or configured to: compare the patient distress level to at least one threshold level; and in response to determining that the patient distress level satisfies the at least one threshold level, at least one of: provide, to a user device, an alert; and automatically control at least one of: (i) a fluid injection system to stop the fluid injection; and (ii) an imaging system to adjust a timing of an imaging operation.

Clause 28. The system of any of clauses 1-27, wherein the at least one processor is further programmed and/or configured to determine the distress level of the patient by: determining a change in one or more parameters of the sensor data over a period of time, and comparing the change in the one or more parameters to at least one threshold change.

Clause 29. The system of any of clauses 1-28, wherein the sensor data includes at least one of the following parameters associated with the patient: a heart rate, an oxygen saturation, a skin resistivity, a skin color, a movement level, a temperature proximate an injection site, or any combination thereof.

Clause 30. The system of any of clauses 1-29, wherein the at least one sensor includes at least one of the following sensors: a pulse oximeter, a skin resistance sensor, a skin color sensor, an accelerometer, a temperature sensor, or any combination thereof.

Clause 31. The system of any of clauses 1-30, further comprising: a sensor device, wherein the at least one sensor is included in the sensor device, wherein the sensor device includes a glove shaped housing configured to be worn on a hand of the patient, wherein the housing includes the at least one sensor and a wireless communication device, and wherein the wireless communication device is configured to wirelessly transmit the sensor data to an external device.

Clause 32. The system of any of clauses 1-31, further comprising: a sensor device, wherein the at least one sensor is included in the sensor device, wherein the sensor device includes: an elongated housing extending between a first end and a second end; and a pulse oximeter connected to the elongated housing via a wire, wherein the elongated housing is configured to surround at least one of a hand and a wrist of a patient, wherein the elongated housing includes a wireless communication device and at least one of a skin resistance sensor, an accelerometer, a temperature sensor, or any combination thereof, wherein the pulse oximeter and the at least one of the skin resistance sensor, the accelerometer, the temperature sensor, or any combination thereof are configured to determine the sensor data, and wherein the wireless communication device is configured to wirelessly transmit the sensor data to an external device.

Clause 33. The system of any of clauses 1-32, wherein the at least one processor is further programmed and/or configured to: control at least one of a light, a display, a speaker, and a haptic device to provide at least one of visual instructions, audio instructions, and haptic instructions for guiding breathing and/or positioning of the patient.

Clause 34. The system of any of clauses 1-33, wherein the at least one processor is further programmed and/or configured to: adjust, based on a timing of an imaging operation of an imaging system, the at least one of the visual instructions, the audio instructions, and the haptic instructions for guiding the breathing and/or the positioning of the patient.

Clause 35. The system of any of clauses 1-34, wherein the at least one processor is further programmed and/or configured to: determine, based on the sensor data determined after the fluid injection is started, the patient distress level; and adjust, in response to determining that the patient is distressed, the at least one of the visual instructions, the audio instructions, and the haptic instructions for guiding the breathing and/or the positioning of the patient.

Clause 36. A system comprising: at least one sensor configured to determine, before a fluid injection associated with a patient is started, sensor data associated with the patient; and at least one processor programmed and/or configured to: obtain patient data associated with the patient; and determine, based on the patient data and the sensor data, an initial risk prediction for the patient associated with the fluid injection to be administered to the patient, wherein the initial risk prediction includes a probability that the patient experiences at least one adverse event in response to the fluid injection; and provide, to a user device, before the fluid injection is administered to the patient, the initial risk prediction.

Clause 37. A system comprising: at least one sensor configured to determine, after a fluid injection associated with a patient is started, sensor data associated with the patient; and at least one processor programmed and/or configured to: determine, based on the sensor data determined after the fluid injection is started, a current risk prediction for the patient associated with the fluid injection, wherein the current risk prediction includes a probability that the patient experiences at least one adverse event in response to the fluid injection; and provide, to the user device, the current risk prediction.

Clause 38. A system comprising: at least one processor programmed and/or configured to: obtain sensor data associated with a patient and determined after a fluid injection associated with the patient is started; determine, based on the sensor data determined after the fluid injection is started, a current risk prediction for the patient associated with the fluid injection, wherein the current risk prediction includes a probability that the patient experiences at least one adverse event in response to the fluid injection; and provide, to the user device, the current risk prediction; and automatically control, based on the current risk prediction, at least one of: (i) a fluid injection system to stop the fluid injection; and (ii) an imaging system to adjust a timing of an imaging operation.

Clause 39. A system comprising: at least one sensor configured to determine sensor data associated with a patient at least one of before, during, and after a fluid injection associated with the patient; and at least one processor programmed and/or configured to: determine, based on the sensor data, a wellbeing level of the patient at least one of before, during, and during the fluid injection; and provide, to a user device, the wellbeing level of the patient.

Clause 40. A system comprising: at least one processor programmed and/or configured to: obtain sensor data associated with the patient and determined after a fluid injection associated with the patient is started; determine, based on the sensor data determined after the fluid injection is started, a wellbeing level of the patient during the fluid injection; provide, to a user device, the wellbeing level of the patient; and automatically control, based on the wellbeing level of the patient, at least one of: (i) a fluid injection system to adjust at least one of a maximum flow rate, a maximum pressure, an injection duration, a total volume of fluid, or any combination thereof, of the fluid injection; and (ii) an imaging system to adjust a timing of an imaging operation.

Clause 41. A system comprising: at least one processor programmed and/or configured to: provide, via an application program interface (API), to at least one user device, information associated with a fluid injection to be administered to a patient; receive, via the API, from the at least one user device, before the fluid injection, patient data associated with the patient, wherein the patient data includes at least one patient preference associated with the fluid injection, and wherein the at least one patient preference associated with the fluid injection includes at least one of the following patient preferences: a lighting preference during the fluid injection, an audio preference during the fluid injection, a temperature preference during the fluid injection, or any combination thereof; and automatically control, during the fluid injection, based on the at least one patient preference, at least one of the following: (i) a light source, (ii) an audio source, (iii) a haptic device, (iv) a heating, ventilation, and air conditioning (HVAC) system, or any combination thereof.

Clause 42. The system of clause 41, further comprising: at least one of a fluid injector and a medical imager, wherein the at least one of the fluid injector and the medical imager includes at least one of the following: (i) the light source, (ii) the audio source, (iii) the haptic device, or any combination thereof.

Clause 43. The system of any of clauses 41 and 42, wherein the light source includes a display of the at least one of the fluid injector and the medical imager.

Clause 44. The system of any of clauses 41-43, wherein the haptic device includes a bed or table of the medical imager.

Clause 45. The system of any of clauses 41-44, further comprising: at least one sensor configured to determine, during the fluid injection, sensor data associated with the patient, wherein the at least one processor is further programmed and/or configured to automatically control, during the fluid injection, based on the sensor data, at least one of the following: (i) the light source, (ii) the audio source, (iii) the haptic device, or any combination thereof, to guide breathing and/or positioning of the patient.

Clause 46. The system of any of clauses 41-45, wherein the at least one processor further automatically controls, during the fluid injection, the at least one of the following: (i) the light source, (ii) the audio source, (iii) the haptic device, or any combination thereof, based on a timing of an imaging operation of the medical imager.

Clause 47. The system of any of clauses 41-46, wherein the at least one processor is further programmed and/or configured to: automatically control, based on the sensor data, at least one of: (i) a fluid injector to stop the fluid injection; and (ii) a medical imager to adjust a timing of an imaging operation.

Clause 48. A system comprising: at least one processor programmed and/or configured to: provide, via an application program interface (API), to at least one user device, information associated with a fluid injection to be administered to a patient; receive, via the API, from the at least one user device, before the fluid injection, patient data associated with the patient, wherein the patient data includes at least one patient preference associated with the fluid injection, and wherein at least one piece of patient data is used in a risk prediction for assessing a probability of the patient experiencing an adverse event during a fluid injection.

Clause 49. The system of clause 48, further comprising: at least one of a fluid injector and a medical imager, wherein parameters of at least one of an injection protocol of the fluid injection and an imaging protocol of the medical imager are adjusted based on the at least one piece of patient data.

Clause 50. A sensor device comprising: at least one sensor configured to determine sensor data associated with a patient at least one of before, during, and after a fluid injection associated with the patient; an elongated housing extending between a first end and a second end, wherein the elongated housing is configured to surround an extremity of the patient, wherein the elongated housing includes a flexible exterior, wherein an interior of the elongated housing includes the at least one sensor and a wireless communication device, and wherein the wireless communication device is configured to wirelessly transmit the sensor data to an external device.

Clause 51. The system of clause 50, wherein the interior of the elongated housing including the at least one sensor and the wireless communication device is fluidically sealed from an external environment by the flexible exterior of the elongated housing.

Clause 52. The system of any of clauses 50 and 51, wherein the at least one sensor includes a plurality of sensors, and wherein the plurality of sensors is spaced apart from each other along a length of the elongated housing extending from the first end of the elongated housing to the second end of the elongated housing such that the plurality of sensors is oriented in a pattern circumferentially around the extremity of the patient when the elongated housing surrounds the extremity of the patient, and wherein the plurality of sensors is configured to determine the sensor data in a transverse cross-section of the extremity of the patient.

Clause 53. The system of any of clauses 50-52, wherein the at least one sensor includes at least one of the following sensors: an image capture device; an accelerometer; a strain gauge; a global positioning system (GPS); a skin resistivity or conductance sensor; a heart rate monitor; a microphone; a thermal or temperature sensor; a pulse oximeter; a hydration sensor; a dosimeter; an ultrasound sensor; an acoustic sensor; one or more electrodes configured to measure at least one of a tissue impedance, an electromyogram (EMG), and an electrocardiogram (ECG); a microwave sensor; a mechanical impedance sensor; a chemical sensor; a force or pressure sensor; or any combination thereof.

Clause 54. A sensor device comprising: at least two sensors configured to measure at least two different parameters associated with a patient at least one of before, during, and after a fluid injection associated with the patient; and at least one processor programmed and/or configured to: determine, based on the at least two different parameters, at least one of (i) a patient distress level and (ii) a risk prediction for the patient associated with the fluid injection, wherein the risk prediction includes a probability that the patient experiences at least one adverse event in response to the fluid injection; and provide, to a user device, the at least one of the patient distress level and the risk prediction.

Clause 55. A sensor device comprising: at least one sensor configured to determine sensor data associated with a patient at least one of before, during, and after a fluid injection associated with the patient; a glove shaped housing configured to be worn on a hand of the patient, wherein the housing includes the at least one sensor and a wireless communication device, and wherein the wireless communication device is configured to wirelessly transmit the sensor data to an external device.

Clause 56. A sensor device comprising: an elongated housing extending between a first end and a second end; and a pulse oximeter connected to the elongated housing via a wire, wherein the elongated housing is configured to surround at least one of a hand and a wrist of the patient, wherein the elongated housing includes a wireless communication device and at least one sensor, wherein the at least one sensor includes at least one of a skin resistance sensor, an accelerometer, a temperature sensor, or any combination thereof, wherein the pulse oximeter and the at least one of the skin resistance sensor, the accelerometer, the temperature sensor, or any combination thereof are configured to determine sensor data associated with a patient at least one of before, during, and after a fluid injection associated with the patient, and wherein the wireless communication device is configured to wirelessly transmit the sensor data to an external device.

Clause 57. A method comprising: obtaining, with at least one processor, patient data associated with a patient; determining, with the at least one processor, based on the patient data, an initial risk prediction for the patient associated with a fluid injection to be administered to the patient, wherein the initial risk prediction includes a probability that the patient experiences at least one adverse event in response to the fluid injection; providing, with the at least one processor, to a user device, before the fluid injection is administered to the patient, the initial risk prediction; determining, with at least one sensor, after the fluid injection is started, sensor data associated with the patient; determining, with the at least one processor, based on the sensor data determined after the fluid injection is started, a current risk prediction for the patient associated with the fluid injection, wherein the current risk prediction includes a probability that the patient experiences the at least one adverse event in response to the fluid injection; and providing, with the at least one processor, to the user device, the current risk prediction.

Clause 58. The method of clause 57, wherein the patient data includes at least one of the following parameters associated with the patient: an age; a gender; a weight; a prior chemotherapy status; an estimated glomerular filtration rate (eGFR); a thyroid stimulating hormone (TSH) level; a Triiodothyronine (FT3) Thyroxine (FT4) ratio (FT3/FT4); a level of an environmental influence; a prior reaction to a previous fluid injection status; an atopic disorder status; a medical status associated with at least one of diabetes and hypertension; a congestive heart failure status; a hematocrit level; a renal failure status; a malignancy status; an implanted device for a central venous access status; a type of a medication; a type of fluid to be administered in the fluid injection; a type of the fluid injection; a type of an imaging exam; a flow rate associated with the fluid injection; a catheter gauge associated with the fluid injection; a total volume of fluid associated with the fluid injection; a pressure curve associated with the fluid injection, an injection site location associated with the fluid injection; or any combination thereof.

Clause 59. The method of any of clauses 57 and 58, wherein the at least one adverse event includes at least one of the following adverse events: an extravasation, a post-contrast acute kidney injury, an acute adverse event, a contrast media induced nephrotoxicity, a thyrotoxicosis, or any combination thereof.

Clause 60. The method of any of clauses 57-59, wherein the initial risk prediction further includes at least one of the following: a prompt to administer a medication to the patient before the fluid injection, a prompt to adjust an injection protocol for the fluid injection, a prompt to adjust an imaging protocol for an imaging scan; a prompt to prepare the patient before the fluid injection, a prompt to observe and/or follow-up with the patient after the fluid injection, or any combination thereof.

Clause 61. The method of any of clauses 57-60, wherein the sensor data includes at least one of the following parameters associated with the patient: a heart rate; a sound or vibration; a temperature; an oxygen saturation level; an ECG; a body fat/water-content ratio; a tissue impedance; a vessel distribution level; a vessel diameter; a hydration level; a hematocrit level; a skin resistivity; a blood pressure; a muscle tension level; a light absorptivity level; a motion level; an arm position; an arm circumference; a respiration rate; an amount of absorbed radiation; an EMG; a skin color; a surface vessel dilation amount; a bio-impedance; a light absorptivity; a hemoglobin level; an inflammation level; an environmental temperature of an environment surrounding the patient, a barometric pressure in an environment surrounding the patient; an ambient light level; an ambient sound level; or any combination thereof.

Clause 62. The method of any of clauses 57-61, further comprising: determining, with the at least one sensor, during a test injection administered to the patient before the fluid injection, the sensor data; determining, with the at least one processor, based on the sensor data determined during the test injection, a test prediction, wherein the test prediction includes a probability that the patient experiences an extravasation in response to the fluid injection; and providing, with the at least one processor, to the user device, the test prediction.

Clause 63. The method of any of clauses 57-62, wherein the at least one sensor includes three sound or vibration sensors placed in three different locations on an extremity of the patient proximate an injection site for the test injection, and wherein the method further includes: combining, with the at least one processor, through triangulation, from each sound or vibration sensor of the three sound or vibration sensors, a data stream of the sensor data to create a combined data stream; and determining, with the at least one processor, based on the combined data stream, the test prediction.

Clause 64. The method of any of clauses 57-63, further comprising: determining, with the at least one sensor, before the test injection, the sensor data, wherein determining the initial risk prediction is further based on the sensor data determined before the test injection.

Clause 65. The method of any of clauses 57-64, further comprising: determining, with the at least one sensor, during the fluid injection, the sensor data; determining, with the at least one processor, based on the sensor data determined during the fluid injection, the current risk prediction for the patient associated with the fluid injection; and providing, to the user device, during the fluid injection the current risk prediction.

Clause 66. The method of any of clauses 57-65, further comprising: determining, with the at least one sensor, after the fluid injection, the sensor data; determining, with the at least one processor, based on the sensor data determined after the fluid injection, the current risk prediction for the patient associated with the fluid injection; and providing, to the user device, after the fluid injection the current risk prediction.

Clause 67. The method of any of clauses 57-66, wherein the at least one adverse event includes an extravasation, and wherein providing the current risk prediction further includes, in response to determining that the patient experiences the extravasation, automatically controlling, with the at least one processor, a fluid injection system to stop the fluid injection.

Clause 68. The method of any of clauses 57-67, wherein the at least one sensor includes at least one of the following sensors: an image capture device; an accelerometer; a strain gauge; a global positioning system (GPS); a skin resistivity or conductance sensor; a heart rate monitor; a microphone; a thermal or temperature sensor; a pulse oximeter; a hydration sensor; a dosimeter; an ultrasound sensor; an acoustic sensor; one or more electrodes configured to measure at least one of a tissue impedance, an electromyogram (EMG), and an electrocardiogram (ECG); a microwave sensor; a mechanical impedance sensor; a chemical sensor; a force or pressure sensor; or any combination thereof.

Clause 69. The method of any of clauses 57-68, wherein the at least one sensor is included in a sensor device, and wherein the sensor device includes: an elongated housing extending between a first end and a second end, wherein the elongated housing is configured to surround an extremity of a patient, wherein the elongated housing includes a flexible exterior, and wherein an interior of the elongated housing includes: the at least one sensor; and a wireless communication device, and wherein the method further comprises: wirelessly transmitting, with the wireless communication device, the sensor data to an external device.

Clause 70. The method of any of clauses 57-69, wherein the interior of the elongated housing including the at least one sensor and the wireless communication device is fluidically sealed from an external environment by the flexible exterior of the elongated housing.

Clause 71. The method of any of clauses 57-70, wherein the at least one sensor includes a plurality of sensors, and wherein the plurality of sensors are spaced apart from each other along a length of the elongated housing extending from the first end of the elongated housing to the second end of the elongated housing such that the plurality of sensors are oriented in a pattern circumferentially around the extremity of the patient when the elongated housing surrounds the extremity of the patient, and wherein the method further comprises: determining, with the plurality of sensors, the sensor data in a transverse cross-section of the extremity of the patient.

Clause 72. The method of any of clauses 57-71, wherein the at least one adverse event includes an extravasation, wherein the at least one sensor includes an image capture device, and wherein the method further comprises: determining, with the image capture device, the sensor data, wherein the sensor data determined by the image capture device is associated with a plurality of images of the patient over a period of time; and determining, with the at least one processor, based on the plurality of images of the patient over the period of time, the current risk prediction including the probability that the patient experiences the extravasation.

Clause 73. The method of any of clauses 57-72, further comprising: processing, with the at least one processor, the plurality of images of the patient over the period of time to enhance a change in at least one of a color and a motion between the plurality of images; and with the at least one processor, at least one of: displaying, with a display, to a user, the plurality of images including the enhanced change; and determining, with the at least one processor, based on the enhanced change, the current risk prediction including the probability that the patient experiences the extravasation, and, in response to determining that the current risk prediction including the probability that the patient experiences the extravasation satisfies a threshold probability, automatically controlling, with the at least one processor, a fluid injection system to stop the fluid injection.

Clause 74. The method of any of clauses 57-73, wherein the image capture device includes an infrared (IR) camera, and wherein the method further comprises: processing, with the at least one processor, the plurality of images to determine a difference in absorption spectra between a first location on the patient and a second location on the patient in the plurality of images; and with the at least one processor, at least one of: displaying, with a display, to a user, the difference in absorption spectra between the first location on the patient and the second location on the patient; and determining, based on the difference in absorption spectra between the first location on the patient and the second location on the patient, the current risk prediction including the probability that the patient experiences the extravasation, and in response to determining that the current risk prediction including the probability that the patient experiences the extravasation satisfies at least one threshold probability, automatically controlling a fluid injection system to stop the fluid injection.

Clause 75. The method of any of clauses 57-74, wherein the first location on the patient includes a vessel of the patient, and wherein the second location on the patient includes tissue of the patient surrounding the vessel of the patient.

Clause 76. The method of any of clauses 57-75, further comprising: inducing, with a sound generation device, during the fluid injection, a sound signal into fluid delivered to the patient during the fluid injection.

Clause 77. The method of any of clauses 57-76, wherein the sound generation device includes an oscillator connected to at least one of a syringe and tubing that delivers the fluid to the patient during the fluid injection.

Clause 78. The method of any of clauses 57-77, wherein at least one of a frequency and an amplitude of the sound signal is tuned to enhance detection by the at least one sensor.

Clause 79. The method of any of clauses 57-78, wherein the at least one sensor includes a sound or vibration sensor, and wherein the method further comprises: measuring, with the sound or vibration sensor, at least one of a frequency and an amplitude of a sound or vibration of the patient; determining, with the at least one processor, based on the at least one of the frequency and the amplitude of the measured sound or vibration of the patient, the current risk prediction including the probability that the patient experiences an extravasation; and in response to determining that the current risk prediction including the probability that the patient experiences the extravasation satisfies at least one threshold probability, automatically controlling, with the at least one processor, a fluid injection system to stop the fluid injection.

Clause 80. The method of any of clauses 57-79, further comprising: determining, with the at least one processor, based on the sensor data determined after the fluid injection is started, a patient distress level; comparing, with the at least one processor, the patient distress level to at least one threshold level; and in response to determining that the patient distress level satisfies the at least one threshold level, at least one of: providing, with the at least one processor, to a user device, an alert; and automatically controlling, with the at least one processor, at least one of: (i) a fluid injection system to stop the fluid injection; and (ii) an imaging system to adjust a timing of an imaging operation.

Clause 81. The method of any of clauses 57-80, wherein the determining the patient distress level includes: determining a change in one or more parameters of the sensor data over a period of time, and comparing the change in the one or more parameters to at least one threshold change.

Clause 82. The method of any of clauses 57-81, wherein the sensor data includes at least one of the following parameters associated with the patient: a heart rate, an oxygen saturation, a skin resistivity, a movement level, a temperature proximate an injection site, or any combination thereof.

Clause 83. The method of any of clauses 57-82, wherein the at least one sensor includes at least one of the following sensors: a pulse oximeter, a skin resistance sensor, an accelerometer, a temperature sensor, or any combination thereof.

Clause 84. The method of any of clauses 57-83, wherein the at least one sensor is included in a sensor device, wherein the sensor device includes a glove shaped housing configured to be worn on a hand of the patient, and wherein the housing includes the at least one sensor and a wireless communication device, and wherein the method further comprises: wirelessly transmitting, with the wireless communication device, the sensor data to an external device.

Clause 85. The method of any of clauses 57-84, wherein the at least one sensor is included in a sensor device, wherein the sensor device includes an elongated housing extending between a first end and a second end and a pulse oximeter connected to the elongated housing via a wire, wherein the elongated housing is configured to surround at least one of a hand and a wrist of a patient, wherein the elongated housing includes a wireless communication device and at least one of a skin resistance sensor, an accelerometer, a temperature sensor, or any combination thereof, and wherein the method further comprises: determining, with the pulse oximeter and the at least one of the skin resistance sensor, the accelerometer, the temperature sensor, or any combination thereof, the sensor data; wirelessly transmitting, with the wireless communication device, the sensor data to an external device.

Clause 86. The method of any of clauses 57-85, further comprising: controlling, with the at least one processor, at least one of a light, a display, a speaker, and a haptic device to provide at least one of visual instructions, audio instructions, and haptic instructions for guiding breathing and/or positioning of the patient.

Clause 87. The method of any of clauses 57-86, further comprising: adjusting, with the at least one processor, based on a timing of an imaging operation of an imaging system, the at least one of the visual instructions, the audio instructions, and the haptic instructions for guiding the breathing and/or positioning of the patient.

Clause 88. The method of any of clauses 57-87, further comprising: determining, with the at least one processor, based on the sensor data determined after the fluid injection is started, a patient distress level; and adjusting, with the at least one processor, in response to determining that the patient is distressed, the at least one of the visual instructions, the audio instructions, and the haptic instructions for guiding the breathing and/or the positioning of the patient.

Clause 89. The method of any of clauses 57-88, further comprising: automatically controlling, with the at least one processor, based on the current risk prediction, at least one of: (i) a fluid injection system to stop the fluid injection; and (ii) an imaging system to adjust a timing of an imaging operation.

BRIEF DESCRIPTION OF THE DRAWINGS

Additional advantages and details are explained in greater detail below with reference to the exemplary embodiments that are illustrated in the accompanying schematic figures, in which:

FIGS. 14A-14C illustrate non-limiting embodiments or aspects of a patient portal application accessible via a user device; and FIGS. 15A and 15B illustrate non-limiting embodiments or aspects of a patient portal application accessible via a user device.

DETAILED DESCRIPTION

Figure 1A:
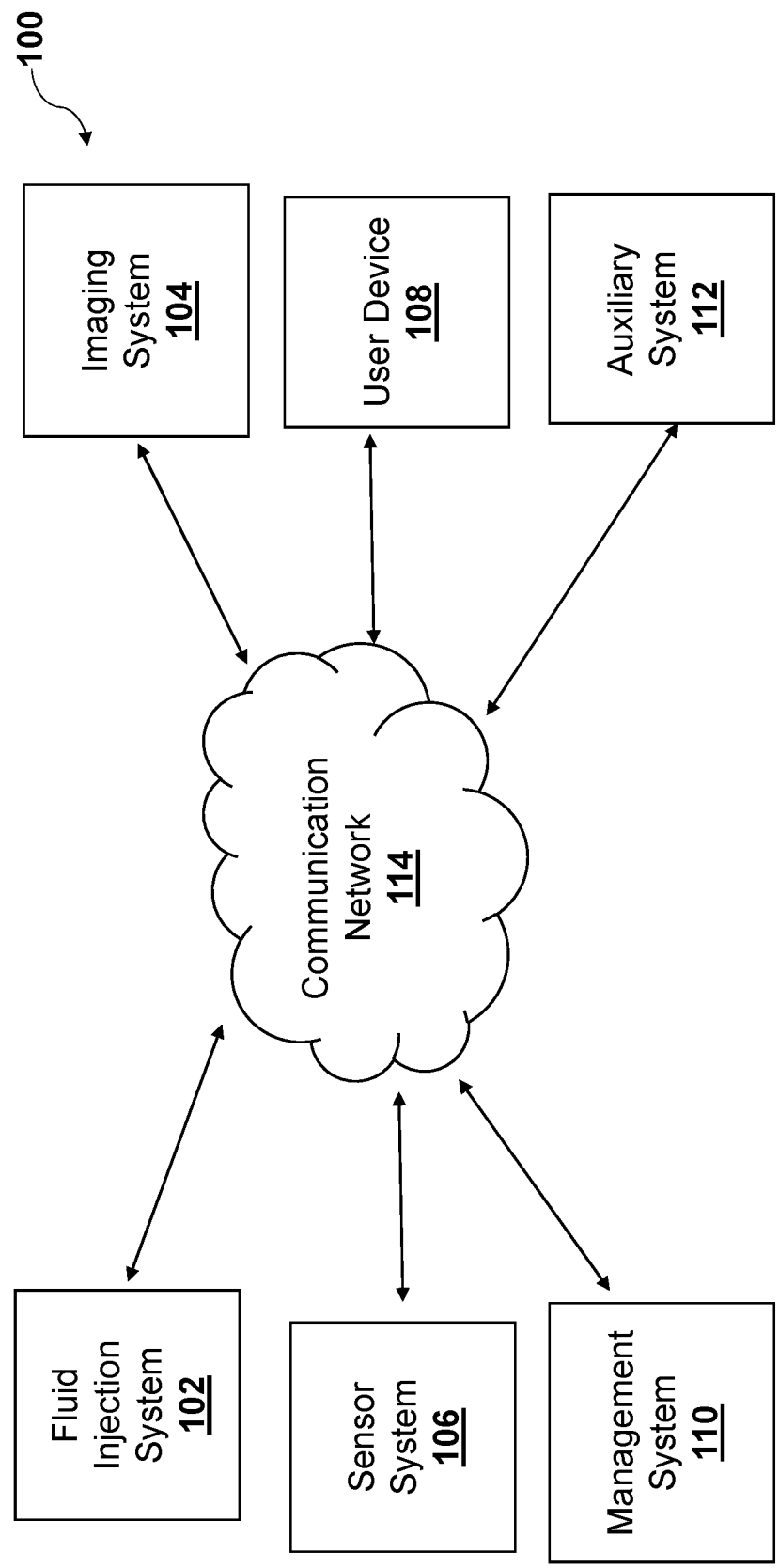
FIG. 1A is a diagram of non-limiting embodiments or aspects of an environment in which systems, devices, products, apparatus, and/or methods, described herein, can be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

Similarly, it is also to be understood that contrast media injections are simply exemplary of drugs or pharmaceuticals being injected intravascularly, the injection of which may benefit from the use of non-limiting embodiments or aspects of the present disclosure. In addition to, or in alternative to, contrast media, example intravascular injections may include any imaging agents, saline, any flushing fluids, stress agents, chemotherapy agents, radiotherapy agents, spasmolytic or antispasmodic agents, thrombolytics, anti-thrombotic agents, antibiotics, intra-venous immunoglobulin (IVIG), parenteral nutrition, pain medications, and/or radiopharmaceuticals. Similarly, the use of the devices, systems, and processes of the present disclosure are not limited to imaging suites but may be useful wherever intravascular injections take place, including, for example, in other healthcare facilities, in a patient's home, and/or the like.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located informationally between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible. Communication between the first unit and the second unit may take place via any medium or intermediary, including for example a human manually or verbally communicating the information.

As used herein, the term "computing device" may refer to one or more electronic devices that are configured to communicate directly or indirectly with or over one or more networks. A computing device may be a mobile or portable computing device, a desktop computer, a server, and/or the like. Furthermore, the term "computer" may refer to any computing device that includes the necessary components to receive, process, and output data, and normally includes a display, a processor, a memory, an input device, and a network interface. A "computing system" may include one or more computing devices or computers. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.). Further, multiple computers, e.g., servers, or other computerized devices directly or indirectly communicating in the network environment may constitute a "system" or a "computing system".

As used herein, terms such as user, physician, healthcare worker, and/or caregiver may include any person associated with devices, systems, and processes of the present disclosure and/or any person that is assisting in caring for a patient, including the patient himself or herself or the patient's guardian or power of attorney. For example, these terms are intended to include persons, such as doctors, referring physicians, radiologists, nurses, technologists, radiologists, oncologists, radiographers, social service worker, aides, volunteers, family members, and/or the like. Users may also include workers in the healthcare provision or payment systems such as hospital or radiology administrators, clerks, regulators, insurance or payor company workers; and others who may possess, control, and/or provide information used by non-limiting embodiments or aspects or benefit from the information provided by this system.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc. Unless otherwise stated, thresholds are exemplary and may depend or vary, for example, based upon the patient population involved.

Figure 1B:
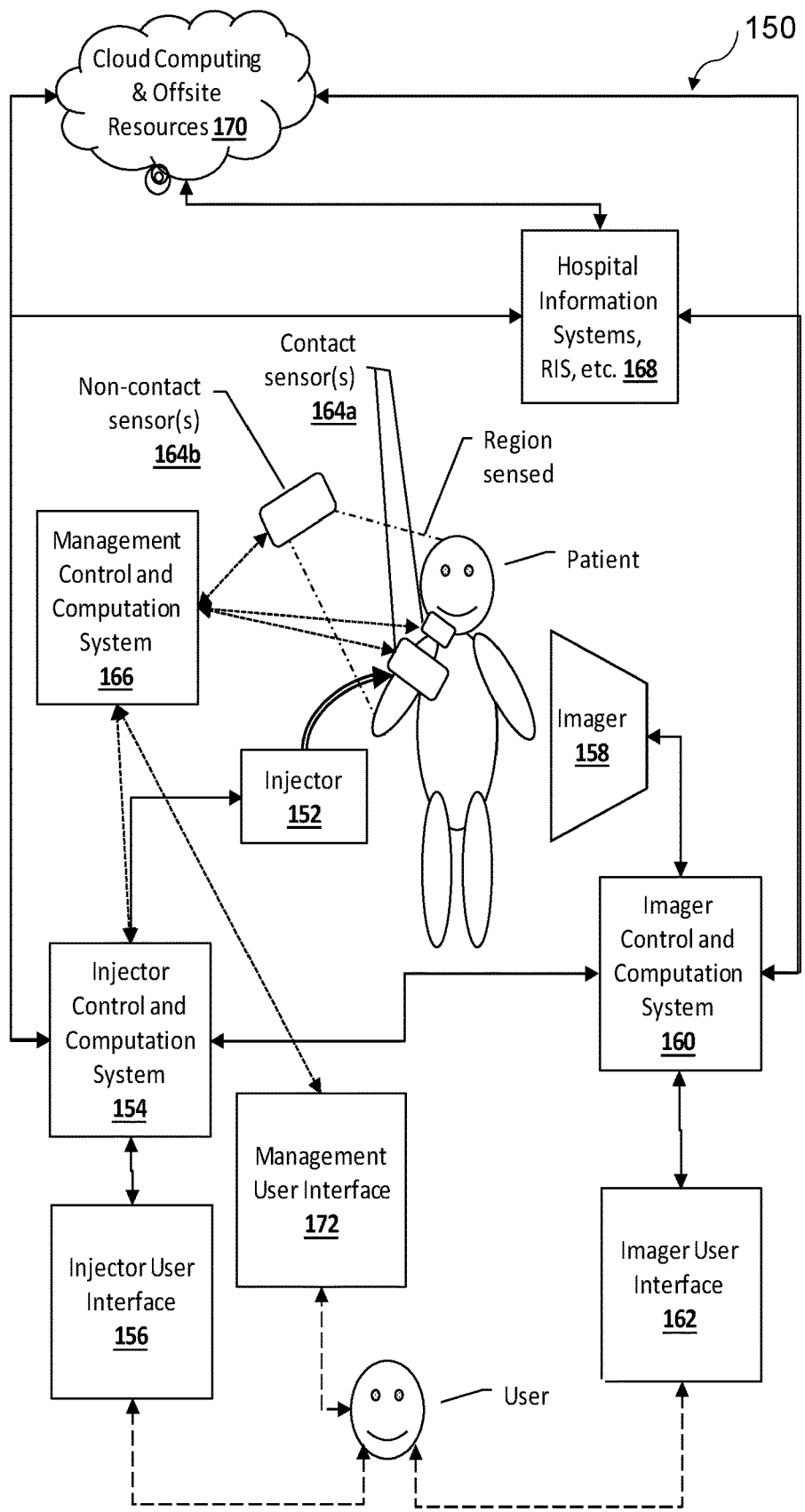
FIG. 1B is a diagram of non-limiting embodiments or aspects of an implementation of the environment of FIG. 1A.

Referring now to FIG. 1A, FIG. 1A is a diagram of an example environment 100 in which systems, devices, products, apparatus, and/or methods described herein, may be implemented. As shown in FIG. 1A, environment 100 includes fluid injector system 102, imaging system 104, sensor system 106, user device 108, management system 110, auxiliary system 112, and/or communication network 114. Referring also to FIG. 1B, FIG. 1B is a diagram of non-limiting embodiments or aspects of an implementation 150 of environment 100 of FIG. 1A. As shown in FIG. 1B, implementation 100 may include injector 152, injector control and computation system 154, injector user interface 156, imager 158, imager control and computation system 160, imager user interface 162, contact sensor(s) 164a, non-contact sensor(s) 164b, control and computation system 166, hospital information system(s) 168, cloud computing and offsite resources 170, and/or management user interface 172. Systems and/or devices of environment 100 and/or implementation 150 may interconnect (e.g., communicate information and/or data, etc.) via wired connections, wireless connections, or a combination of wired and wireless connections (e.g., via communication network 114, etc.).

Fluid injection system 102 may include one or more devices, software, and/or hardware configured to set up one or more injection protocols and deliver one or more fluids (e.g., contrast agents, etc.) to a patient according to one or more injection protocols. An injection protocol commonly includes one or more phases, with each phase specifying the fluid and optionally fluid concentration to be injected, and two of the flow rate, volume, and duration of that phase of the injection (e.g., because volume injected=flow rate× duration, there are only two independent variables out of those three parameters). Other injection parameters which may be different for different phase or constant for all phases may include at least one of pressure limits, flow rate limits, occlusion indications, or any combination thereof. Some injectors may be configured to have a time varying value of one, some, or all of the injection parameters. For example, fluid injection system 102 may include injector 152, injector control and computation system 154, and/or injector user interface 156. As an example, fluid injection system 102 may include a contrast injection system as described in U.S. Pat. Nos. 6,643,537 and/or 7,937,134 and/or as described in published International Application No. WO2019046299A1, the entire contents of each of which is hereby incorporated by reference. As an example, fluid injection system 102 may include the MEDRAD® Stellant FLEX CT Injection System, the MEDRAD® MRXperion MR Injection System, the MEDRAD® Mark 7 Arterion Injection System, the MEDRAD® Intego PET Infusion System, the MEDRAD® Spectris Solaris EP MR Injection System, the MEDRAD® Stellant CT Injection System With Certegra® Workstation, and/or the like.

Imaging system 104 may include one or more devices, software, and/or hardware configured to set up imaging protocols and acquire non-contrast and contrast-enhanced scans of a patient. For example, imaging system 104 may include imager 158, imager control and computation system 160, and/or imager user interface 162. As an example, imaging system 104 may include a magnetic resonance imaging (MRI) system, a computed tomography (CT) system, an ultrasound system, a single-photon emission computed tomography (SPECT) system, a positron emission tomography-magnetic resonance (PET/MRI) system, a positron emission tomography-computed tomography (PET/CT) system, an angiography system, an interventional radiology (IR) system, and/or other imaging modalities used on humans or animals. As an example, imaging system 104 may include an imaging system as described in U.S. Patent Application Publication No. 2020/0146647A1, filed on Dec. 11, 2019, the entire contents of which is hereby incorporated by reference. In some non-limiting embodiments or aspects, imaging system 104 may include Siemens Healthineers' Somatom Go CT Systems, General Electric's Signa MR Systems, and/or the like.

Sensor system 106 may include sensor(s) 164 configured to determine (e.g., determine, collect, acquire, capture, measure, sense, etc.) sensor data associated with a patient and/or a fluid injection (e.g., a contrast media injection, etc.) for the patient. For example, sensor system 106 may include contact sensor(s) 164a (e.g., a sensor that contacts a patient to determine sensor data, a sensor included in contact sensor device 400 and/or 800 wearable by a patient, etc.) and/or non-contact sensors 164b (e.g., a sensor device that does not contact a patient to determine sensor data, etc.).

Contact sensor 164a may include at least one of the following sensors: an accelerometer; a strain gauge; a global positioning system (GPS); a skin resistivity or conductance sensor; a heart rate monitor; a microphone (e.g., a microphone configured to measure sound in tissue of a patient, for example an inflow sound of contrast media, saline, or other drugs in a vessel, etc.); a thermal or temperature sensor (e.g., a temperature sensor configured to measure a change in tissue temperature due to injected saline and/or contrast fluid, etc.); a pulse oximeter (e.g. a pulse oximeter configured to measure a pulse rate, a change in oxygenation level, a patient hydration, and/or a local tissue perfusion, etc.); a hydration sensor; a dosimeter; an epiwatch; an ultrasound sensor; an acoustic sensor (e.g., a sonic acoustic sensor, an infrasonic acoustic sensor, etc.); one or more electrodes configured to measure tissue impedance, perform an electromyogram (EMG), and/or an electrocardiogram (ECG or EKG); a respiration measuring sensor; a microwave sensor; a mechanical impedance sensor; a chemical sensor; a force or pressure sensor; or any combination thereof. In some non-limiting embodiments or aspects, contact sensor 164a may be included in contact sensor device 400 and/or contact sensor device 800 as described herein. In some non-limiting embodiments or aspects, contact sensor 164a may be included on at least one of the following locations; a catheter (e.g., a tip of a catheter, etc.), on an arm of a patient over a tip of a catheter in the patient, on an arm of a patient proximate to an injection site or a tip of a catheter in the patient, on a connector tube upstream of a catheter, on another portion of a body of a patient; on an area surrounding an injection site, or any combination thereof. In some non-limiting embodiments or aspects, contact sensor 164a may include a single device including a single sensor, a single device including multiple sensors, and/or multiple devices including either a single sensor or multiple sensors. Existing devices including existing sensors may be incorporated into non-limiting embodiments or aspects of sensor system 106 and/or provide measurements to sensor system 106. Example existing devices may include an Apple watch, a Fitbit exercise monitor, and/or the like, which a patient may be wearing, ECG or respiratory monitors that may be part of imaging system 104, pulse oximeters or other monitoring equipment that may already be available and/or in use in an imaging suite and/or healthcare facility, and/or the like.

Non-contact sensor 164b may include one or more image capture devices configured to capture a plurality of images of a patient over a period of time (e.g., images of an injection site and/or an area surrounding an injection site, etc.), such as a camera (e.g., a visible light camera, an infrared (IR) camera, etc.), a LiDAR sensor, or any combination thereof. An IR camera may include at least one of the following IR cameras: a near IR camera (e.g., silicon sensing, etc.) configured to capture light having a near IR wavelength, a short wavelength IR camera configured as a spectral imager to capture light having a short IR wavelength, a medium wavelength IR camera configured to capture light having a medium IR wavelength, a long wavelength IR camera configured to capture light having a long IR wavelength, or any combination thereof.

In some non-limiting embodiments or aspects, non-contact sensor 164b may include an image capture device configured to capture images using ambient illumination. In some non-limiting embodiments or aspects, non-contact sensor 164b may include one or more illumination devices configured to provide at least one of the following types of illumination for an image capture device: additional ambient illumination, localized additional illumination (e.g., at an injection site, etc.), through tissue illumination, a projected pattern or grid, cross projections, or any combination thereof for use by the image capture device in capturing the images. For example, non-contact sensor 164b may include a camera as described in International Patent Application No. PCT/US2020/061733, filed Nov. 23, 2020, the content of which is hereby incorporated by reference in its entirety. Non-contact sensor 164b may continue two or more cameras to provide binocular or 3D vision, which may enable 3D determination of phenomena such as swelling, gross motion in 3D, or vibrations or small motions in 3D.

In some non-limiting embodiments or aspects, non-contact sensor 164b may be mounted on imager 158, on injector 152, on a bed of a patient, on a pedestal pole, on an adjustable, overhead counterpoise, on a ceiling, and/or the like. In some non-limiting embodiments or aspects, non-contact sensor 164b may be held by a patient during a fluid injection (e.g., a contrast media injection, etc.) and/or an imaging examination. In some non-limiting embodiments or aspects, non-contact sensor 164b may be remotely controlled by a user (e.g., via user device 108, etc.) to pan and zoom to a desired field of view. In some non-limiting embodiments or aspects, sensor system 106 may control non-contact sensor 164b using one or more object tracking techniques to automatically follow an extremity (e.g., an arm, a leg, a hand, a foot, etc.) of a patient including an injection site.

In some non-limiting embodiments or aspects, fluid injection system 102, imaging system 104, user device 108, and/or auxiliary system 112 may include one or more additional sensors (e.g., contact sensors 164a, non-contact sensors 164b, etc.) configured to determine sensor data associated with a patient and/or a fluid injection (e.g., a contrast media injection, etc.) for the patient and/or store and/or provide sensor data determined by one or more additional sensors configured to determine sensor data associated with a patient and/or a fluid injection for the patient. Exemplary sensors may include respiration bands and/or ECG electrodes to enable injection and/or image acquisition in relation to a patient's respiration and/or heartbeat, respectively.

Figure 4B:
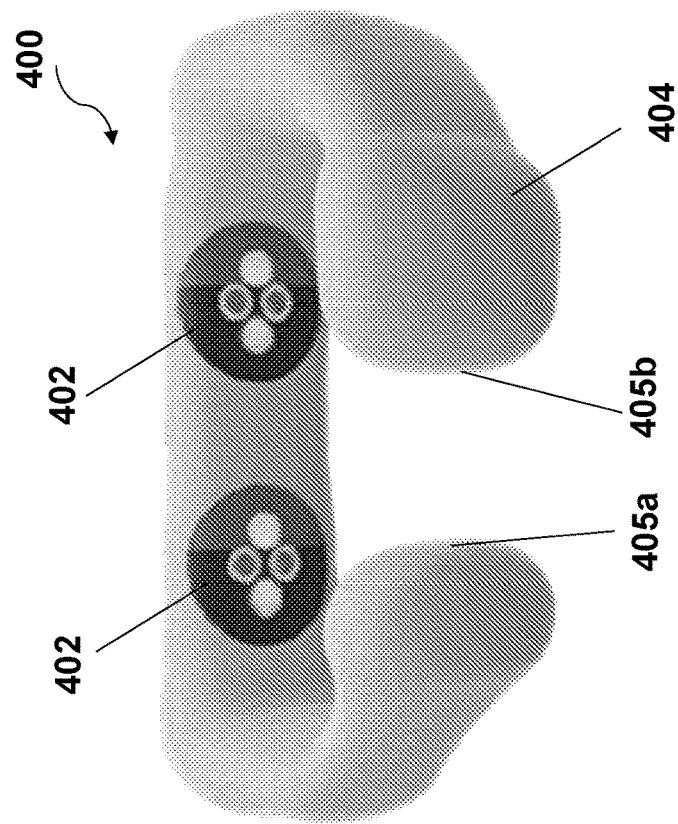
FIGS. 4A and 4B are perspective views of non-limiting embodiments or aspects of a contact sensor device.
Figure 4A:
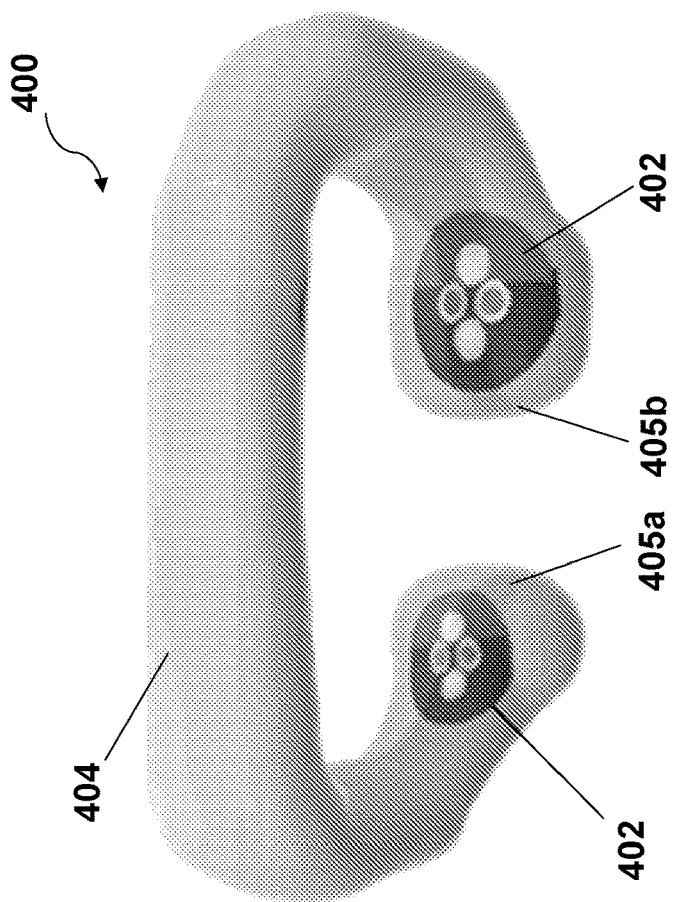
Figure 4C:
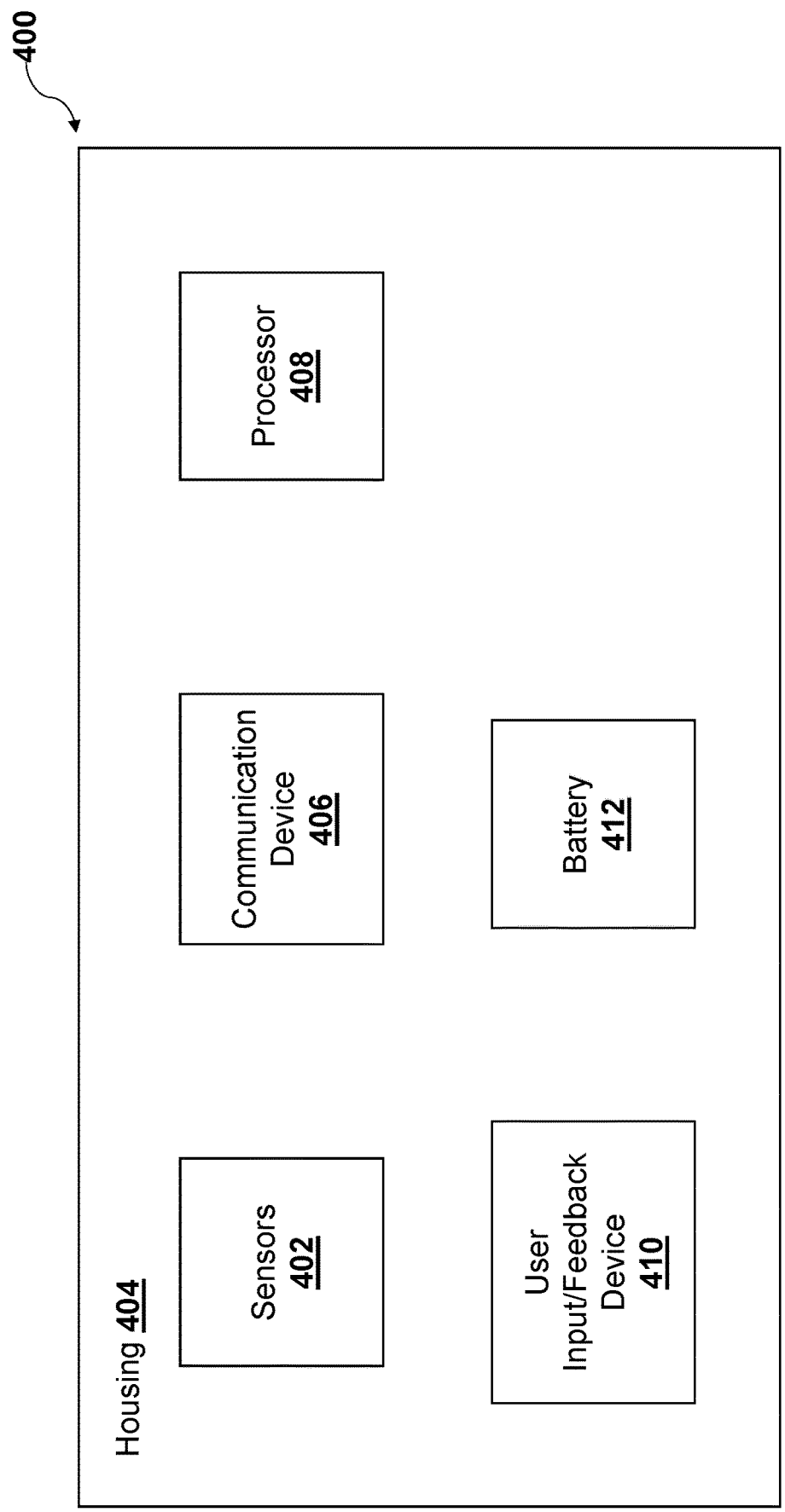
FIG. 4C is a diagram of non-limiting embodiments or aspects of components of a contact sensor device.
Figure 4D:
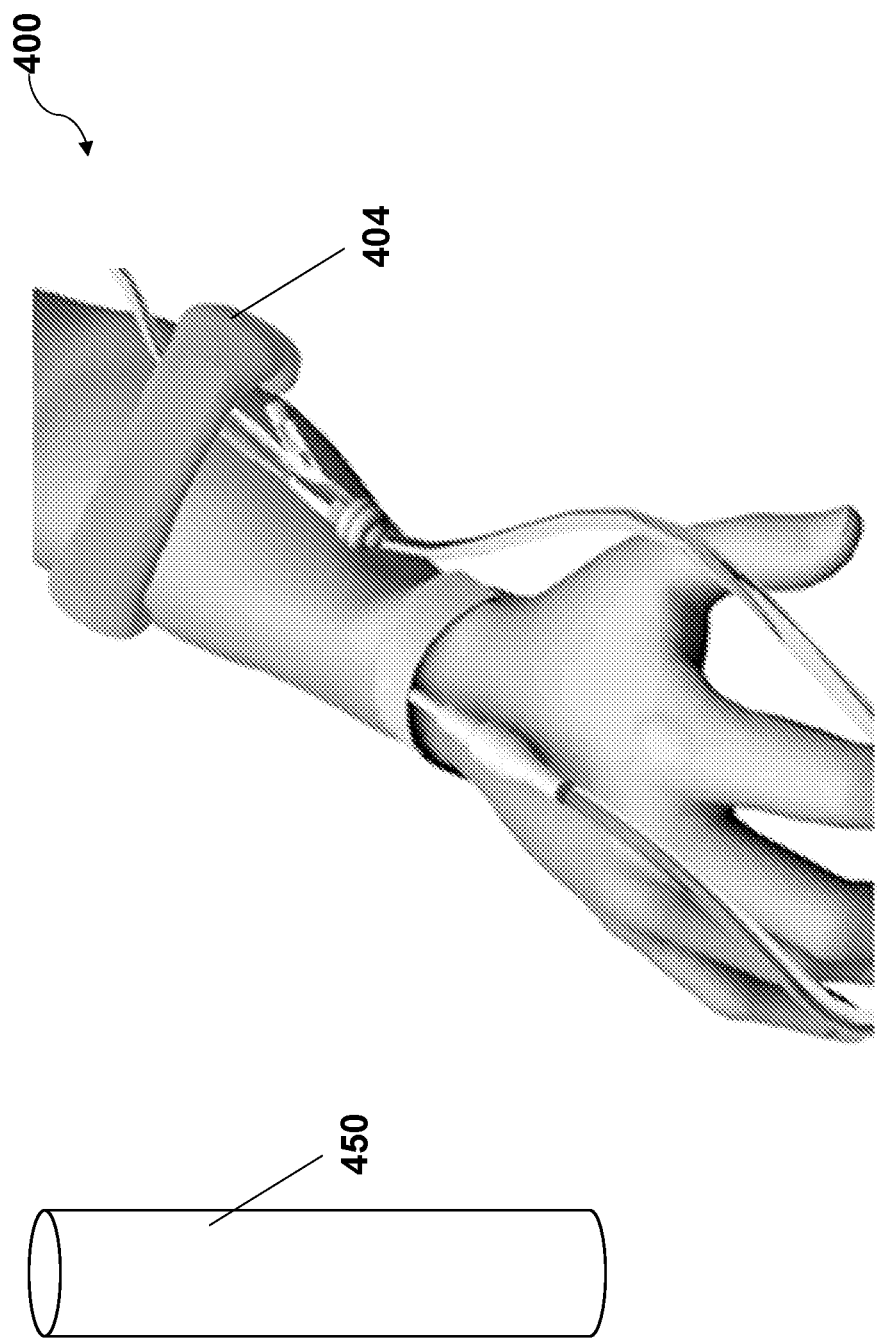
FIG. 4D is a perspective view of non-limiting embodiments or aspects of a contact sensor device attached to an extremity of a patient.

Referring now to FIGS. 4A and 4B, FIGS. 4A and 4B are perspective views of non-limiting embodiments or aspects of contact sensor device 400. Sensor system 106 may include contact sensor device 400 and/or contact sensor device 400 may include at least one contact sensor 402 of contact sensors 164a of sensor system 106 that are configured to determine sensor data associated with a patient and/or a fluid injection for the patient. Referring also to FIG. 4C, contact sensor device 400 may include housing 404 that houses contact sensors 402, communication device 406, processor 408, user input/feedback device 410, and/or battery 412. Housing 404 may provide a waterproof seal between an interior of housing 404 including contact sensors 402, communication device 406, processor 408, user input/feedback device 410, and/or battery 412 and an exterior of housing 404 such that contact sensors 402, communication device 406, processor 408, user input/feedback device 410, and/or battery 412 and/or electronic components thereof are sealed from an external environment surrounding contact sensor device 400 and/or such that contact sensor device 400 may be easily disinfected and eligible for multi-patient use. Housing 404 may have an elongated shape that extends between first end 405a and second end 405b. For example, as shown in FIG. 4D, housing 404 may include a bracelet-shaped wearable for a patient configured to be attached proximally to an injection site on an extremity (e.g., an arm, a leg, etc.) of a patient to measure sensor data associated with the patient data before, during, and/or after a fluid injection and/or an examination (e.g., an MRI exam, a CT exam, etc.). As an example, housing 404 may include a flexible exterior or frame (e.g., an antibacterial silicone exterior or frame, etc.), which is configured to flex or bend to surround an extremity of a patient, and which houses internally contact sensors 402, communication device 406, processor 408, user input/feedback device 410, and/or battery 412 and/or electronic components thereof, and fluidically seals the internal components of contact sensor device 400 from an external environment. As an example, housing 404 may include an elastic member(s), for example, metal, plastic or foam, which urges the sensor(s) against the skin with an appropriate force or pressure. The elastic members may also urge the housing into a shape that assists in gripping an extremity of the patient.

In some non-limiting embodiments or aspects, as shown in FIG. 4D, contact sensor device 400 may include a removable strip or sheath 450 configured to surround, cover or separate housing 404 from skin contact to protect contact sensor device 400 from cross contamination (e.g., from patient to patient or via hands of a technologist, etc.). In some non-limiting embodiments or aspects, contact sensor device 400 may be a disposable or single-use device including printed sensors 402 and on a printed sensor pad or housing 404 that may adhere (e.g., via an adhesive layer, etc.) to the skin of the patient adjacent to an injection site.

In some non-limiting embodiments or aspects, housing 404 may be configured to immobilize an extremity (e.g., an arm, etc.) of the patient by preventing or restricting the patient from bending the extremity and thereby constricting a vein and/or a catheter or dislodging the catheter from the vein. For example, housing 404 may be configured as an elbow brace or exoskeleton. As an example, housing 404 may also immobilize the injection site to facilitate observation of the injection site by non-contact sensor(s) 164b.

In some non-limiting embodiments or aspects, housing 404 may include removable and/or disposable attachment means, such as a flexible patch, a fabric strip, an adhesive connector, a mechanical latch, a blood pressure cuff, a hook and loop fastener, such as a Velcro®-type attachment, and/or a suction cup. For example, contact sensor device 400 may be configured to attach to a dressing, such as the BD Tegaderm™ Transparent Film Dressing via physical alignment indicia, to another device (e.g., injector 152, imager 158, a disposable dressing, etc.), and/or to the patient. As an example, housing 404 may have a cylinder or hockey puck shape including an adhesive connected to attach housing 404 to the patient. In some non-limiting embodiments or aspects, housing 404 may include a clear disposable band to enable a user to visually inspect skin of a patient adjacent an injection site. Depending upon a shape or shapes of various segments of housing 404, an attachment mechanism configured to urge housing 404 and/or contact sensor(s) 164a into proper contact with a patient to may include: double sided adhesive tapes compatible with skin, a disposable strap or band; a strap with a disposable isolation patch or element (which may be especially useful for patients with arms with significant hair); a wrap that is inflated to a desired non-occlusive pressure similar to a blood pressure cuff; elastic force as in a "slap" bracelet; an elastomeric band or bracelet which may optionally be disposable and/or clear to allow for visual inspection of skin near injection site; and/or attachment to a Tegaderm™ or similar existing device on a patient arm via physical indicia on the existing device. Additionally, or alternatively, housing 404 and/or contact sensor(s) 164a may not be mechanically attached to the patient but may be held in contact with the patient by having the patient lay on housing 404 and/or contact sensor(s) 164a or place his/her arm on housing 404 and/or contact sensor(s) 164a. Housing 404 and/or contact sensor(s) 164a may also be laid loosely onto the patient. In these cases, gravity and/or the effort to of the patient may hold housing 404 and/or contact sensor(s) 164a in contact with the patient.

Sterility and/or cross contamination concerns are relatively low for non-contact sensor 164b because non-contact sensor 164b need not contact the patient. One or more of the following approaches may provide sufficient sterility and/or cross contamination prevention aspects for contact sensor device 400 and/or contact sensor 164a: a disposable attachment barrier; a cleaning of contacting aspects (e.g., electrodes, housing 404, etc.) of contact sensor device 400 and/or contact sensor 164a with a disinfecting wipe or spray; a "home base" or mount for holding and optionally for storing and/or charging contact sensor device 400 and/or contact sensor 164a between patients, which may also include a sterilizing device, for example UV lamp, ozone treatment, or disinfecting wipe station; inclusion of self-sterilizing surfaces, for example a silver nano-particle surface or film; a sheath into which contact sensor device 400 and/or contact sensor 164a may be slipped before use; an interposed, disposable barrier layer placed between the patient skin and contact sensor device 400 and/or contact sensor 164a; and/or some or all of contact sensor device 400 and/or contact sensor 164a may be sufficiently low cost that at least one segment or portion thereof may be used once for a patient and be thrown away or given to the patient as a "freebie" for their subsequent medical or home/personal use.

The giving away of an at least one segment or portion of contact sensor device 400 and/or contact sensor 164a may be a good "marketing" and patient satisfaction activity or action. The application described herein in connection with patient information, education, electronic consenting, and similar functions may be configured to interface with the freebie segment or portion and enable the segment or portion to be a personal pulse oximeter and/or skin contact thermometer, for example.

Communication device 406 may include a wired and/or wireless communication device configured to communicate to an external device and/or system (e.g., fluid injection system 102, imaging system 104, sensor system 106, user device 108, management system 110, auxiliary system 112, etc.) sensor data associated with a patient.

Processor 408 may be programmed and/or configured to control one or more operations of contact sensors 402 and/or to determine sensor data associated with a patient. In some non-limiting embodiments or aspects, processor 408 may include a low power microcontroller unit (MCU).

User input/feedback device 410 may be configured to receive a user input from a user and/or to provide feedback to the user. For example, user input/feedback device 410 may include at least one of the following: a display, a light-emitting diode (LED), an audio output device (e.g., a buzzer, a speaker, a headset, etc.), a haptic output device (e.g., a vibrator, etc.) or any combination thereof. As an example, a user may establish communications with (e.g., pair, etc.) contact sensor device 400 with an external device and/or system via user input/feedback device 410 and/or provide prompts and/or instructions, which may be received from the external device and/or system, to a patient via user input/feedback device 410. In some non-limiting embodiments or aspects, user input/feedback device 410 may function as a patient call button configured to automatically call a user outside the scan room in response to being actuated.

User input/feedback device 410 may be partitioned between various pieces of hardware. For example, some input and/or output features or functions may be realized on contact sensor device 400. Some of the same and/or other functions may be accessible through a separate, purpose built, specific use user input/feedback device 410. Some of the same or other functions may be accessible through a general or multipurpose user input/feedback device 410, for example an iPhone. Some of the same and/or other functions may be accessible through a user interface of other equipment associated with a study or procedure being performed, for example injector interface 156 and/or imager user interface 162. Battery 412 may include a rechargeable battery (e.g., a battery rechargeable via an inductive charging technique, etc.), a single use battery, a replaceable battery, a wired connection to an external battery and/or power source, or any combination thereof. Battery 412 may provide power for operating components of contact sensor device 400.

Figure 4E:
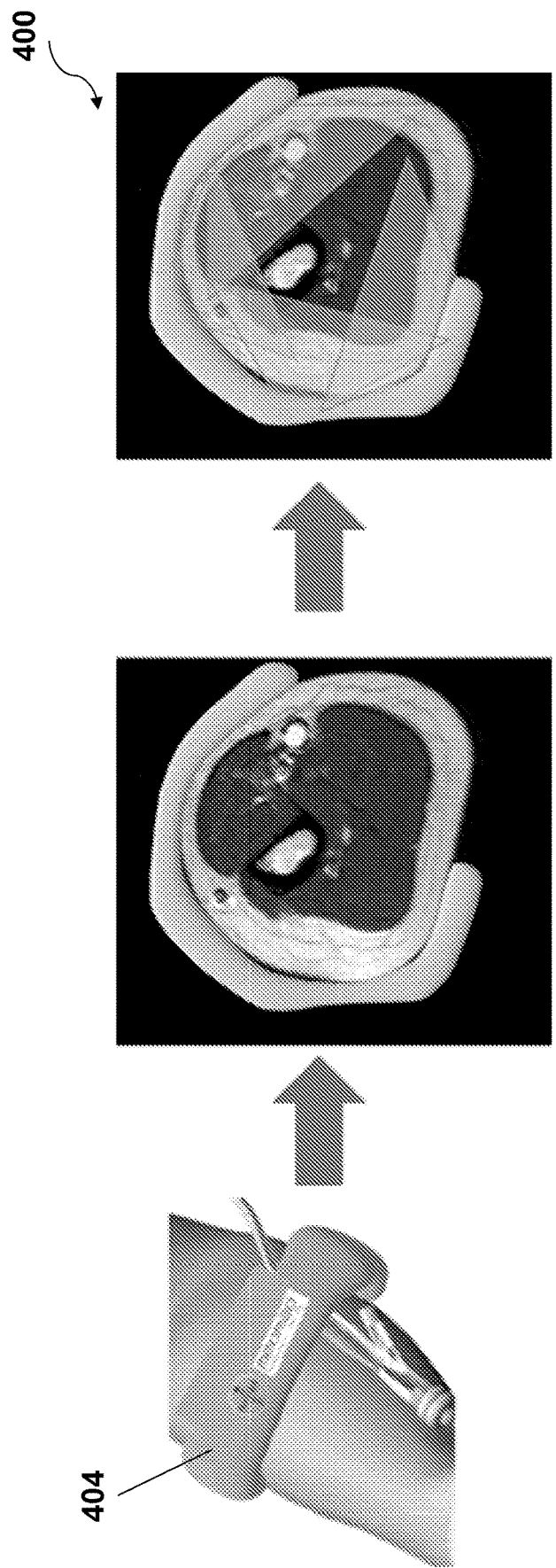
FIG. 4E is a cross sectional view of non-limiting embodiments or aspects of a contact sensor device attached to an extremity of a patient.

Still referring to FIGS. 4A-4D, and referring also to FIG. 4E, contact sensors 402 may be orientated in a pattern, for example, circumferentially around an extremity of a patient when contact sensor device 400 is attached to the extremity of the patient such that contact sensors 402 may measure sensor data including tissue parameters and/or the like in a transversal cross-section of the extremity of the patient. For example, contact sensors 402 may be spaced apart from each other along a length of housing 404 extending from first end 405a to second end 405b. Contact sensor 402 sensing modes may include transmissive, reflective, absorptive, listen or passively measure modes. Different modes may be used for different sensors. Multiple and/or hybrid modes may be used depending up ambient and/or patient conditions. Phase gated sensing (e.g., phase locked loops (PLL), etc.), synchronous sensing, and/or other existing sensing means may be used for noise/interference reduction and/or ambient signal cancellation. A signal sensed may be a narrow segment of a possible spectrum and/or a broad segment of a possible spectrum to which subsequent processing may be applied.

Referring now to FIGS. 8A-8E, FIGS. 8A-8E are perspective views of non-limiting embodiments or aspects of contact sensor device 800. Sensor system 106 may include contact sensor device 800 and/or contact sensor device 800 may include at least one contact sensor (e.g., 804, 808, 810, etc.) of the one or more contact sensors 164a of sensor system 106 that are configured to determine sensor data associated with a patient and/or a fluid injection (e.g., a contrast media injection, etc.) for the patient. In some non-limiting embodiments or aspects, sensor system 106 may include contact sensor device 400 and contact sensor device 800, one of contact sensor device 400 and contact sensor device 800, or neither contact sensor device 400 nor contact sensor device 800. Further, contact sensor device 400 can be implemented within contact sensor device 800 (or vice-versa), and/or contact sensor device 400 can perform one or more functions as described as being performed by contact sensor device 800 (or vice-versa).

Contact sensor device 800 may include housing 802 and finger sensor 804 (e.g., a pulse oximeter, etc.). Finger sensor 804 may be connected to housing 802 via wire 806. Housing 802 may include electronic components 808, conductivity probes or electrodes 810, and/or disposable adhesive protector 812. Electronic components 808 may include contact sensors 164a, a processor, a memory, a wired and/or wireless communication device, a user input/feedback device, and/or a battery. For example, electronic components 808 of contact sensor device 800 may be the same as or similar to components of contact sensor device 400 described herein with respect to FIG. 4C.

Figure 8A:
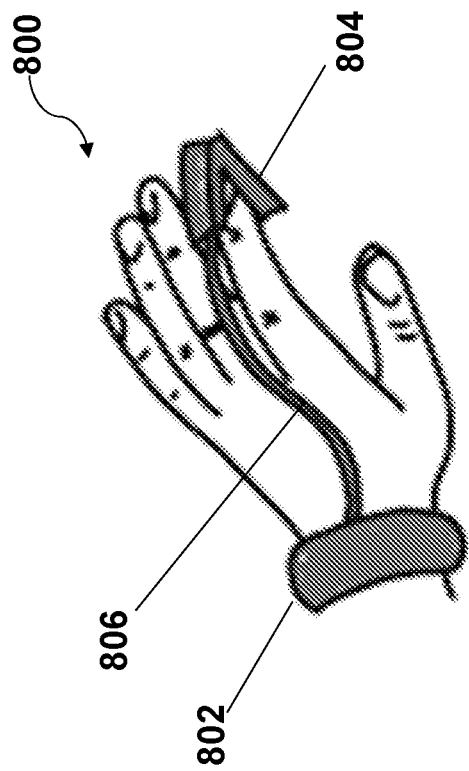
FIGS. 8A-8E are perspective views of non-limiting embodiments or aspects of a contact sensor device.
Figure 8B:
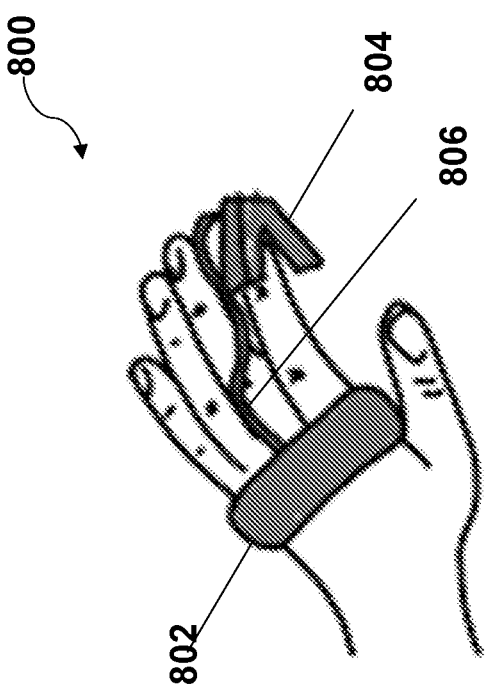
Figure 8D:
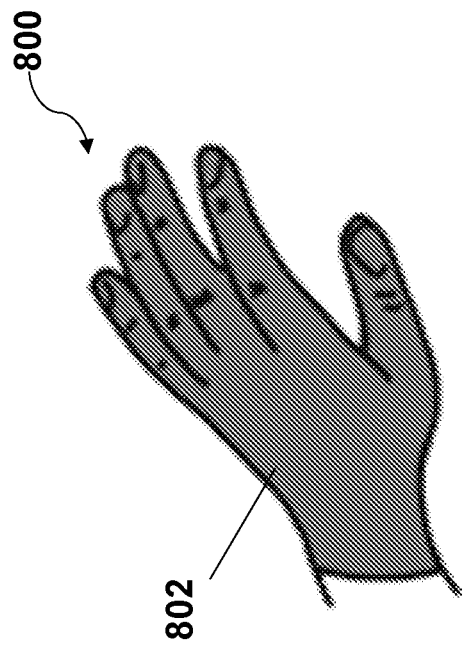
Figure 8C:
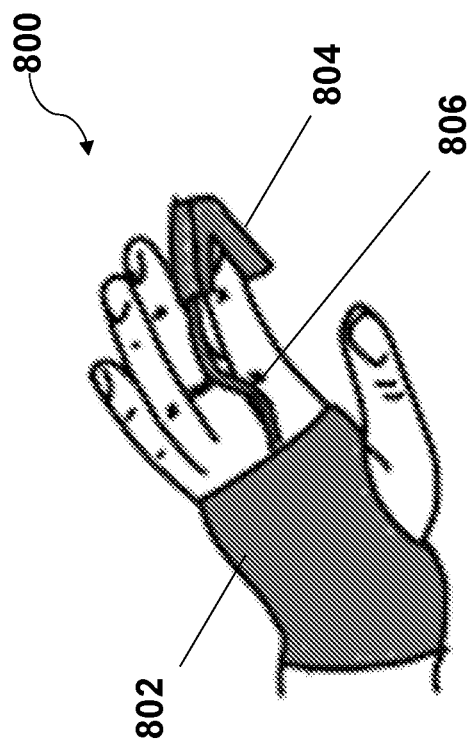
Figure 8E:
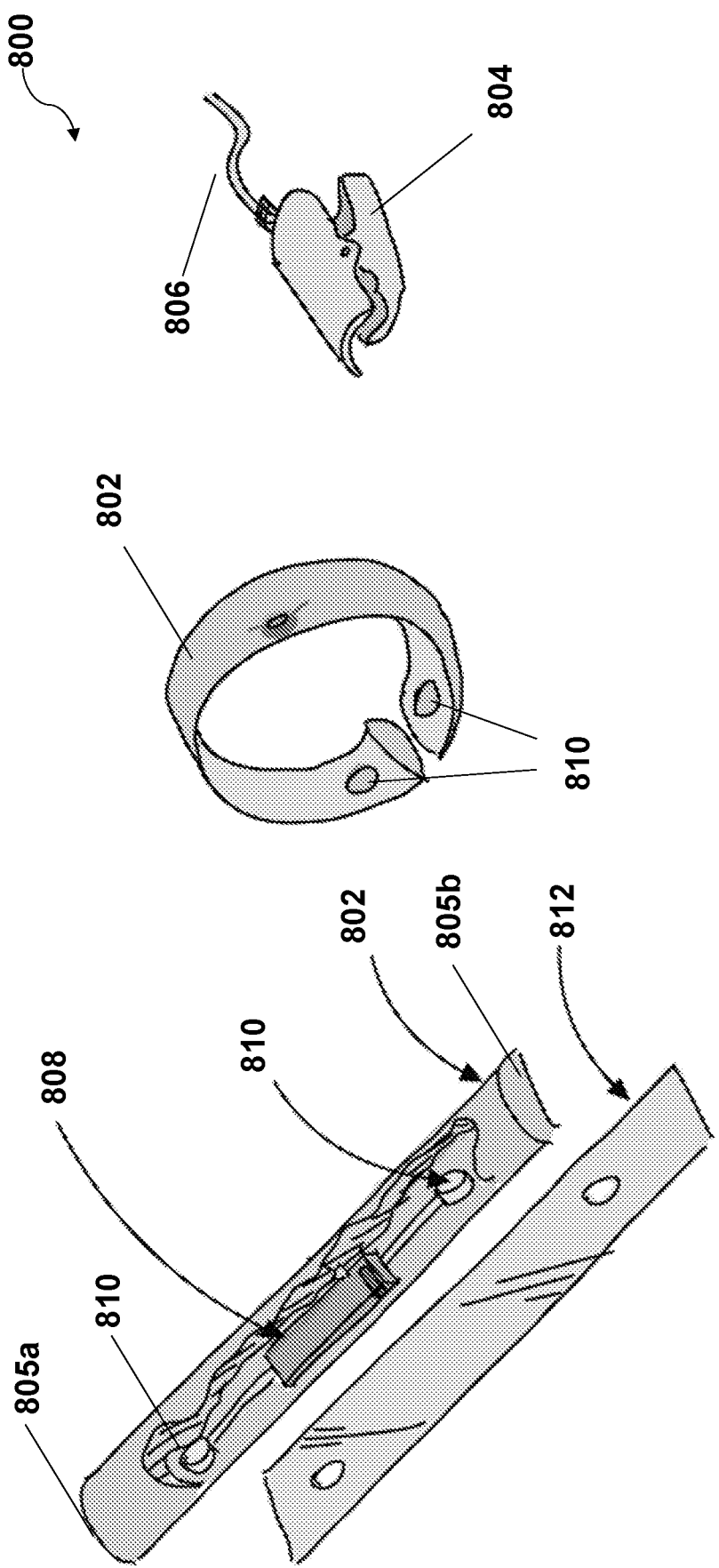

Housing 802 may include a soft, molded strap (e.g., a plastic strap, etc.) over molded onto a stiffener (e.g., a bendable wire, a semi-flexible metal frame, etc.). In some non-limiting embodiments or aspects, housing 802 may extend between first end 805a and second end 805b and be configured to wrap around a palm and/or a wrist of patient. For example, as shown in FIG. 8A, housing 802 may be configured to wrap around a middle of a palm of a patient with finger sensor 804 connected to housing 802 via wire 806. For example, as shown in FIG. 8B, housing 802 may be configured to wrap around a wrist of a patient with finger sensor 804 connected to housing 802 via wire 806. For example, as shown in FIG. 8C, housing 802 may be configured to wrap around a palm and a wrist of a patient with finger sensor 804 connected to housing 802 via wire 806. In some non-limiting embodiment or aspects, first end 805a of housing 802 may be configured to connect to second end 805b of housing 802 via a connection mechanism (e.g., a strap, a Velcro fastener, a button, etc.) In some non-limiting embodiments or aspects, housing 802 may include a glove configured to be worn on a hand of a patient such that housing 802 fully covers the hand and wrist of the patient as shown in FIG. 8D, which enables finger sensor 804 to be connected to housing 802 without the use of an exposed wire.

Conductivity probes or electrodes 810 may provide a direct conductive contact with skin of a patient, for example, for a skin resistance sensor configured to detect a skin resistivity of a patient. Tissue electrical properties may be measured with a direct current and/or an alternating current, including various RF and microwave frequencies up to and including visible light.

Disposable adhesive protector 812 may include a disposable film configured to reduce or eliminate direct contact of housing 802 with a patient. For example, disposable adhesive protector 812 may include a sheet (e.g., a plastic sheet, a vinyl sheet, a latex sheet, a paper sheet, etc.) including a first side configured to directly contact a patient and a second side including an adhesive configured to adhere disposable adhesive protector 812 to a side of housing 802 that faces the patient when contact sensor device 800 is worn by the patient. In such an arrangement, disposable adhesive protector 812 may include openings sized and shaped to enable conductivity probes or electrodes 810 to directly contact the skin of the patient through disposable adhesive protector 812, or adhesive protector 812 may contain segments of conductive material to make or enhance contact between the skin and contact sensor device 800.

Selected aspects of contact sensors 400, 800 may be disposable or single use and other aspects may be reusable or multi-use depending upon an approach taken to cross contamination reduction and prevention and/or the cost of various aspects. This may include a spectrum of options. At one end the spectrum, contact sensors 400, 800 may be totally multi-use and, for example, being decontaminated by spraying, wiping, or immersing in a cleaning solution or having a surface that kills any biological active entities and/or catalyzes the destruction of contaminating chemicals to, on the other end of the spectrum of options, the sensors 400, 800 being fully single use and being thrown out or given to the patient to take home and use elsewhere as their wellbeing and healthcare needs may find useful. Intermediate aspects or embodiments on this spectrum of multi-usability may prove a single use, single layer material between the contact surface and the skin; may envelop the sensor in a single use sheath (e.g., sheath 450, etc.); may involve some sensors or aspects of the sensor be single use, for example a thermistor or the photo diodes and photo transistor of a pulse oximeter, while the electronics that read the sensors are reusable; may provide for all the sensors and material contacting the skin to be single use while the data processor, batteries, and communication parts of contact sensors 400, 800 may be reusable.

Referring again to FIGS. 1A and 1B, user device 108 may include one or more devices capable of receiving information and/or data from fluid injection system 102, imaging system 104, sensor system 106, management system 110, and/or auxiliary system 112 (e.g., via communication network 114, etc.) and/or communicating information and/or data to fluid injection system 102, imaging system 104, sensor system 106, management system 110, and/or auxiliary system 112 (e.g., via communication network 114, etc.). For example, user device 108 may include one or more computing systems including one or more processors (e.g., one or more computing devices, one or more server computers, one or more mobile computing devices, one or more tablet computers, one or more mobile phones, etc.). In some non-limiting embodiments or aspects, user device 108 may include at least one of the following: injector user interface 156, imager user interface 162, management user interface 172, or any combination thereof.

User device 108 may take on various forms, be called various names, and/or be performed by various specific devices or systems depending upon the user(s) involved and the healthcare environment/system in which it is being used. For example, user device 108 may be a patient device, a patient portal or a patient care portal into which a patient enters information, signs in for a medical appointment or procedure, provides electronic consent, and/or receives information/training/support/comfort about any procedure which is to happen or answers to any questions about a future or past procedure. User device 108 may include the user's personal phone, tablet, and/or computer which may be running an application or accessing a web base service to provide functions of non-limiting embodiments or aspects described herein. User device 108 may be a part of a patient care portal provided by the patient's health provider or insurer. User device 108 may be a physician device 108 or physician portal 108 which provides patient data and/or adverse event risk assessment. User device 108 may be specifically associated with one or more of the other devices in this system, for example the fluid injector system 102, the imaging system 104, or the sensor system 106. Additionally, or alternatively, user device 108 may be physically located where it is most advantageous for the user performing a specific function or using a specific output or system aspect. For example, the patient may be using the patient portal (e.g., user device 108) to be entering data or receiving information in their referring or prescribing physician office or location, in their home, in a waiting area, or even in a public place such as a restaurant or parking lot. For example, a patient or caregiver may be accessing user device 108 wherever it is convenient for them to do so and functionally enabled by a specific implementation of the system. For example, a radiologist may, for example, access user device 108 in their office, in a preparation room, in the imaging suite, or in a reading room. For example, a technologist may access user device 108 through an aspect of fluid injection system 102, sensor system 106, and/or imaging system 104.

Management system 110 may include one or more devices capable of receiving information and/or data from fluid injection system 102, imaging system 104, sensor system 106, user device 108, and/or auxiliary system 112 (e.g., via communication network 114, etc.) and/or communicating information and/or data to fluid injection system 102, imaging system 104, sensor system 106, user device 108, and/or auxiliary system 112 (e.g., via communication network 114, etc.). For example, management system 110 may include one or more computing systems including one or more processors (e.g., one or more computing devices, one or more server computers, one or more mobile computing devices, etc.). As an example, management system 110 may include management control and computation system 166 and/or management user interface 172. In some non-limiting embodiments or aspects, management system 110 may be implemented within fluid injection system 102, imaging system 104, sensor system 106, user device 108, and/or auxiliary system 112 (where auxiliary system 112 may or may not be associated with fluid injection system 102 and/or imaging system 104).

Auxiliary system 112 may include one or more devices capable of receiving information and/or data from fluid injection system 102, imaging system 104, sensor system 106, user device 108, and/or management system 110 (e.g., via communication network 114, etc.) and/or communicating information and/or data to fluid injection system 102, imaging system 104, sensor system 106, user device 108, and/or management system 110 (e.g., via communication network 114, etc.). For example, auxiliary system 112 may include one or more computing systems including one or more processors (e.g., one or more computing devices, one or more server computers, one or more mobile computing devices, etc.). As an example, auxiliary system 112 may include hospital information system(s) (HIS) 168, cloud computing and offsite resources 170, electronic medical records (EMR), a radiology information system(s) (RIS), a modality worklist (MWL), a patient portal to a healthcare system, a telemedicine portal, a picture archiving and communication system(s) (PACS), a laboratory information system(s) (LIS), an injection system(s) (e.g., fluid injection system 102, etc.), an imaging system(s) (e.g., imaging system 104, etc.), a smart phone, a tablet computer, or any combination thereof.

Communication network 114 may include one or more wired and/or wireless networks. For example, communication network 114 may include a cellular network (e.g., a long-term evolution (LTE) network, a third generation (3G) network, a fourth generation (4G) network, a fifth generation (5G) network, a code division multiple access (CDMA) network, etc.), a short range wireless communication network (e.g., a Bluetooth network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of these or other types of networks.

The number and arrangement of systems and devices shown in FIGS. 1A and 1B are provided as an example. There can be additional systems and/or devices, fewer systems and/or devices, different systems and/or devices, or differently arranged systems and/or devices than those shown in FIGS. 1A and 1B. Furthermore, two or more systems or devices shown in FIGS. 1A and 1B can be implemented within a single system or a single device, or a single system or a single device shown in FIGS. 1A and 1B can be implemented as multiple, distributed systems or devices. Additionally, or alternatively, a set of systems or a set of devices (e.g., one or more systems, one or more devices, etc.) of environment 100 and/or implementation 150 can perform one or more functions described as being performed by another set of systems or another set of devices of environment 100 and/or implementation 150.

Figure 2:
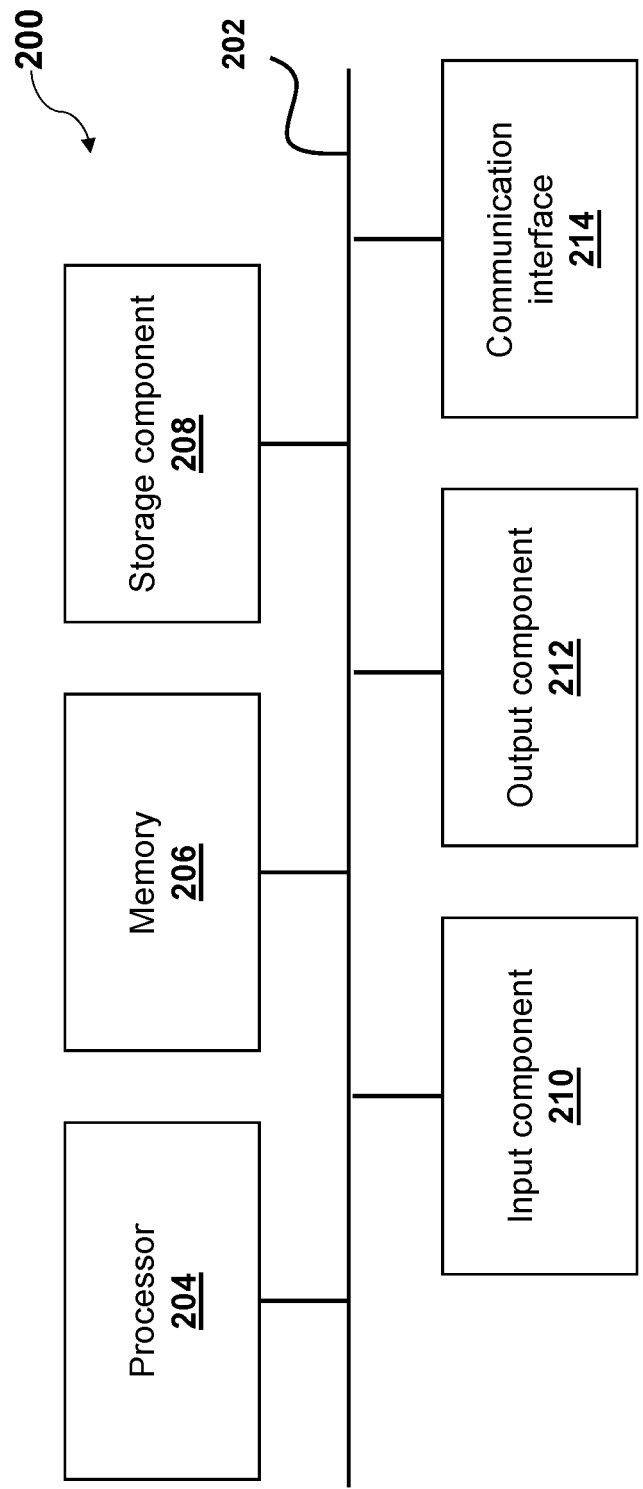
FIG. 2 is a diagram of non-limiting embodiments or aspects of components of one or more devices and/or one or more systems of FIGS. 1A and 1B.

Referring now to FIG. 2, FIG. 2 is a diagram of example components of a device 200. Device 200 may correspond to one or more devices of fluid injection system 102, one or more devices of imaging system 104, one or more devices of sensor system 106, user device 108 (e.g., one or more devices of a system of user device 108, etc.), one or more devices of management system 110, and/or one or more devices of auxiliary system 112. In some non-limiting embodiments or aspects, one or more devices of fluid injection system 102, one or more devices of imaging system 104, one or more devices of sensor system 106, user device 108 (e.g., one or more devices of a system of user device 108, etc.), one or more devices of management system 110, and/or one or more devices of auxiliary system 112 may include at least one device 200 and/or at least one component of device 200.

As shown in FIG. 2, device 200 may include bus 202, processor 204, memory 206, storage component 208, input component 210, output component 212, and/or communication interface 214.

Bus 202 may include a component that permits communication among the components of device 200. In some non-limiting embodiments or aspects, processor 204 may be implemented in hardware, software, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read-only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally or alternatively, input component 210 may include a sensor for sensing information (e.g., a global positioning system (GPS) component, an accelerometer, a gyroscope, an actuator, contact sensor 164a, non-contact sensor 164b, and/or any of the sensors described herein, etc.). Output component 212 may include a component that provides output information from device 200 (e.g., a display, a speaker, a tactile or haptic output, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a WiFi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database, etc.). Device 200 may be capable of receiving information from, storing information in, communicating information to, or searching information stored in the data storage or one or more data structures in memory 206 and/or storage component 208.

The number and arrangement of components shown in FIG. 2 are provided as an example. In some non-limiting embodiments or aspects, device 200 may include additional components, fewer components, different components, or differently arranged components than those shown in FIG. 2. Additionally or alternatively, a set of components (e.g., one or more components) of device 200 may perform one or more functions described as being performed by another set of components of device 200.

Figure 3:
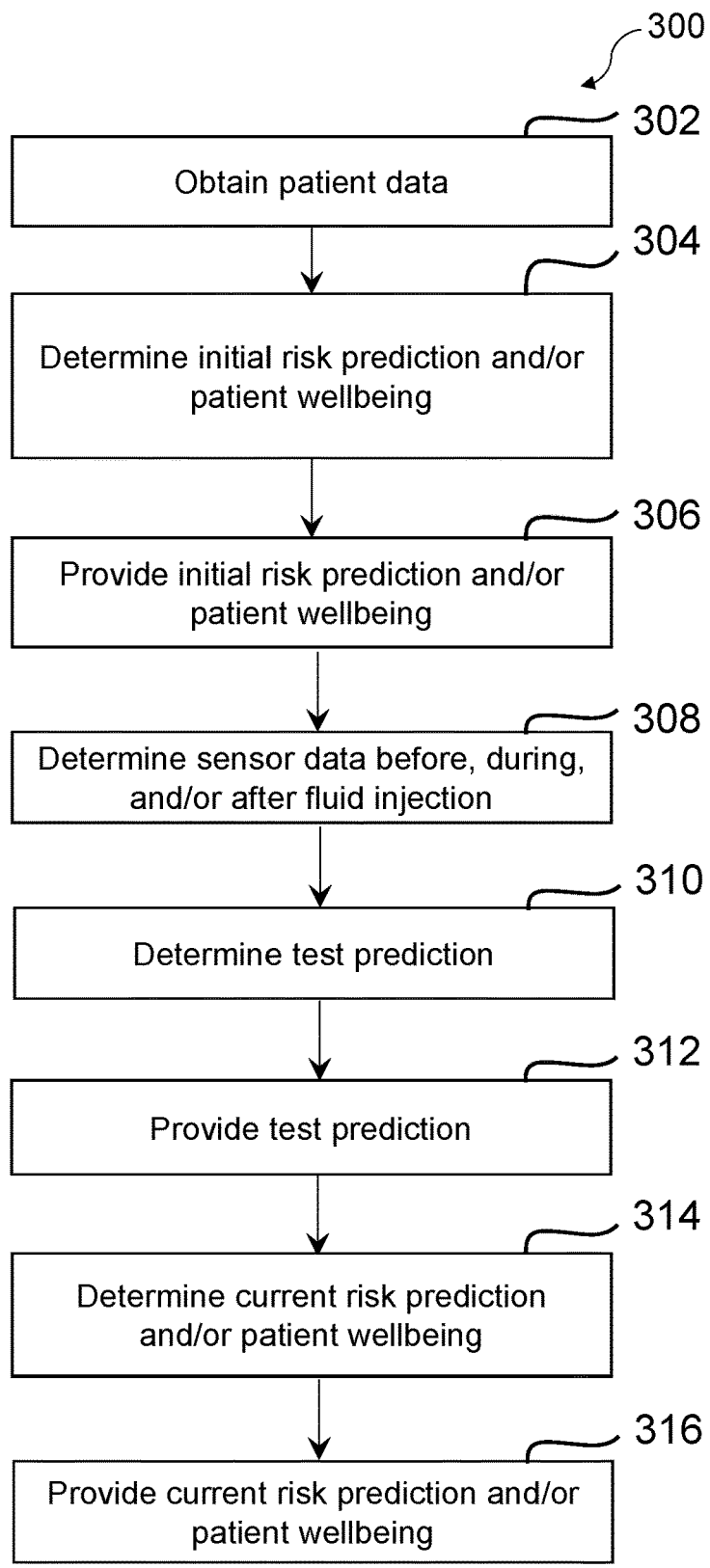
FIG. 3 is a flowchart of non-limiting embodiments or aspects of a process for safeguarding wellbeing of patients for fluid injection.

Referring now to FIG. 3, FIG. 3 is a flowchart of non-limiting embodiments or aspects of a process 300 for safeguarding wellbeing of patients for fluid injection. In some non-limiting embodiments or aspects, one or more of the steps of process 300 may be performed (e.g., completely, partially, etc.) by management system 110 (e.g., one or more devices of management system 110, etc.). In some non-limiting embodiments or aspects, one or more of the steps of process 300 may be performed (e.g., completely, partially, etc.) by a user or another device or a group of devices separate from or including management system 110, such as fluid injection system 102 (e.g., one or more devices of fluid injection system 102, etc.), imaging system 104 (e.g., one or more devices of imaging system 104, etc.), sensor system 106 (e.g., one or more devices of sensor system 106, etc.), user device 108 (e.g., one or more devices of a system of user device 108, etc.), and/or auxiliary system 112 (e.g., one or more devices of auxiliary system 108, etc.).

As shown in FIG. 3, at step 302, process 300 includes obtaining patient data. For example, management system 110 may obtain patient data associated with a patient. As an example, management system 110 may receive and/or retrieve patient data associated with a patient from at least one of the following: fluid injection system 102, imaging system 104, sensor system 106, user device 108, auxiliary system 112, or any combination thereof. Patient data may also be obtained directly from the patient by a human or by interaction with a user interface of management system 110 that may prompt a user and/or the patient for and record such data.

Patient data may include at least one of the following parameters associated with a patient: an age; a gender; a weight; a prior chemotherapy status, such as an adverse peripheral venous status due to long-term oncological treatment, and/or the like (e.g., a yes, a no, a number of cycles of chemotherapy received, etc.); an estimated glomerular filtration rate (eGFR) (e.g., an eGFR of less than 45 ml/min/ 1.73 m$^2$, etc.); a thyroid stimulating hormone (TSH) level; a Triiodothyronine (FT3) Thyroxine (FT4) ratio (FT3/FT4); an amount or level of an environmental influence (e.g., a regional iodine saturation or nutrition amount or level for a region or location associated with the patient, etc.); a prior reaction to a previous fluid injection status (e.g., a yes, a no, a level, etc.); an atopic disorder status (e.g., a yes, a no, a level, etc.); a medical status as it relates to existence of diabetes and/or hypertension, such as a diabetic nephropathy status, and/or the like (e.g., a yes, a no, a level, etc.); a congestive heart failure status (e.g., a yes, a no, a level, etc.); a hematocrit level; a known or suspected renal failure status (e.g., a yes, a no, a level, etc.); a malignancy status (e.g., a yes, a no, a level, etc.); an implanted device for a central venous access status (e.g., a yes, a no, a level, etc.); a type of a medication; a type of fluid media to be administered in a fluid injection; a type of a fluid injection and/or imaging exam; a flow rate associated with a fluid injection; a catheter gauge associated with a fluid injection; a total volume of fluid associated with a fluid injection; a pressure curve associated with a fluid injection, an injection site associated with a fluid injection; or any combination thereof. In some non-limiting embodiments or aspects, patient data may include sensor data determined before a fluid injection is administered to a patient and/or sensor data determined during and/or after one or more previous fluid injections previously administered to the patient.

In some non-limiting embodiments or aspects, management system 110 may provide and/or implement a patient care system or patient care portal that is accessible via an application (e.g., via user device 108, etc.), for example, as software on a personal device, a smart phone, a tablet computer and/or other computer, a web site, and/or a custom device which may be loaned or given to a patient. The patient care portal may promote the patient's wellbeing, primarily before the fluid delivery and imaging study by providing information to the patient and collecting information from the patient as described herein. The application may provide patient support for imaging procedure referrals, screening, preparation, access, education (e.g. videos and/or written/graphical materials, etc.), health information management, and/or patient feedback to providers on user experience. For example, the application may be used to consolidate and manage patient data, sensor data, and/or other information during the chain of patient care steps for a diagnostic imaging procedure, from an initial prescription for an imaging scan to tracking diagnostic outcomes for future reference. The application may promote mental wellbeing by providing the patient with relevant information to help the patient have a more successful and more positive diagnostic imaging experience. The application may make patient experience information more visible to the patient community, referring clinicians, provider networks, and/or others to improve diagnostic imaging procedures as well as to other aspects of management system 110, such as the risk assessment aspects of management system 110. The application may eliminate or substantially reduce a likelihood of missed appointments due to uninformed patients, cancelled appointments due to fear of the procedure, workflow delays while a patient fills out forms, a likelihood of poor imaging outcomes due to lack of adequate patient preparation or patient inability to accomplish certain task associated with a procedure, for example breathing at the correct times, and/or patient discomfort due to patient uncertainty or unfamiliarity with the normal aspects of the procedure. Accordingly, the patient care portal or system may provide healthcare community-based diagnostic imaging patient support, tie user experience to diagnostic imaging, link information together for the patient to help provide a better patient experience, improve patient referral and care to obtain improved diagnostic imaging experiences and outcomes, increase patient compliance and comfort, more efficiently utilize diagnostic imaging center resources, and/or improve diagnostic imaging quality.

Figure 13A:
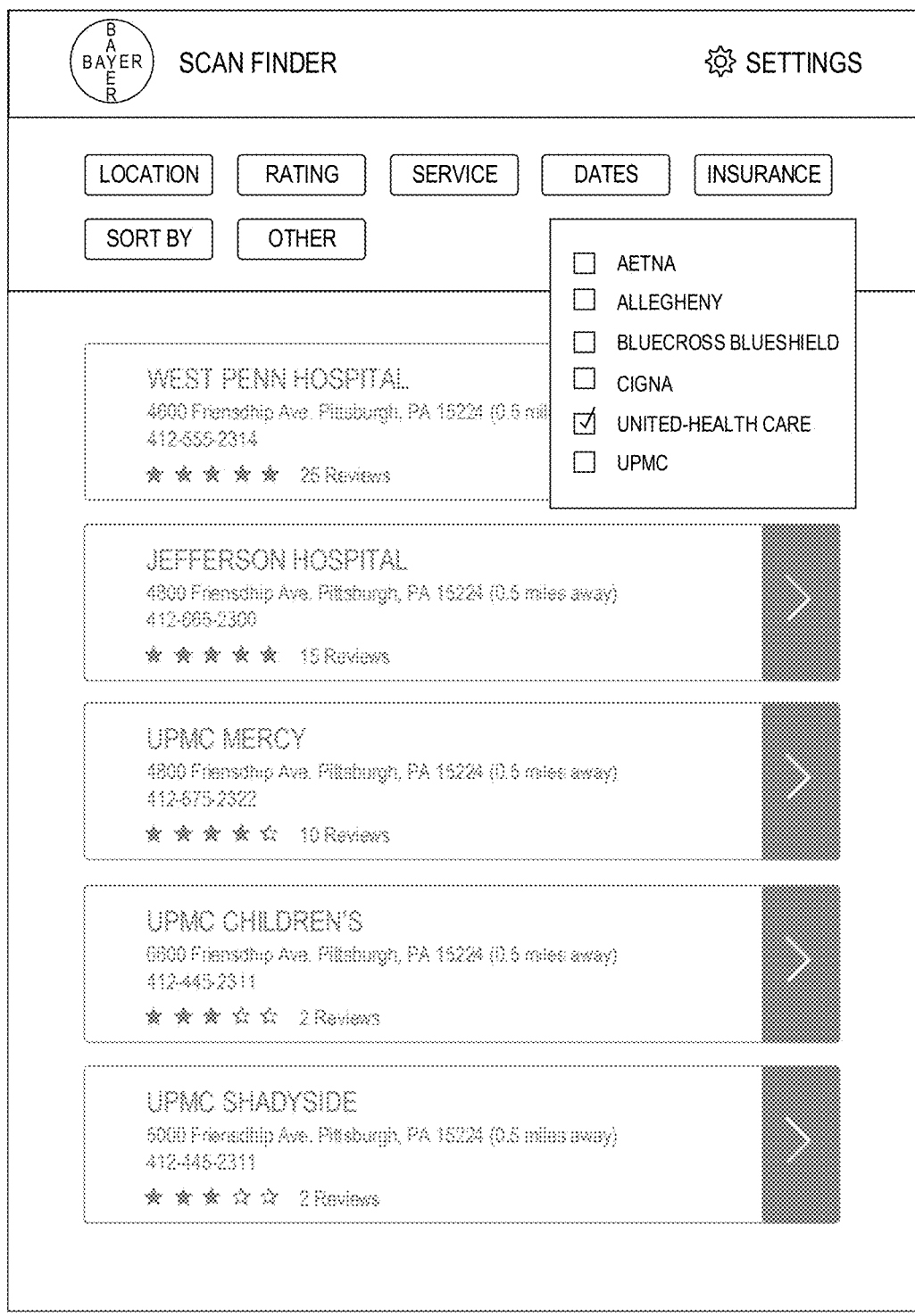
FIGS. 13A and 13B illustrate non-limiting embodiments or aspects of a patient portal application accessible via a user device.
Figure 13B:
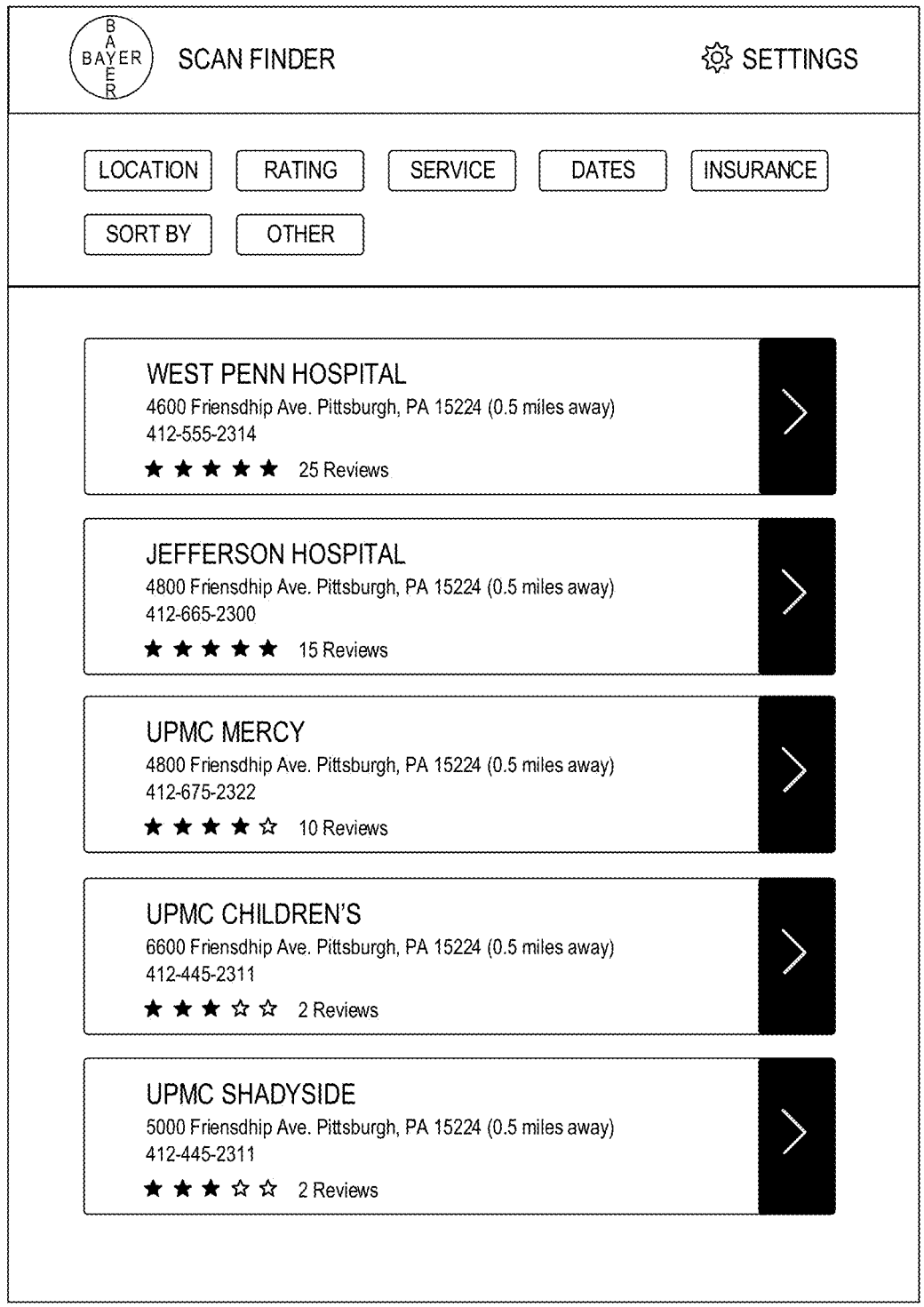

Management system 110 may obtain patient data and/or sensor data associated with a patient via the application for the patient care portal or system. The application may be accessible by a referring physician that prescribes an imaging scan to assist in scheduling the imaging scan for the patient. For example, FIGS. 13A and 13B show the application may apply one or more user selected filters and/or a weighted sum algorithm (e.g., a location of the patient, an insurance type of the patient, a type of scan prescribed, quality ratings, etc.) to a list of available imaging center locations to determine an imaging center location to recommend to the patient. The application may provide information to the patient to help the patient prepare for and learn about the imaging procedure experience. FIG. 14A shows the patient portal displayed on user device 108 enabling the patient to preconfigure imaging scan room options, such as ambiance or lighting, music, temperature, and/or the like before the imaging scan and/or provide additional patient data. This data may be automatically communicated to the imaging suite at the time of the patient's scan. FIG. 14B shows the patient portal displayed on user device 108 providing information (e.g., a video, etc.) of what the patient may expect the day of the scan. FIG. 14C shows the patient portal displayed on user device 108 providing a calendar notification and direction to the imaging scan location, which may improve patient comfort, wellbeing and/or satisfaction.

Figure 15A:
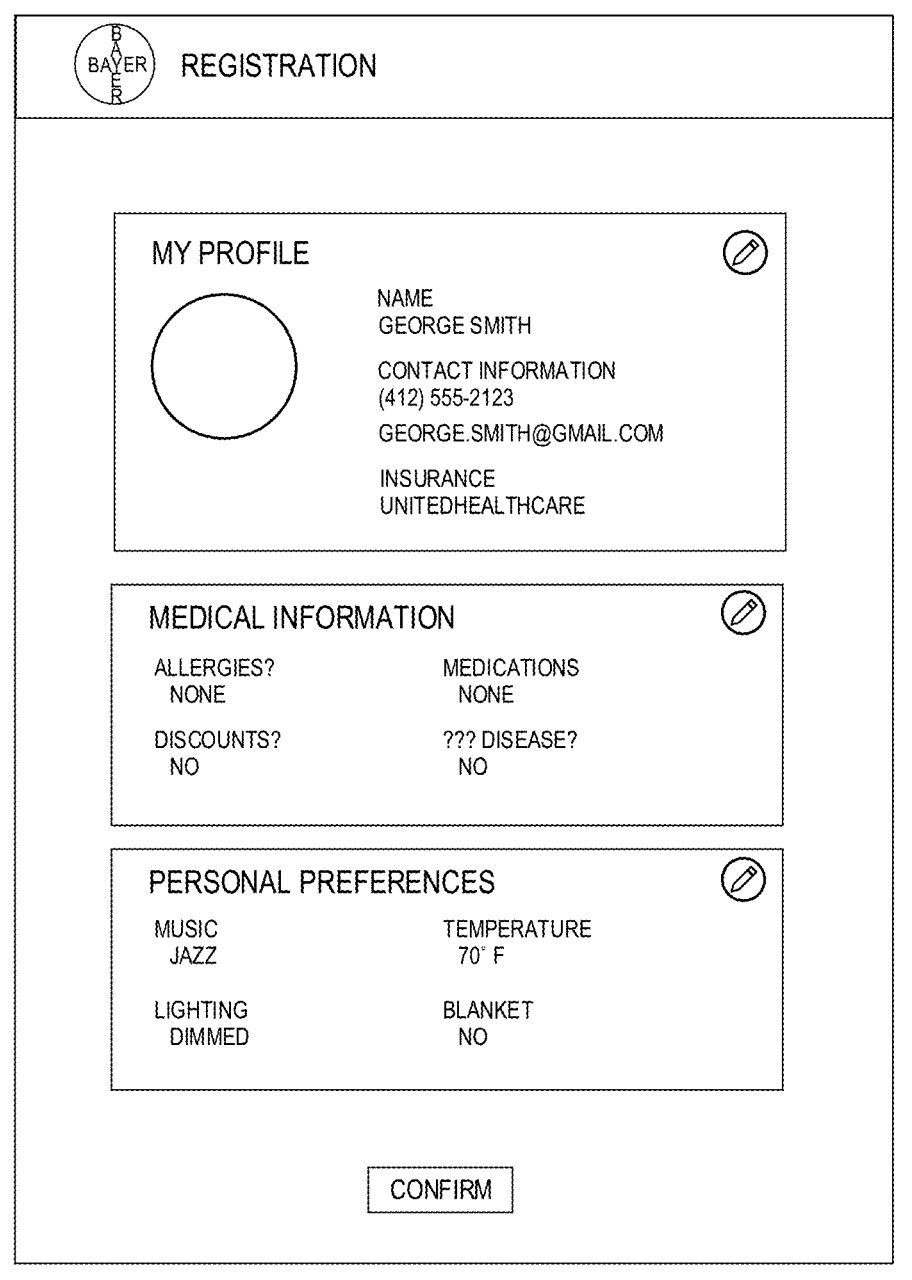

At a check-in for the imaging scan, patient data associated with the patient may be automatically synched or retrieved from auxiliary system 112 and/or the cloud and/or the patient portal via user device 108, thereby reducing an amount of time needed for the patient to check-in. As shown in FIG. 15A, management system 110 may automatically retrieve medical records and patient preferences before or during check-in and present the medical records and patient preferences to the patient via the application on user device 108 for faster confirmation of the correctness and completeness of the records and the patient's preferences. As shown in FIG. 15B, management system 110 may use the application to provide an automated and integrated consent process in which the patient electronically consents (e.g., on user device 108, etc.) to one or more procedures via the application, which may improve and/or increase a technologist's quality time with the patient.

After check-in, veins of the patient may be scanned by imaging system 104 (e.g., by one or more cameras of imaging system 104, etc.), and management system 110 may analyze and/or save the scanned images of the veins of the patient. A system such as that in U.S. Patent Application Publications 2004/0171923 A1 and/or 2008/0147147 A1, filed on Dec. 6, 2003 and Dec. 18, 2006, respectively, the entire contents of each of which is hereby incorporated by reference, may be used to assess a patient's veins and optionally facilitate access to the veins. For example, the patient data and vein analysis may be used to adjust or recommend adjustments or limits upon a fluid injection protocol and/or an imaging protocol for the patient, which may be presented to a user (e.g., a radiologist, etc.) via the application on user device 108 for approval or directly to the injector system 102 or the imaging system 104. Sensor system 106 (e.g., a smart bed sensor, a camera, contact sensor device 400 and/or 800, etc.) may continuously determine patient data, sensor data, and/or scan data associated with the patient, and management system 110 may adjust, based on the measured patient data, sensor data, and/or sensor data, the fluid injection protocol and/or the imaging protocol for the patient, which may be presented to a user (e.g., a radiologist, etc.) via the application on user device 108 for approval by the user. Or, said adjustment may be made automatically, within preselected limits. For example, a patient based dosage and a cardiac output of the patient enables a fluid injection protocol and scan duration to be adjusted for the patient.

Management system 110 may perform a scan image assessment of one or more of the medical images acquired by imaging system 104, which may be presented to a user (e.g., a radiologist, etc.) via the application on user device 108 for confirmation of the scan image assessment. For example, management system 110 may apply one or more artificial intelligence based image assessment tools to the scanned images of the patient to assess a quality of the scan and/or provide diagnostic recommendations. The medical scanned images and/or analysis thereof may be stored (e.g., in auxiliary system 112, in the cloud, etc.) for retrieval via the application by the radiology team and/or the patient.

Management system 110 may use the application to continuously monitor equipment and/or supplies and automatically order new equipment and/or supplies when an inventory level fails to satisfy a threshold level and/or equipment breaks or fails.

As shown in FIG. 3, at step 304, process 300 includes determining an initial risk prediction for a patient for a fluid injection. For example, management system 110 may determine, based on patient data, an initial risk prediction for a patient for a fluid injection (e.g., a contrast media injection, etc.) to be administered to the patient. As an example, an initial risk prediction may include a probability that a patient experiences at least one adverse event in response to a fluid injection. Such risk prediction may be numerical from 0 to 100% or bucketed, for example, into low, medium, and high buckets.

An adverse event may include at least one of the following adverse events: an extravasation, catheter coagulation, a post-contrast acute kidney injury, an acute adverse event (e.g., an atopic or allergic reaction, hives, etc.), a contrast media induced nephrotoxicity, a thyroid disorder or thyrotoxicosis, headache, changes in taste, vision disturbances, chest pain, blood vessel widening (vasodilation) and consecutive low blood pressure, nausea, vomiting, back pain, urinary urgency, and injection site reactions such as bleeding, swelling itching, and pain or any combination thereof.

Management system 110 may apply an algorithm or aspects of one or more algorithms, which may be an adaptation or implementation of an individual physician's practice, a professional society guideline, and/or a hospital procedure into computer code, to patient data and/or sensor data associated with a patient to determine an initial risk prediction for the patient (and/or to determine a test prediction, and/or to determine a patient motion level that may cause an artifact in an imaging scan, and/or to determine a wellbeing level of the patient, and/or to determine a current risk prediction, and/or to determine a distress level of the patient). In such an example, different hospitals may have different algorithms or aspects of one or more algorithms based on a local preference, a practice, a country, and/or other factors associated with the different hospitals. In another aspect or embodiment, management system 110, may present the patient data to the physician or healthcare provider who in his/her head may make the assessment of risk, wellbeing, or distress, which may be manually entered into management system 110 for use in subsequent steps.

In some non-limiting embodiments or aspects, management system 110 may apply at least one of the following algorithms to patient data and/or sensor data associated with a patient to determine an initial risk prediction for the patient (and/or to determine a test prediction, and/or to determine a patient motion level that may cause an artifact in an imaging scan, and/or to determine a wellbeing level of a patient, and/or to determine a current risk prediction, and/or to determine a distress level of a patient): an algorithm that uses a baseline comparison (e.g., to determine a change in a parameter from a baseline parameter, etc.); a sequence over time algorithm (e.g., using an average, a slope, a $2^{nd}$ moment, a SPC of a parameter versus normal, etc.); a monotonic, continuous function conversion; an algorithm that converts a continuous function into a discrete function; a threshold based algorithm (e.g., an algorithm with at least one threshold that varies based on patient parameters, time, a volume of fluid injected, etc.); a goodness function; a dictionary mode of curve fitting (e.g., MRF, etc.); an artificial intelligence applied to a time sequence of a single stream of data; an artificial intelligence applied to multiple streams of data simultaneously; a sound triangulation algorithm; an algorithm that categorizes individual parameters and combines categories of parameters; an algorithm that normalizes individual data streams with a continuous (linear or non-linear) function; an algorithm that arrays parameters in a multidimensional space, a polynomial multivariate goodness function, an algorithm or an artificial intelligence that extracts one or more features; an algorithm that is adjusted based on previous data and/or other data streams (e.g., a higher risk patient may have different thresholds for alerting a user and/or stopping an injection, etc.); a phased implementation algorithm (e.g., an algorithm that initially only alerts a user, but as an amount of data collected and/or training increases, that performs other operations such as automatically stopping an injection); or any combination thereof.

In some non-limiting embodiments or aspects, management system 110 may apply one or more algorithms and/or methods disclosed by U.S. Patent Application Publication No. 2016/0224750A1, filed Jan. 29, 2016, the contents of which is hereby incorporated by reference in its entirety, to patient data and/or sensor data associated with a patient to determine an initial risk prediction for the patient (and/or to determine a test prediction, and/or to determine a patient motion level that may cause an artifact in an imaging scan, and/or to determine a wellbeing level of the patient, and/or to determine a current risk prediction, and/or to determine a distress level of the patient).

Example Algorithms

The following Tables 1-4 illustrate example algorithms that may be utilized to determine an initial risk prediction for a user. Example algorithms may be performed by management system 110 and/or a healthcare provider based on information provided to him/her by management system 110 (e.g., via user device 108, etc.), and/or by utilizing user device 108 or a human which may subsequently feed initial risk prediction results to management system 110.

TABLE 1

|  | Points: | | | Risk Prediction |
|---|---|---|---|---|
|  | 1 | 2 | 3 | (sum) |
| Age (years) | 0-50 | 51-70 | >70 | <9 Points: low risk |
| Gender | male | female | Not applicable | |
| BMI | 18.5-25 | 25-30 | 30-40 | 9-14 points: intermediate risk |
| Prior chemotherapy | No | 1-2 cycles | >2 cycles | |
| ECOG status | 0 | 1 + 2 | 3 + 4 | >14 points: high risk |
| Medication status | No | Excluding corticosteroids | Incling corticosteroids | |

Table 1 lists in the leftmost column example parameters associated with a patient that may be considered for determining an initial risk prediction including a probability that the patient experiences an extravasation in response to a fluid injection (e.g., a contrast media injection, etc.). As shown, these parameters may include an age (in years) of the patient, a gender of the patient, a Body Mass Index (BMI) of the patient, a prior chemotherapy status of the patient (e.g., a yes, a no, a number of cycles, etc.), an Eastern Cooperative Oncology Group (ECOG) performance status, a medication status of the patient (e.g., a yes, a no, a current medication, etc.), and/or the like. Each parameter may be given a score of 1, 2, or 3 as listed at the top of the $2^{nd}$ through 4th columns that is dependent on a value of each parameter. If each of the parameters for the algorithm are able to be assessed and/or are available, a sum of the points may provide a score used to represent the initial risk prediction of the patient for an extravasation as indicated in the rightmost column of Table 1. For example, a patient who is 55 years old counts 2 points for age, male is 1 point, a BMI of 27 is 2 points, prior chemotherapy 2 cycles is 3 points, ECOG 1 status is 2 points, and being on medication but not corticosteroids is 2 points. Thus, the sum for that patient is 2+1+2+3+2+2=12, which places this example patient at an intermediate risk for an extravasation.

TABLE 2

|  | Points: | | | Risk Prediction |
|---|---|---|---|---|
|  | 1 | 2 | 3 | (sum) |
| Atopic disorders | None | low | high | 2 points: low risk |
| Prior reaction | None | low | high | >2 points: high risk |

Table 2 lists in the leftmost column example parameters associated with a patient that may be considered for determining an initial risk prediction including a probability that the patient experiences an acute adverse event in response to a fluid injection (e.g., a contrast media injection, etc.). As shown, these parameters may include an atopic disorder status of the patient (e.g., a yes, a no, a level, etc.) and/or a prior reaction to a previous fluid injection status of the patient (e.g., a yes, a no, a level, etc.). An atopic disorder denotes a form of allergy in which a hypersensitivity reaction such as dermatitis and/or asthma may occur in a part of the body not in contact with the allergen. A prior reaction to a previous fluid injection may include an indication associated with the patient having had any prior allergic reactions to prior fluid injections. Low prior reactions may include feelings, flushing, nausea, and/or the like. High prior reactions may include hives and/or anaphylactic reactions requiring treatment. If each of the parameters for the algorithm are able to be assessed and/or are available, a sum of the points may provide a score used to represent the initial risk prediction of the patient for an acute adverse reaction as indicated in the rightmost column of Table 2.

TABLE 3

| | Points: | | | Risk Prediction |
|---|---|---|---|---|
| | 1 | 2 | 3 | (sum) |
| Age | 0-50 | 51-70 | >70 | <8 Points: |
| BMI | 18.5-25 | 25-30 | 30-40 | low risk |
| CKD | 1-3 | 4 | 5 | 8-12 points: |
| Medical status | Healthy | Diabetes or hypertension | Diabetes + hypertension acute | intermediate risk |
| Malignancy | No | Under remission | | >12 points: high risk |

Table 3 lists in the leftmost column example parameters associated with a patient that may be considered for determining an initial risk prediction including a probability that the patient experiences a post-contrast acute kidney injury in response to a fluid injection (e.g., a contrast media injection, etc.). As shown, these parameters may include an age of the patient, a BMI of the patient, a level of Chronic Kidney Disease (CKD) as assessed using a 5 stage glomerular filtration rate scale, a medical status as it relates to existence of diabetes and/or hypertension of the patient, and/or a history and status of malignancy of the patient. If each of the parameters for the algorithm are able to be assessed and/or are available, a sum of the points may provide a score used to represent the initial risk prediction of the patient for a post-contrast acute kidney injury as indicated in the rightmost column of Table 3.

TABLE 4

| | Points: | | | Risk Prediction |
|---|---|---|---|---|
| | 1 | 2 | 3 | (sum) |
| Age | 0-50 | 51-70 | >70 | <7 Points: low risk |
| Gender | male | female | na | 7-9 points: intermediate risk |
| BMI | 18.5-25 | 25-30 | 30-40 | |
| Iodine-deficient geographic area | No | Suspected | proven | >9 points: high risk |

Table 4 lists in the leftmost column example parameters associated with a patient that may be considered for determining an initial risk prediction including a probability that the patient experiences a thyrotoxicosis in response to a fluid injection (e.g., a contrast media injection, etc.). As shown, these parameters may include an age of the patient, a gender of the patient, a BMI of the patient, and an iodine deficient status of a geographic region of the patient. If each of the parameters for the algorithm are able to be assessed and/or are available, a sum of the points may provide a score used to represent the initial risk prediction of the patient for a thyrotoxicosis as indicated in the rightmost column of Table 4.

The example initial risk prediction algorithms illustrated above with respect to Tables 1-4 are meant to be simple and understandable to convey the variety and flexibility of algorithms that may be used to determine an initial risk prediction according to non-limiting embodiments or aspects of the present disclosure. Example algorithms may be performed by management system 110 and/or the healthcare provider based on information provided to him/her by management system 110 (e.g., via user device 108, etc.), and/or by utilizing user device 108 or a human which may subsequently feed the initial risk prediction results to management system 110. It is anticipated that as additional data is collected from patients using data collection processes, systems, and/or devices according to non-limiting embodiments or aspects of the present disclosure, the algorithms used may be improved and/or modified. This improvement and/or modification may be created and implemented by management system 110 in cooperation with a human and/or supervised machine learning, and/or it may be performed by management system 110 itself, which is sometimes called unsupervised machine learning.

As another example, if each of the parameters for an algorithm are not able to be assessed and/or are not available for a patient, one or more alternative algorithms or functions may be used to provide an initial risk prediction based on the parameters of the patient data and/or the sensor data that are available for the patient. For example, one approach may include reducing thresholds for an initial risk prediction by an amount proportional to the parameters that are available for the patient. For example, Table 1 includes 6 pieces of data or parameters and thresholds of <9, 9-14, and >14. If 1 data element or parameter is missing for a patient, the thresholds become ⅚ of those for the full set, or <7.5, 7.5-11.7 and >11.7. Another example approach is to automatically assume a moderate risk score for any missing parameters, for example, 2 points. A more conservative approach may automatically assume a high risk value of 3 for any missing parameters for the patient.

As another example, as more data is collected from more patients, a weighting given to individual parameters in a scoring table may be adjusted, for example, from the uniform distributions shown in the examples of Tables 1-4. In Tables 1-4, a simple summing of the score gives each parameter equal weight. If, for example, for an initial risk prediction of an extravasation assessed using Table 1, it is learned from analysis of the data collected through use of non-limiting embodiments or aspects of the present disclosure that BMI has twice as strong a relationship to a risk of extravasation than the other parameters, BMI may be given a weight of 2/7 and each of the other factors may be given a weight of 1/7, in contrast to the uniform distribution of ⅙ each implicitly used in Table 1.

As another example, a relationship between a parameter, such as age, BMI, and/or the like, and a number of points assigned based on a value of the parameter may be expanded upon to become a continuous functional relationship rather than the discrete binning relationship as shown in the examples of Tables 1-4. For example, such a functional relationship may be as sophisticated as the data enables without overfitting the situation, given a reasonable anticipation of human variations. As an example, such functional relationships may be determined using any applicable multivariate analysis approach. As mentioned, in some non-limiting embodiments or aspects, an initial risk prediction may be determined by a human healthcare provider based, at least in part, from data collected by non-limiting embodiments or aspects of the present disclosure, which may have the benefit of enabling the healthcare provider to gradually gain confidence in the system. There may also be benefits to using multivariate analyses for a similar reason, the workings of these algorithms are understandable by the humans who have to use and trust in the algorithms.

In some non-limiting embodiments or aspects, management system 110 may process patient data and/or sensor data associated with a patient with a machine learning model to determine an initial risk prediction for the patient. For example, management system 110 may generate an initial risk prediction model (e.g., an estimator, a classifier, a prediction model, a detector model, etc.) using machine learning techniques including, for example, supervised and/or unsupervised techniques, such as decision trees (e.g., gradient boosted decision trees, random forests, etc.), logistic regressions, artificial neural networks (e.g., convolutional neural networks, etc.), Bayesian statistics, learning automata, Hidden Markov Modeling, linear classifiers, quadratic classifiers, association rule learning, and/or the like. The initial risk prediction machine learning model may be trained to provide an output including a probability that the patient, in response to a fluid injection (e.g., a contrast media injection, etc.), experiences at least one adverse event in response to an input including the patient data and/or the sensor data associated with the patient. In such an example, the initial risk prediction may include a probability score associated with a prediction that the patient experiences the at least one adverse event in response to the fluid injection.

Management system 110 may generate the initial risk prediction model based on patient data and/or sensor data (e.g., training data, etc.). For example, non-limiting embodiments or aspects of the present disclosure may collect patient data and/or sensor data associated with patients over a period of time in which one of the above described simpler algorithms are employed to determine initial risk predictions for the patients and, when data is collected from a sufficient number of patients (e.g., when an accuracy, a prediction, and/or a recall of a machine learning model generated based on the collected data satisfies a threshold, etc.), the machine learning model may be used to determine initial risk predictions for patients. In some implementations, the initial risk prediction model is designed to receive, as an input, patient data and/or sensor data (e.g., one or more parameters of the patient data and/or the sensor data, etc.) and provide, as an output, a prediction (e.g., a probability, a binary output, a yes-no output, a score, a prediction score, a classification, etc.) as to whether a patient experiences at least one adverse event (e.g., an extravasation, a post-contrast acute kidney injury, an acute adverse event (e.g., an atopic or allergic reaction, etc.), a contrast media induced nephrotoxicity, a thyroid disorder, etc.) in response to a fluid injection (e.g., a contrast media injection, etc.). In some non-limiting embodiments or aspects, management system 110 stores the initial prediction model (e.g., stores the model for later use). In some non-limiting embodiments or aspects, management system 110 stores the initial prediction model in a data structure (e.g., a database, a linked list, a tree, etc.). In some non-limiting embodiments, the data structure is located within management system 110 or external (e.g., remote from) management system 110 (e.g., within auxiliary system 112, etc.).

As shown in FIG. 3, at step 306, process 300 includes providing an initial risk prediction for a patient for a fluid injection and/or a wellbeing level of a patient. For example, management system 110 may provide, to user device 108, before a fluid injection (e.g., a contrast media injection, etc.) is administered to a patient, an initial risk prediction for the patient and/or a wellbeing level of the patient. As an example, user device 108 may display an initial risk prediction for a patient and/or a wellbeing level of the patient to a user (e.g., a physician, etc.) before a fluid injection is administered to the patient.

In some non-limiting embodiments or aspects, an initial risk prediction and/or a wellbeing level may further include at least one of the following: a prompt to administer a medication to the patient before the fluid injection, a prompt to adjust an injection protocol for the fluid injection and/or an imaging protocol for a imaging scan, a prompt to prepare the patient before the fluid injection, a prompt to consult a specialist physician on the at least one adverse event, a prompt to observe and/or follow-up with the patient after the fluid injection and/or the imaging scan, or any combination thereof. For example, management system 110, in response to determining an initial risk prediction (e.g., in response to determining an initial risk prediction including a probability that the patient experiences an adverse event that satisfies a threshold probability, etc.), may determine and recommend actions that a user (e.g., a healthcare worker, etc.) can take to reduce the probability of the patient experiencing the adverse event. As an example, management system 110 may consult a look-up table and/or apply an algorithm (e.g., a machine learning model, etc.) to the initial risk prediction and/or the patient data and/or the sensor data used to generate the initial risk prediction to determine one or more prompts or recommendations to provide to the user that may reduce the probability of the patient experiencing the adverse event. Management system 110 may adjust one or more thresholds to be used by a sensor for monitoring for a good injection and/or an adverse event.

In some non-limiting embodiments or aspects, in response to determining an initial risk prediction (e.g., in response to determining an initial risk prediction including a probability that the patient experiences an adverse event that satisfies a threshold probability, etc.), management system 110, may recommend to the healthcare provider to control and/or adjust one or more operations of fluid injection system 102 and/or imaging system 104, and/or where legally permitted, may automatically control and/or adjust one or more operations of fluid injection system 102 and/or imaging system 104. For example, management system 110 may recommend for manual adjustment or automatically adjust an injection protocol for the fluid injection (e.g., adjust a maximum flow rate, adjust a maximum pressure, adjust an injection duration, adjust a total volume of fluid or contrast delivered or to be delivered (e.g. to reduce total iodine loading), etc.) and/or an imaging protocol for an imaging scan (e.g., adjust a scan time and/or duration (e.g. to accommodate a patient who cannot hold their breath for an initially planned scan duration), adjust kVp (e.g. reduce kVp to allow for an adequate image contrast with a reduced total iodine loading), adjust breathing instructions, etc.). As an example, management system 110 may consult a look-up table and/or apply an algorithm (e.g., a response surface, a machine learning model, etc.) to the initial risk prediction and/or the patient data and/or the sensor data used to generate the initial risk prediction to determine one or more adjustments to the injection protocol and/or the imaging protocol that may reduce the probability of the patient experiencing the adverse event.

For example, based on patient data associated with a known adverse event (e.g., an allergic reaction, etc.) for the patient after a previous fluid injection (e.g., a previous contrast media injection, etc.) and/or an atopic tendency of the patient, management system 110 may determine an initial risk prediction for an acute adverse event that includes a prompt to administer a medication to the patient before the contrast media injection according to applicable guidelines (e.g., American College of Radiology (ACR) guidelines, etc.) and/or a prompt to observe the patient for a predetermined interval (e.g., for a time period longer than normal for a high risk patient) after the contrast media injection while monitoring one or more parameters of the patient relevant to the predicted adverse event.

For example, based on patient data associated with individualized renal function of the patient, such as laboratory surrogate parameters thereof (e.g., eGFR, etc.) and/or a current medication of the patient, management system 110 may determine an initial risk prediction for a contrast media induced nephrotoxicity that includes a prompt to prepare the patient before the contrast media injection according to applicable guidelines (e.g., European Society of Urogenital Radiology guidelines, etc.), such as by administering intravenous hydration, and/or the like, a prompt (and/or an automatic control) to adjust an injection protocol for the contrast media injection and/or an imaging protocol for an imaging scan, and/or a prompt to follow-up with the patient with respect to renal function after the exam, for example to reduce the total iodine given to the patient.

For example, based on patient data associated with a known thyroid disorder of the patient, an environmental influence of the patient (e.g., a regional iodine saturation or nutrition for a region in which the patient lives, etc.), and/or a current medication of the patient, management system 110 may determine an initial risk prediction for a thyroid disorder (e.g., thyrotoxicosis, etc.) that includes a prompt to forgo the contrast media injection and associated imaging exam until a consultation with an endocrinologist is obtained and/or a prompt to administer a medication to the patient before the contrast media injection.

As shown in FIG. 3, at step 308, process 300 includes determining sensor data. For example, sensor system 106 may determine (e.g., determine, collect, acquire, capture, measure, sense, etc.), before, during, and/or after a fluid injection (and/or before, during, and/or after a test injection administered to a patient before the fluid injection), sensor data associated with a patient. As an example, sensor system 106 may determine (e.g., determine, collect, acquire, capture, measure, sense, etc.), before, during, and/or after a fluid injection (and/or before, during, and/or after a test injection administered to a patient before the fluid injection), sensor data associated with a patient.

Sensor data may include at least one of the following parameters associated with a patient: firstly, parameters which may be affected by an injection and/or changes in patient wellbeing such as a heart rate; a sound or vibration (e.g., a sound or vibration associated with a fluid inflow, a sound or vibration proximate an injection site, etc.); a temperature (e.g., a temperature of a fluid inflow, a temperature proximate an injection site, a localized temperature, a tissue temperature, etc.); an oxygen saturation level (e.g., an oxygen saturation of a fluid inflow, an oxygen saturation proximate an injection site, etc.); a pulse rate; an ECG; a body fat/water-content ratio; a tissue impedance; a vessel distribution level; a vessel diameter; a hydration level; a hematocrit level; a skin resistivity; a blood pressure; a muscle tension level; a light absorptivity level; a shaking or trembling or a movement/motion (e.g., a yes, a no, a level, etc.); an arm position; an arm circumference; a respiration rate; a respiration depth; an amount of absorbed radiation; a tightness, a position stability, and/or a contact integrity of contact sensor device 400 and/or 800; an amount of swelling and/or displacement; an EMG; a skin color; a surface vessel dilation (flushing) amount; a bio-impedance; a light absorptivity; an inflammation level; secondly, parameters which are not likely to be immediately affected by an injection and/or changes in a patient wellbeing such as a fat/muscle ratio; a hemoglobin level; and thirdly, environmental parameters such as an environmental temperature of an environment surrounding the patient, a barometric pressure in an environment surrounding the patient; an ambient light level; an ambient sound level; or any combination thereof.

As described in more detail herein below, management system 110 may determine, based on patient data and/or sensor data associated with a patient, a prediction associated with the patient (e.g., an initial risk predication, a test prediction, a current risk prediction, etc.) and/or a wellbeing of the patient. An overall patient wellbeing or patient comfort may be considered to include multiple aspects or dimensions. One aspect may be the medical wellbeing aspect, commonly thought of as the absence of adverse events. A patient may be said to be comfortable if they are having no adverse events; be mildly uncomfortable, for example having a feeling of heat or a hot flash, the feeling of the need to urinate, a queasy stomach, or skin itchiness; or a patient can have a major or severe reaction, for example nausea, hives, or anaphylactic shock that requires timely medical intervention, for example with epinephrine. Another aspect of patient wellbeing is physical wellbeing. A patient may be comfortable lying on the infusion bed or table of the imaging system, may be mildly uncomfortable with some aches or pains that cause them to want to move to relieve the discomfort, or severely uncomfortable which could cause them to involuntarily or uncontrollably move and possibly lead to a degraded image. A third aspect of patient wellbeing is their mental state. A patient may be peaceful or comfortable, accepting of the procedure and cooperating as needed, a patient may be concerned and in a heighted state of alertness in which they might overreact to things like unexpected noises or motions, or in an agitated mental state where it is difficult for them to control their reactions. It is apparent that these three aspects of wellbeing may overlap and are somewhat arbitrary, but they are beneficial for the purposes of this description. It is known to those skilled in the art that physiological parameters such as heart rate, breathing rate, skin conductivity and others may be used to assess the comfort of patients, and an increase in these parameters may be used by management system 110 to alert the healthcare worker to check with the patient, for example when the state of a patient moves from a comfortable to a moderate state on one or more of these aspects. It is difficult for a healthcare worker to manually or mentally pay attention to these subtle changes and it is a goal of non-limiting embodiments or aspects of the present disclosure to synthesize these measurements into a simple alert system for use by the healthcare worker or the overall system including the fluid delivery system and/or the imaging system. It is also a goal of non-limiting embodiments or aspects of the present disclosure to provide aspects which preventatively and proactively promote patient wellbeing, for example education beforehand or a more comfortable environment.

Figure 12:
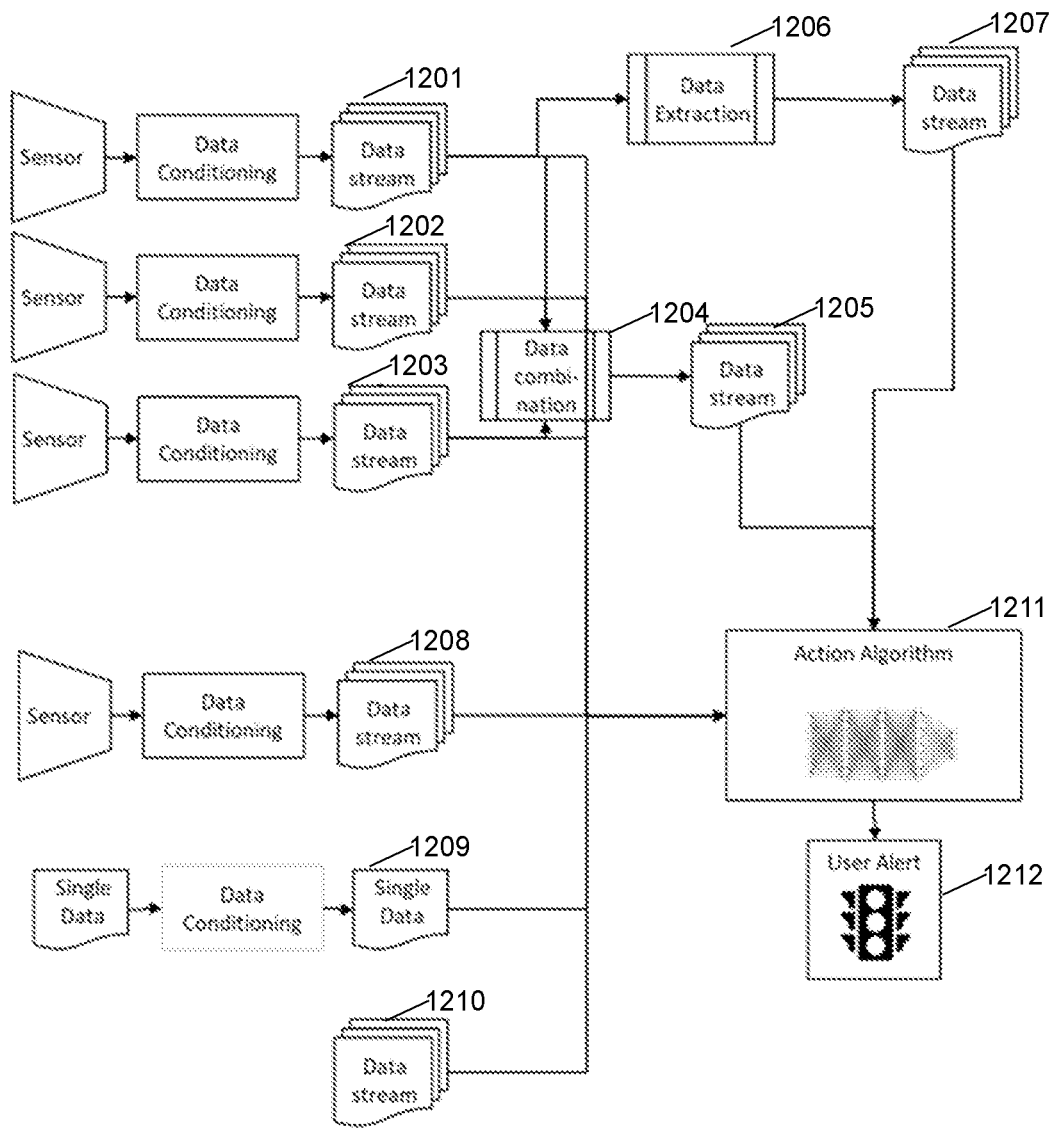
FIG. 12 is a diagram of non-limiting embodiments or aspects of data processing for safeguarding wellbeing of patients for fluid injection.

Referring also to FIG. 12, multiple data processors, data paths, and/or data analysis algorithms may be used to condition various forms and/or streams of patient data and/or sensor data and/or to combine the various forms and/or streams of patient data and/or sensor data into new forms and/or new streams of data and/or to discriminate additional streams of data. The patient data and/or the sensor data and/or the data streams thereof may be used by management system 110 to make recommendations to a user and/or to control operations of fluid injection system 102 and/or imaging system 104 (e.g., to determine an initial risk prediction, to determine a test prediction, to determine whether an injection is a normal injection proceeding as expected, to determine a wellbeing level of a patient, to generate a current risk prediction, to control fluid injection system 102 and/or imaging system 104 in response to such determinations, etc.). For example, the recommendations and/or system control may assess risk, guide preventative actions, minimize occurrence of, detect, and/or manage extravasation, post-contrast acute kidney injury, acute adverse events, contrast media induced nephrotoxicity, and/or thyroid disorder or thyrotoxicosis, thereby reducing one or more severe complications that may be associated with a contrast media injection.

As an example, for detecting extravasation, management system 110 may receive three data streams that represent sound or vibrations measured by three different sensors placed in three different locations on an extremity (e.g., an arm, a leg, a hand, a foot, etc.) of a patient proximate to and/or surrounding an injection site for a test injection and/or a fluid injection (e.g., a contrast media injection, etc.). For example, still referring to FIG. 12, and referring again to FIG. 4E, the rightmost image of the sequence of images in FIG. 4E shows a three sensor array cover of a cross-section of an extremity of a patient that may be used to capture three data streams of sensor data, for example data associated with sound or vibrations. Management system 110 may combine the three sound data streams 1201, 1202, 1203 through a data combination technique 1204 (e.g., triangulation, etc.) to create a combined data stream 1205 that is indicative of a center of one or more sound sources in space. Additionally, or alternatively, management system 110 may apply a data extraction process 1206 to one or more of the three sound data streams to produce one or more additional data streams 1207. For example, management system 110 may apply a real time Fourier transform to a data stream to generate a multidimensional data stream of amplitude as a function of frequency over time. Such a signal may be combined by management system 110 with information about the injection fluid, for example fluid type, viscosity, temperature, flow rate and catheter or other fluid path element properties to assess the sound spectrum, for example to determine whether the sound spectrum indicates a normal or proper injection, a marginal injection, or an abnormal or improper injection which may lead to an adverse event.

In such an example, management system 110 may receive a data stream 1208 including data that changes over time and use the data "as is" or without processing the data in an additional manner before using the data to make recommendations to a user and/or to control operations of fluid injection system 102 and/or imaging system 104. For example, a data stream of sensor data including a parameter associated with a skin temperature of a patient may include data that changes over time and that is used "as is" without additional processing of the data.

In such an example, management system 110 may receive data 1209 that does not change over time. For example, the received data may include information associated with a patient, such as an age of the patient, a chemotherapy status of the patient (e.g., which may indicate a greater likelihood of weaker veins), and/or the like. As an example, the data may include fixed information, for example, information about the contrast media injection and/or the fluid path, such as catheter gauge, contrast concentration, and/or the like.

In such an example, management system 110 may receive a data stream 1210 of sensor data and/or patient data from at least one of the following: fluid injection system 102, imaging system 104, sensor system 106, user device 108, auxiliary system 112, or any combination thereof. For example, management system 110 may receive, from fluid injection system 102, data associated with programmed flow rates, actual or measured flow rates, pressures, concentrations, and/or other injection related data.

In such an example, management system 110 may apply one or more algorithms 1211 as described herein to the data streams of patient data and/or sensor data to determine the recommendations and/or system control 1212 (e.g., to determine an initial risk prediction, to determine a test prediction, to determine a patient wellbeing level, to generate a current risk prediction, to control fluid injection system 102 and/or imaging system 104 in response to such determinations, etc.). For example, the sound data streams may be affected by contrast concentration, temperature, flow rate, and the catheter type and/or size, as well as unknown variables or factors such as patient vein structure and/or a position of the catheter in the vein of the patient. At a start of a test injection or a contrast media injection, management system 110 may expect the frequency and amplitude of the sound to be within a certain normal or expected range, which may have been learned and/or determined from prior studies and fixed into an algorithm. Additionally, or alternatively, the algorithm may employ ongoing learning and adaptation. If the sound at the start of the test injection or the contrast media injection is outside of the normal or expected range, the algorithm may cause management system 110 to indicate that the sound is outside the normal or expected range to the user, which may indicate that an incorrect catheter is being used and/or an incorrect fluid is being used for the contrast media injection. For example, a frequency of the sound (e.g., the "woosh", "whistle" or "trill", etc.) can be dependent upon catheter gauge, length, and stiffness, as well as the fluid and properties of the fluid, a flow rate, vessel properties, and a position of the catheter or needle in the vein or tissue of the patient, for example pressed against the wall of the vessel. For example, this information upon which the frequency of the sound is dependent may be input to management system 110 as data manually by a user and/or automatically from fluid injection system 102.

In such an example, during the injection, an algorithm may expect the sound data to be relatively consistent until there is a change in fluid concentration, fluid temperature, and/or fluid flow rate. For example, management system 110 may alert a user if there is a change in fluid concentration, fluid temperature, and/or fluid flow rate that satisfies a threshold change or magnitude at a time when no change is anticipated by the algorithm. Management system 110 may alert a user when conditions change (e.g., a change in contrast media concentration, etc.) at a time when there is an absence of an expected change in the sound data. Similarly, during a proper contrast media injection, the sound spectrum and/or a location in space of a source of the sound may be relatively constant (e.g., a tip of the catheter does not move, except maybe at a very beginning of an injection, etc.). For example, management system 110 may allow for a modest spectrum change or movement at the start of the injection or when there is a change in total volumetric flow or mass flow, but if the initial movement satisfies a threshold movement level at a time associated therewith, management system 110 may provide an indication of the movement to the user (e.g., as part of the wellbeing level of the patient, etc.). In such an example, management system 110 may use parameters, such as a vein status of a patient, to set one or more thresholds used to determine one or more alerts, for example, to set a lower threshold for more at-risk patients. In such an example, management system 110 may use multiple data streams and sub-algorithms as a "double check" on each other, for example, only alerting the user if two or more sub-algorithms indicate an alert, thereby reducing the likelihood of false alarms. Other ways of combining sub-algorithm results, such as response surfaces and non-linear functions, may also be utilized.

As shown in FIG. 3, at step 310, process 300 includes determining a test prediction. The test prediction determination of step 310 may be optional, for example, performance of a test injection and determination of sensor data during the test injection may be optional. For example, management system 110 may determine, based on sensor data determined during a test injection administered to a patient before a fluid injection (e.g., before a contrast media injection, etc.), a test prediction. As an example, a test prediction may include a probability that a patient experiences an extravasation in response to a fluid injection (e.g., a contrast media injection, etc.). For example, intravenous access of the patient may be checked in a standardized manner to predict an uncomplicated high-flow and high-pressure contrast media application by performing (manually and/or mechanically) a standardized stepwise saline test injection for the patient and determining, with sensor system 106, during the test injection, sensor data associated with the patient. In such an example, sound or changes in measured parameters of the patient (e.g., changes in vessels and/or tissue proximate to the injection site, etc.) may be determined under controlled dynamic low-flow and low-pressure conditions of the test injection. For example, management system 110 may determine, based on a turbulent sound measured by at least one sound or vibration sensor located proximate the injection site, which is caused by inflowing fluid in a vessel, a change in temperature, a change in oxygenation level, a comparison with a loaded pressure of injector 152, and/or the like, the test prediction (e.g., a probability of an extravasation under high-flow and high-pressure of a contrast media injection, etc.) and/or rate a sufficiency of the test injection.

Management system 110 may apply an algorithm or aspects of an algorithm, which may be an adaptation and/or implementation of a professional society guideline and/or a hospital procedure into computer code, to patient data and/or sensor data associated with a patient to determine a test prediction for a patient. In such an example, different hospitals may have different algorithms or aspects of one or more algorithms based on a local preference, a practice, a country, and/or other factors associated with the different hospitals. In some non-limiting embodiments or aspects, management system 110 may employ a scoring table as described herein above with respect to the examples in Tables 1-4 to determine a test prediction for a patient based on one or more parameters of the patient data and/or the sensor data associated with the patient (e.g., a change in temperature, a change in oxygenation level, etc.)

In some non-limiting embodiments, management system 110 may generate a test prediction machine learning model in the same or similar manner as the initial risk prediction machine learning model (e.g., as described herein). In some non-limiting embodiments or aspects, the test prediction machine learning model may be different from the initial risk prediction machine learning model. For example, the input provided to the test prediction machine learning model or the output provided by the test prediction machine learning model may be different from the input provided to the initial risk prediction machine learning model or the output provided by the initial risk prediction machine learning model. As an example, the test prediction model may be designed to receive, as an input, patient data and/or sensor data (e.g., one or more parameters of the patient data and/or the sensor data measured during a test injection, etc.) and provide, as an output, a prediction (e.g., a probability, a binary output, a yes-no output, a score, a prediction score, a classification, etc.) as to whether a patient is experiencing or experiences an extravasation in response to a contrast media injection.

As shown in FIG. 3, at step 312, process 300 includes providing a test prediction. The providing of a test prediction of step 312 may be optional, for example, performance of a test injection and determination of sensor data during the test injection may be optional. For example, management system 110 may provide, to user device 108, a test prediction including a probability that a patient experiences an adverse event, for example an extravasation, in response to a fluid injection (e.g., a contrast media injection, etc.). As an example, user device 108 may display the test prediction to a user (e.g., a physician, etc.) before the fluid injection (e.g., the contrast media injection, etc.) is administered to the patient and the imaging study is conducted.

In some non-limiting embodiments or aspects, a test prediction may further include at least one of the following: a prompt to administer a medication to the patient before the contrast media injection, a prompt to adjust an injection protocol for the contrast media injection and/or an imaging protocol for an imaging scan, a prompt to prepare the patient before the contrast media injection, a prompt to consult a specialist physician on the predicted extravasation, a prompt to observe and/or follow-up with the patient after the contrast media injection and/or the imaging scan, or any combination thereof. For example, management system 110, in response to determining a test prediction (e.g., in response to determining a test prediction including a probability that the patient experiences an extravasation that satisfies a threshold probability, etc.), may determine and recommend actions that a user (e.g., a healthcare worker, etc.) can take to reduce the probability of the patient experiencing the extravasation. As an example, management system 110 may consult a look-up table and/or apply an algorithm (e.g., a machine learning model, etc.) to the test prediction and/or the patient data and/or the sensor data used to generate the test prediction to determine one or more prompts or recommendations to provide to the user that may reduce the probability of the patient experiencing the extravasation.

In some non-limiting embodiments or aspects, in response to determining a test prediction (e.g., in response to determining a test prediction including a probability that the patient experiences extravasation that satisfies a threshold probability, etc.), management system 110 may automatically control and/or adjust one or more operations of fluid injection system 102 and/or imaging system 104. For example, management system 110 may automatically adjust an injection protocol for the contrast media injection (e.g., adjust a maximum flow rate, adjust a maximum pressure, etc.) and/or an imaging protocol for an imaging scan (e.g., adjust a scan time, etc.). As an example, management system 110 may consult a look-up table and/or apply an algorithm (e.g., a machine learning model, etc.) to the test prediction and/or the patient data and/or the sensor data used to generate the test prediction to determine one or more automatic adjustments to the injection protocol and/or the imaging protocol that may reduce the probability of the patient experiencing the extravasation.

As shown in FIG. 3, at step 314, process 300 includes determining at least one of a current risk prediction and a wellbeing level of a patient. For example, management system 110 may determine, after a fluid injection (e.g., a contrast media injection, etc.) is started (e.g., at a time period during and after the fluid injection, simultaneous to starting the fluid injection, etc.), based on sensor data determined after the fluid injection is started, at least one of a current risk prediction and a wellbeing level of a patient. As an example, a current risk prediction may include a probability that a patient experiences at least one adverse event in response to the fluid injection (e.g., a probability that the patient is currently experiencing at least one adverse event, a probability that the patient will experience at least one event at a future time, etc.) In such an example, a probability that a patient experiences at least one adverse event that satisfies at least one threshold probability (e.g., 90 percent probability, 100 percent probability, etc.) may indicate that the patient is currently experiencing the at least one adverse event, and/or a probability that a patient experiences at least one adverse event that fails to satisfy the at least one threshold probability may indicate a probability that the patient will experience the at least one adverse event at a future time. In some non-limiting embodiments or aspects, management system 110 may further determine at least one of a current risk prediction and a wellbeing level of a patient during and/or after the fluid injection based on patient data associated with the patient.

In some non-limiting embodiments or aspects, management system 110 may determine (e.g., determine during the fluid injection, etc.), based on sensor data determined during the fluid injection, at least one of a current risk prediction and a wellbeing level of a patient. For example, even in a case of a test prediction that indicates a low probability of an extravasation for a patient for a contrast media injection, an extravasation may still occur during the contrast media injection, for example, due to an intravenous access being incorrectly located outside the vein, being dislocated and/or kinked after placement or during the contrast media injection, and/or a vessel of the patient rupturing due to patient movement and/or high-pressure and high-flow conditions.

In some non-limiting embodiments or aspects, management system 110 may determine (e.g., determine after the fluid injection is completed, during and/or after an imaging scan, etc.), based on sensor data determined after the fluid injection is completed, at least one of a current risk prediction and a wellbeing level of a patient.

Management system 110 may apply an algorithm or aspects of an algorithm, which may be an adaptation and/or an implementation of a professional society guideline and/or a hospital procedure into computer code, to sensor data associated with a patient to determine at least one of a current risk prediction and a wellbeing level of a patient. In such an example, different hospitals may have different algorithms or aspects of one or more algorithms based on a local preference, a practice, a country, and/or other factors associated with the different hospitals. In some non-limiting embodiments or aspects, management system 110 may employ a scoring table as described herein above with respect to the examples in Tables 1-4 to determine at least one of a current risk prediction and a wellbeing level of a patient based on one or more parameters of the sensor data associated with the patient (e.g., a change in temperature, a change in oxygenation level, a motion level, a heartrate, etc.).

In some non-limiting embodiments or aspects, management system 110 may generate a current risk prediction machine learning model in the same or similar manner as the initial risk prediction machine learning model and/or the test prediction machine learning model (e.g., as described herein). In some non-limiting embodiments, the current risk prediction machine learning model may be different from the initial prediction machine learning model and/or the test prediction machine learning model. For example, the input provided to the current risk prediction machine learning model and/or the output provided by the current risk prediction machine learning model may be different from the input provided to the initial prediction machine learning model and/or the test prediction model and/or the output provided by the initial prediction machine learning model and/or the test prediction model. As an example, the current risk prediction machine learning model may be designed to receive, as an input, sensor data (e.g., one or more parameters of the sensor data measured during and/or after a contrast media injection, etc.) and provide, as an output, a prediction (e.g., a probability, a binary output, a yes-no output, a score, a prediction score, a classification, etc.) as to whether a patient experiences at least one adverse event in response to a fluid injection. As an example, the current risk prediction machine learning model may be designed to receive, as an input, sensor data (e.g., one or more parameters of the sensor data measured during and/or after a contrast media injection, etc.) and provide, as an output, a classification (e.g., a probability, a binary output, a yes-no output, a score, a prediction score, a classification, etc.) as to a wellbeing level of a patient.

As shown in FIG. 3, at step 316, process 300 includes providing a current risk prediction and/or a wellbeing level of a patient. For example, management system 110 may provide, to user device 108, during and/or after the fluid injection (e.g., after the fluid injection is started, etc.), the current risk prediction and/or the wellbeing level of the patient. As an example, management system 110 may provide, to user device 108, during the fluid injection, the current risk prediction and/or the wellbeing level of the patient, and/or user device 108 may display, during the fluid injection, the current risk prediction and/or the wellbeing level of the patient to a user (e.g., a physician, etc.) during the fluid injection. As an example, management system 110 may provide, to user device 108, after the fluid injection, the current risk prediction and/or the wellbeing level of the patient, and/or user device 108 may display, after the fluid injection, the current risk prediction and/or the wellbeing level of the patient to a user (e.g., a physician, etc.) after the fluid injection.

In some non-limiting embodiments or aspects, a current risk prediction may include an alert generated in response to and/or associated with at least one of the following: a movement of a tip of a catheter that satisfies a threshold movement, a change in fluid concentration that satisfies a threshold change, a fluid temperature that satisfies a threshold temperature, a fluid flow rate that satisfies a threshold magnitude, or any combination thereof. For example, management system 110 may provide an alert with a current risk prediction in response to the current risk prediction satisfying at least one threshold probability that the patient experiences the at least one adverse event, for example, to alert a user of a condition that may lead to the patient experiencing the at least one event.

In some non-limiting embodiments or aspects, a current risk prediction may include a visualization of changes to tissue of the patient that are related to, caused by, and/or reflect inflow of fluid from a fluid injection.

In some non-limiting embodiments or aspects, in response to determining a current risk prediction that satisfies at least one threshold level (e.g., that indicates the patient experiences an adverse event (e.g., an extravasation, etc.) during a fluid injection (and/or test injection) and/or will experience the adverse event, etc.), management system 110 may automatically fluid injection system 102 to stop the fluid injection (and/or the test injection) (e.g., control injector 152 to stop injection or delivery of contrast media or fluid to the patient, etc.) and/or control or cause imaging system 104 to abort the imaging procedure, thereby saving the patient from an unproductive radiation exposure because the contrast media needed for the procedure would be insufficient or lacking and/or patient motion or other imaging impediments related to an adverse event may be occurring.

In some non-limiting embodiments or aspects, at step 316, in process 300, management system 110 may receive feedback from a user or operator, which management system 110 may use to update and/or adjust one or more of the algorithms described herein with respect to steps 308-314. For example, a user may inform management system 110 if an assessment or determination made by management system 110 of the occurrence of a normal injection or an adverse event is correct or if the reality is discordant with the assessment or determination so that the one or more algorithms may be improved as more experience is gained in actual practice on the wide variety of patients that are encountered.

Figure 5A:
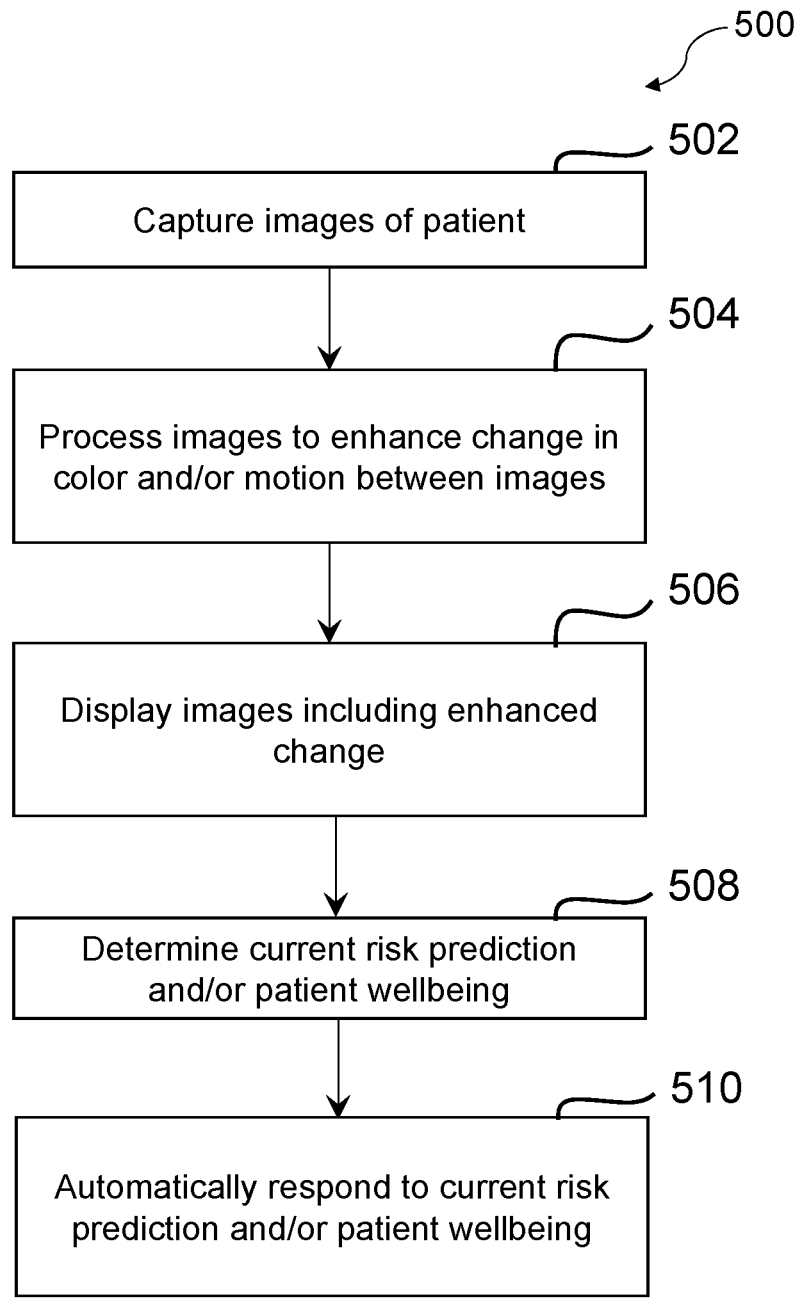
FIGS. 5A and 5B are flowcharts of non-limiting embodiments or aspects of processes for safeguarding wellbeing of patients for fluid injection.

Referring now to FIG. 5A, FIG. 5A is a flowchart of non-limiting embodiments or aspects of a process 500 for assessing the normality or abnormality of a patient and/or an injection and thus safeguarding the wellbeing of patients before, during, and/or after fluid injection. In some non-limiting embodiments or aspects, one or more of the steps of process 500 may be performed (e.g., completely, partially, etc.) by management system 110 (e.g., one or more devices of management system 110, etc.). In some non-limiting embodiments or aspects, one or more of the steps of process 500 may be performed (e.g., completely, partially, etc.) by a user or another device or a group of devices separate from or including management system 110, such as fluid injection system 102 (e.g., one or more devices of fluid injection system 102, etc.), imaging system 104 (e.g., one or more devices of imaging system 104, etc.), sensor system 106 (e.g., one or more devices of sensor system 106, etc.), user device 108 (e.g., one or more devices of a system of user device 108, etc.), and/or auxiliary system 112 (e.g., one or more devices of auxiliary system 112, etc.).

As shown in FIG. 5A, at step 502, process 500 includes capturing images of a patient. For example, sensor system 106 may capture images of a patient. As an example, sensor system 106 may include non-contact sensor 164b including an image capture device (e.g., a camera, etc.), and sensor data captured by the image capture device may include a plurality of images (e.g., a video stream, etc.) of the patient (e.g., images including an injection site on the patient and/or an area proximate and/or surrounding an injection site on the patient, etc.) captured over a period of time. In some non-limiting embodiments or aspects, step 502 of process 500 may be performed as part of and/or in a same or similar manner to step 308 of process 300. In such an example, the at least one adverse event may include an extravasation.

As shown in FIG. 5A, at step 504, process 500 includes processing images to enhance, magnify, or amplify a change in a color and/or a motion between the images. For example, management system 110 may process the plurality of images of the patient captured over the period of time to enhance, magnify, or amplify a change in at least one of a color and a motion (e.g., low frequency motion, higher frequency sound based motion or vibration, etc.) between the plurality of images (e.g., between one or more objects and/or areas in the plurality of images, etc.). As an example, management system 100 may process the plurality of images using a Eulerian Video Magnification technique as described in the paper by Wu et al. titled Eulerian Video Magnification for Revealing Subtle Changes in the World published July 2012, the disclosure of which is hereby incorporated by reference in its entirety.

As shown in FIG. 5A, at step 506, process 500 includes displaying images including an enhanced change. For example, management system 110 may display, to a user (e.g., via user device 108, etc.), the plurality of images including the enhanced change. Accordingly, a user (e.g., a physician, etc.) that views the enhanced images may more easily detect whether the patient is experiencing an extravasation due to the enhanced changes in color and/or motion in the images. In some non-limiting embodiments or aspects, step 506 of process 500 may be performed as part of and/or in a same or similar manner to step 312 and/or step 316 of process 300. In some non-limiting embodiments or aspects, the enhanced images are not displayed to the user and/or management system 110 processes and assess the enhanced images internally.

As shown in FIG. 5A, at step 508, process 500 includes determining a current risk prediction and/or a wellbeing level of a patient. For example, management system 110 may determine whether the injection is proceeding as expected, if the patient is experiencing discomfort, and/or if a patient experiences or is likely to experience an extravasation or another adverse event. As an example, management system 110 may determine, based on the enhanced change, the current risk prediction (e.g., an extravasation probability, etc.) and/or the wellbeing level of the patient. As an example, management system 110 may apply an algorithm or aspects of one or more algorithms (e.g., a machine learning model, etc.), to the plurality of images including the enhanced change to determine the current risk prediction (e.g., an extravasation probability, etc.) and/or the wellbeing level of the patient. In some non-limiting embodiments or aspects, step 508 of process 500 may be performed as part of and/or in a same or similar manner to step 310 and/or step 314 of process 300.

As shown in FIG. 5A, at step 510, process 500 includes automatically responding to a current risk prediction and/or a wellbeing level of a patient. For example, management system 110 may perform one or more operations in response to a determination that the injection is proceeding as expected, a determination the patient is experiences discomfort, or a determination the patient experiences an extravasation or another adverse event. For example, management system 110 may perform one or more desired steps or actions in response to a determination that an adverse event is happening, is about to happen, or is at an increased likelihood of happening (e.g., in response to a current risk prediction including a probability that satisfies at least one threshold probability, etc.). As an example, the one or more desired steps or actions may be set by a user, a hospital, or some appropriate body through management system 110. Such actions may include alerting an operator to the assessment or determination, automatically controlling injector 152 to slow an injection rate of the injection, automatically controlling injector 152 to pause the injection, and/or automatically stopping a fluid injection (e.g., a contrast media injection, etc.). As an example, management system 110 may automatically stop a fluid injection (e.g., control fluid injection system 102 to stop a flow and/or delivery of a fluid or contrast media, etc.) in response to determining that the patient experiences the extravasation or another adverse event and/or in response to determining that the wellbeing level of the patient satisfies at least one threshold level.

Figure 5B:
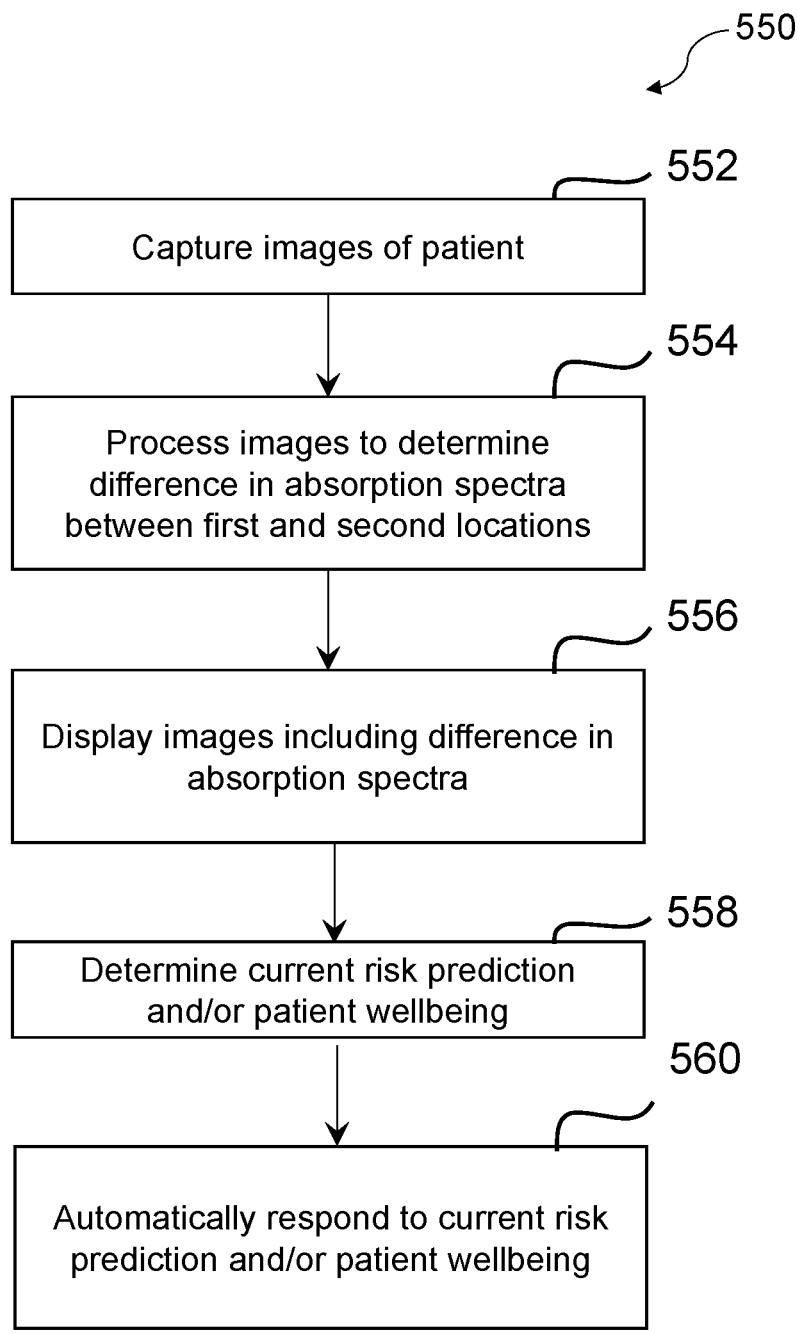

Referring now to FIG. 5B, FIG. 5B is a flowchart of non-limiting embodiments or aspects of a process 550 for assessing a normality or an abnormality of a patient and/or an injection and thus assessing and/or safeguarding the wellbeing of patients before, during, and/or after a fluid injection. In some non-limiting embodiments or aspects, one or more of the steps of process 550 may be performed (e.g., completely, partially, etc.) by management system 110 (e.g., one or more devices of management system 110, etc.). In some non-limiting embodiments or aspects, one or more of the steps of process 550 may be performed (e.g., completely, partially, etc.) by a user or another device or a group of devices separate from or including management system 110, such as fluid injection system 102 (e.g., one or more devices of fluid injection system 102, etc.), imaging system 104 (e.g., one or more devices of imaging system 104, etc.), sensor system 106 (e.g., one or more devices of sensor system 106, etc.), user device 108 (e.g., one or more devices of a system of user device 108, etc.), and/or auxiliary system 112 (e.g., one or more devices of auxiliary system 112, etc.).

As shown in FIG. 5B, at step 552, process 500 includes capturing images of a patient. For example, sensor system 106 may capture images of a patient. As an example, sensor system 106 may include non-contact sensor 164b including an image capture device (e.g., a camera, an IR camera, etc.), and sensor data determined by the image capture device may include a plurality of images (e.g., a plurality of IR images, etc.) of the patient (e.g., of an injection site on the patient and/or an area proximate and/or surrounding an injection site on the patient, etc.) captured over a period of time. In some non-limiting embodiments or aspects, step 552 of process 500 may be performed as part of and/or in a same or similar manner to step 308 of process 300. In such an example the at least one adverse event may include an extravasation.

As shown in FIG. 5B, at step 554, process 500 includes processing images to determine a difference in absorption spectra between a first location and a second location on a patient and/or between two points in time for the same location. For example, sensor system 106 may include an image capture device including an infrared (IR) camera and the plurality of images may include a plurality of IR images. As an example, management system 110 may process the plurality of IR images to determine a difference in absorption spectra between a first location on the patient (e.g., a location associated with a vessel of a patient, etc.) and a second location on the patient (e.g., a location associated with tissue of a patient exterior to a vessel of the patient, etc.) in the plurality of images. For example, a longer wavelength IR spectrum may be used to assess temperature as fluids injected via a contrast media injection are typically cooler than a body temperature of a patient. As an example, management system 110 may process the plurality of images using a method as described in U.S. Patent Application Publication No. 2006/0173360A1, filed Jan. 7, 2005, the contents of which is hereby incorporated by reference in its entirety.

As shown in FIG. 5B, at step 556, process 550 includes displaying the images including the difference in absorption spectra and/or absorption spectra over time. For example, management system 110 may display, to a user (e.g., via user device 108, etc.), the plurality of images including the difference in absorption spectra in a manner visible to a user. Accordingly, a user (e.g., a physician, etc.) that views the images may more easily detect whether the patient is experiencing a normal injection or an extravasation due to the difference in absorption spectra represented in the displayed images. As an example, the first location on the patient may include a vessel or vein of the patient, and the second location on the patient may include tissue of the patient surrounding the vessel or vein of the patient. In some non-limiting embodiments or aspects, step 556 of process 550 may be performed as part of and/or in a same or similar manner to step 312 and/or step 316 of process 300.

As shown in FIG. 5B, at step 558, process 550 includes process 500 includes determining a current risk prediction and/or a wellbeing level of a patient. For example, management system 110 may determine whether the injection is proceeding as expected, if the patient is experiencing discomfort, and/or if the patient experiences an extravasation and/or another adverse event. For example, management system 110 may determine, based on the difference in absorption spectra between the first location on the patient and the second location on the patient, whether the patient experiences the extravasation and/or another adverse event. As an example, management system 110 may compare the difference in absorption spectra to one or more thresholds to determine whether the patient experiences the extravasation and/or another adverse event and/or to determine the wellbeing level of the patient. In some non-limiting embodiments or aspects, step 558 of process 550 may be performed as part of and/or in a same or similar manner to step 310 and/or step 314 of process 300.

As shown in FIG. 5B, at step 560, process 560 includes automatically responding to a current risk prediction and/or a wellbeing level of a patient. For example, management system 110 may automatically perform one operations in response to a determination that the injection is proceeding as expected, a determination the patient is experiences discomfort, or a determination the patient experiences an extravasation or another adverse event. For example, management system 110 may perform one or more desired steps or actions in response to a determination that an extravasation or another adverse event is happening, is about to happen, or is at an increased likelihood of happening (e.g., in response to a current risk prediction including a probability that satisfies at least one threshold probability, etc.). The desired steps or actions may be set by a user, a hospital, and/or some appropriate body through management system 110. Such actions may include alerting an operator to the assessment or determination, automatically controlling injector 152 to slow an injection rate of the injection, automatically controlling injector 152 to pause the injection, and/or automatically stopping a fluid injection. For example, management system 110 may automatically stop a fluid injection (e.g., control fluid injection system 102 to stop a flow and/or delivery of a fluid or contrast media, etc.) in response to determining that the patient experiences the extravasation or another adverse event and/or in response to determining that the wellbeing level of the patient satisfies at least one threshold level.

Figure 6:
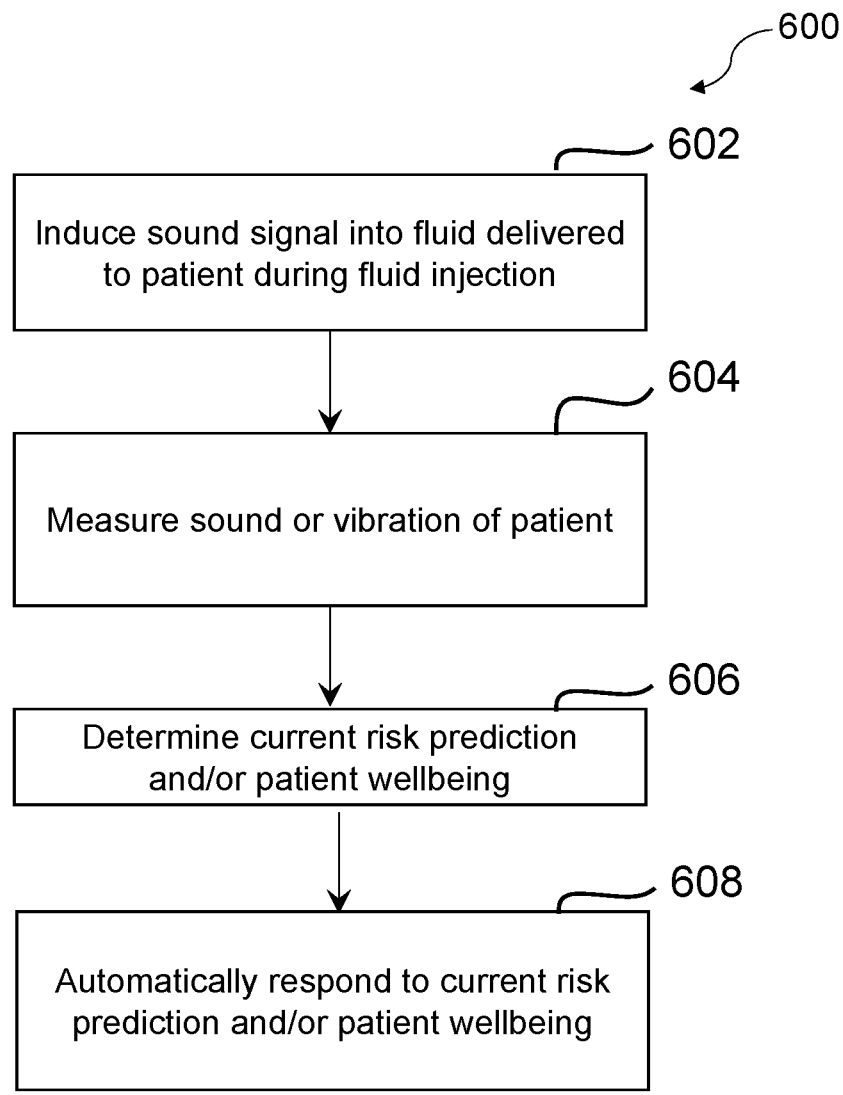
FIG. 6 is a flowchart of non-limiting embodiments or aspects of a process for safeguarding wellbeing of patients for fluid injection.

Referring now to FIG. 6, FIG. 6 is a flowchart of non-limiting embodiments or aspects of a process 600 for assessing a normality or an abnormality of a patient and/or an injection and thus assessing and/or safeguarding wellbeing of patients for fluid injection. In some non-limiting embodiments or aspects, one or more of the steps of process 600 may be performed (e.g., completely, partially, etc.) by management system 110 (e.g., one or more devices of management system 110, etc.). In some non-limiting embodiments or aspects, one or more of the steps of process 600 may be performed (e.g., completely, partially, etc.) by a user or another device or a group of devices separate from or including management system 110, such as fluid injection system 102 (e.g., one or more devices of fluid injection system 102, etc.), imaging system 104 (e.g., one or more devices of imaging system 104, etc.), sensor system 106 (e.g., one or more devices of sensor system 106, etc.), user device 108 (e.g., one or more devices of a system of user device 108, etc.), and/or auxiliary system 112 (e.g., one or more devices of auxiliary system 112, etc.).

Figure 7:
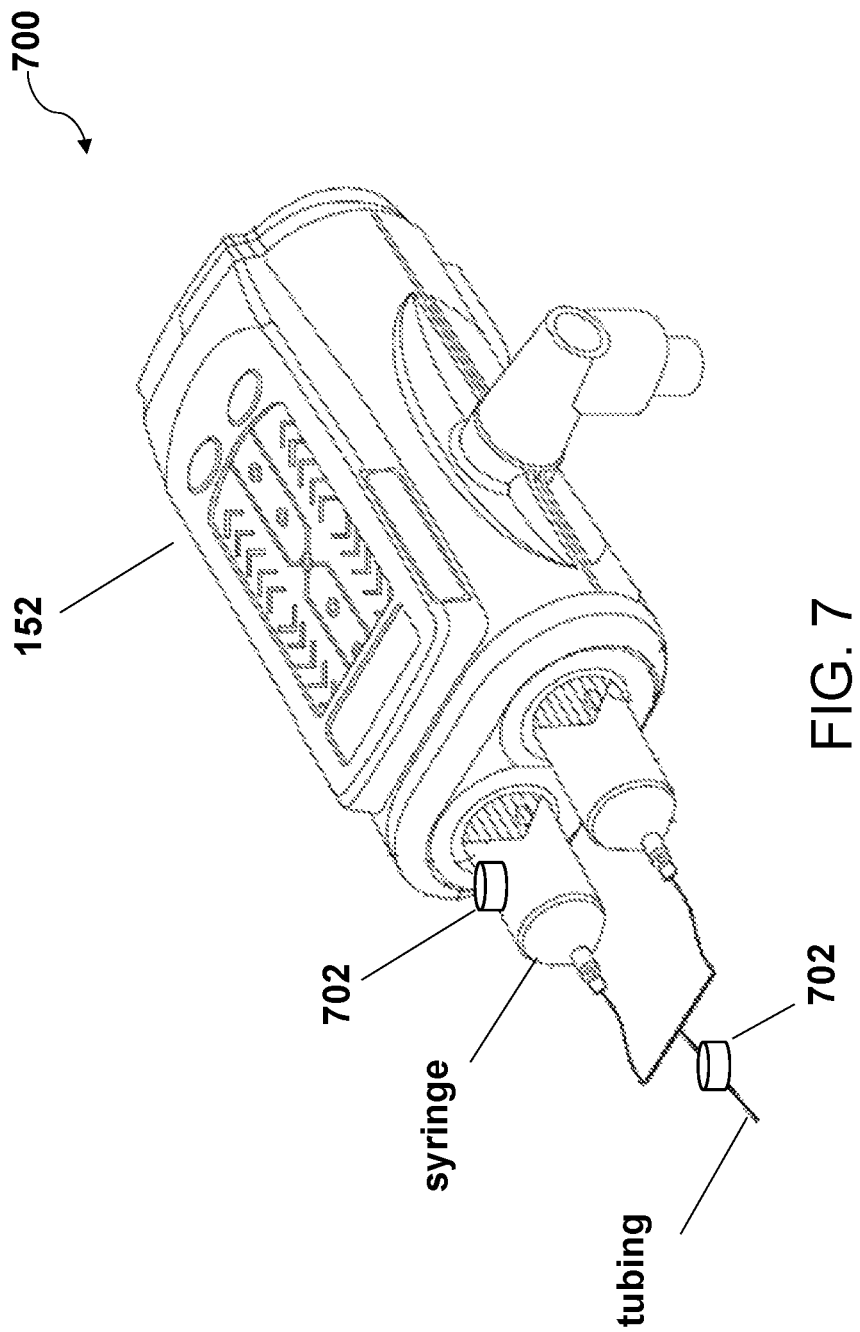
FIG. 7 is a perspective view of non-limiting embodiments or aspects of an implementation of a fluid injector including a sound generation device.

As shown in FIG. 6, at step 602, process 600 includes inducing a sound or vibratory signal into fluid delivered to a patient during a fluid injection (and/or a test injection). For example, and referring also to FIG. 7, an implementation 700 of fluid injector 152 may include sound generation device 702 (e.g., an oscillator, a speaker, a vibrator, a whistle, etc.) connected to at least one of an injector, a syringe, and a fluid path that deliver fluid to a patient during a fluid injection (e.g., a contrast media injection, etc.) (and/or a test injection). As an example, sound generation device 702 may induce, during a fluid injection (and/or a test injection) to a patient, a sound signal into fluid (e.g., contrast media, saline, etc.) delivered to the patient during the fluid injection (and/or the test injection), which may induce or transmit sound waves or pulses into a vasculature, surrounding tissue, and/or blood of a patient to enhance assessment of injection normalcy, injection progress, and/or detection of an extravasation. Although shown in FIG. 7 as connected to a contrast injector used for CT imaging procedures, non-limiting embodiments or aspects are not limited thereto, and sound generation device 702 may be incorporated into any type of fluid delivery device. In another non-limiting embodiment or aspect of the present disclosure, sound generation device 702 may generate sound as the fluid being delivered to the patient flows through the fluid path and/or the patient. A special device or element of the fluid path may be used to generate this sound, similar to how a whistle generates a sound in the air as air flows over the whistle. One phenomenon that may be used is vortex shedding. With vortex shedding, the frequency of the sound may be dependent upon the fluid flow rate, speed, and other properties. This has the benefit of providing a qualitative and potentially quantitative indication of one or more local properties of the injection to management system 110, which may be used to assess the normalcy, progress, and/or risk of occurrence of an adverse event. A sound or a vibration may include any mechanical oscillatory or vibratory phenomena of any duration, externally generated, imposed, and/or inserted, or intrinsically created and/or generated, whether within or outside a normal auditory range of a human.

As shown in FIG. 6 at step 604, process 600 includes measuring a sound or vibration of a region or part of patient. For example, sensor system 106 may measure a sound or vibration of a patient (e.g., during the fluid injection, simultaneously with induction of the sound signal into the fluid, etc.). As an example, sensor system 106 may include a sound or vibration sensor (e.g., implemented with contact sensor device 400, located proximate to an injection site on a patient, etc.), and sensor system 106 may measure, with the sound or vibration sensor, at least one of a frequency and an amplitude of a sound or vibration of the patient (e.g., at a location proximate to an injection site on the patient, etc.), for example, as the sensor data associated with the patient. In such an example, the sound waves or pulses induced into the patient may improve a quality or a signal-to-noise ratio of a sound or vibration signal captured by the sound or vibration sensor, which may enable management system 110 to more readily determine an extravasation during the fluid injection based on the sound or vibrations captured by the sound or vibration sensor. For example, a frequency and/or an amplitude of the sound signal may be tuned to enhance detection by the sound or vibration sensor. In some non-limiting embodiments or aspects, step 604 of process 600 may be performed as part of and/or in a same or similar manner to step 308 of process 300.

As shown in FIG. 6, at step 606, process 600 includes determining a current risk prediction and/or a wellbeing level of a patient. For example, management system 110 may determine whether an injection is proceeding as expected, if the patient is experiencing discomfort, and/or if the patient experiences an extravasation or another adverse event. For example, management system 110 may determine the status of an injection (e.g., the current risk prediction and/or the wellbeing level of the patient, etc.), based on the at least one of the frequency, the amplitude, the apparent center or location of the sound, and/or the change over time of any of the properties associated with the measured sound or vibration of the patient. As an example, injected fluid that pools under skin of a patient during an extravasation may generate a different sound signature compared to fluid that flows through a vasculature of a patient, which may manifest as increased local sound magnitude where the fluid pools and/or a shift in frequency of the sound due to the Doppler effect. In such an example, management system 110 may determine whether the patient experiences an extravasation by comparing the measured frequency and/or amplitude to one or more thresholds, a library of known frequencies and/or amplitudes, and/or a baseline frequency and/or amplitude determined during a test injection. Accordingly, non-limiting embodiments or aspects of the present disclosure may address signal to noise limitations of passively monitoring fluid injection and associated fluid extravasation with an external sensor array by creating and measuring a more detectable enhanced signal in a vasculature of a patient. In some non-limiting embodiments or aspects, step 606 of process 600 may be performed as part of and/or in a same or similar manner to step 310 and/or step 314 of process 300.

As shown in FIG. 6, at step 608, process 600 includes automatically responding to a current risk prediction and/or a wellbeing level of a patient. For example, management system 110 may automatically perform one or more operations in response to a determination that the injection is proceeding as expected, a determination the patient is experiences discomfort, or a determination the patient experiences an extravasation or another adverse event. For example, management system 110 may perform one or more desired steps or actions in response to a determination that that an extravasation is happening, is about to happen, or is at an increased likelihood of happening (e.g., in response to a current risk prediction including a probability that satisfies at least one threshold probability, etc.). The desired steps or actions may be set by a user, a hospital, or some appropriate body through management system 110. Such actions may include alerting an operator to the assessment or determination, automatically controlling injector 152 to slow an injection rate of the injection, automatically controlling injector 152 to pause the injection, and/or automatically stopping a fluid injection. For example, management system 110 may automatically stop a fluid injection (e.g., control fluid injection system 102 to stop a flow and/or delivery of a fluid or contrast media, etc.) in response to determining that the patient experiences the extravasation or another adverse event and/or in response to determining that the wellbeing level of the patient satisfies at least one threshold level.

Medical imaging may be a stressful experience for a patient. The stress may begin when the patient learns find that they have a condition that requires further "tests". Just that term, "tests", can induce fear because, to the patient, the term may mean that they may be very sick, and the patient may have no idea what the tests may be like. The stress can increase when specific tests are prescribed and the patient gains secondhand information and misinformation about the medical imaging to be done. Medical imaging may also be a potentially painful experience for a patient, for example, if the patient experiences an extravasation. However, in focusing on detecting and/or reducing specific adverse events, for example, extravasation, more general patient distress and sources of patient distress may be overlooked. Accordingly, there is a need for systems and methods that assess or determine general patient distress and provide solutions for responding thereto to improve a level of patient care.

Figure 9:
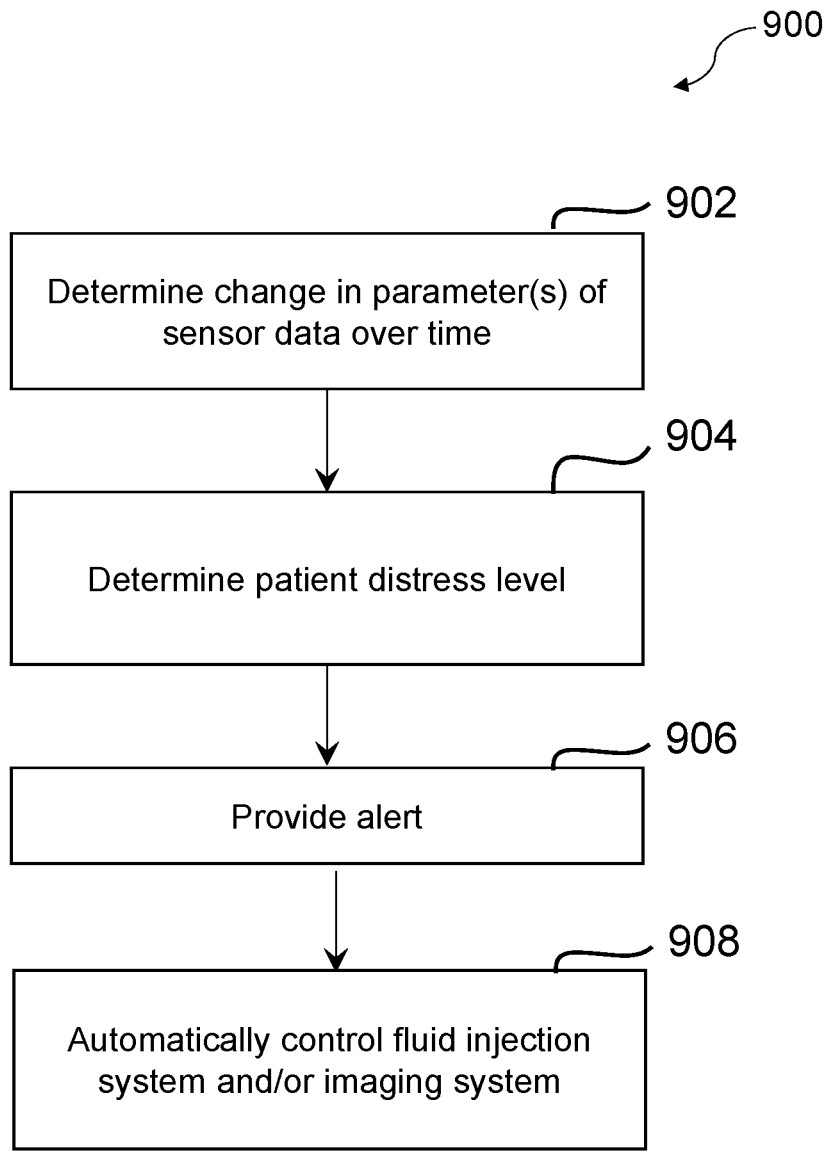
FIG. 9 is a flowchart of non-limiting embodiments or aspects of a process for safeguarding wellbeing of patients for fluid injection.

Referring now to FIG. 9, FIG. 9 is a flowchart of non-limiting embodiments or aspects of a process 900 for safeguarding wellbeing of patients for fluid injection. In some non-limiting embodiments or aspects, one or more of the steps of process 900 may be performed (e.g., completely, partially, etc.) by management system 110 (e.g., one or more devices of management system 110, etc.). In some non-limiting embodiments or aspects, one or more of the steps of process 900 may be performed (e.g., completely, partially, etc.) by a user or another device or a group of devices separate from or including management system 110, such as fluid injection system 102 (e.g., one or more devices of fluid injection system 102, etc.), imaging system 104 (e.g., one or more devices of imaging system 104, etc.), sensor system 106 (e.g., one or more devices of sensor system 106, etc.), user device 108 (e.g., one or more devices of a system of user device 108, etc.), and/or auxiliary system 112 (e.g., one or more devices of auxiliary system 112, etc.).

As shown in FIG. 9, at step 902, process 900 includes determining a change in one or more parameters of sensor data associated with a patient over a period of time. For example, management system 110 may determine a change in one or more parameters of sensor data associated with a patient over a period of time. As an example, contact sensor device 800 (and/or contact sensor device 400) may determine (e.g., with a pulse oximeter, a skin resistance sensor, an accelerometer, a temperature sensor, etc.) the sensor data (e.g., a heart rate, an oxygen saturation, a skin resistivity, a movement or motion level, a temperature proximate an injection site, etc.) and transmit the sensor data to management system 110. Alternatively, or additionally, non-contact sensor 164b may measure patient motion, flushing, swelling, and/or any other measurement described herein as measured by non-contact sensor 164b and transmit the sensor data to management system 110.

As shown in FIG. 9, at step 904, process 900 includes determining a patient distress level associated with a patient. For example, management system 110 may determine whether a patient is comfortable or distressed or may be becoming distressed. For example, management system 110 may determine, based on the sensor data determined after the fluid injection is started, whether the patient is distressed. As an example, management system 110 may determine a change in the one or more parameters of the sensor data over a period of time, compare the change in the one or more parameters to at least one threshold change, and determine the patient distress level and/or that the patient is distressed in response to the change in the one or more parameters satisfying the at least one threshold change. In some non-limiting embodiments or aspects, step 904 of process 900 may be performed as part of and/or in a same or similar manner to step 310 and/or step 314 of process 300.

As shown in FIG. 9, at step 906, process 900 includes providing an alert. For example, management system 110 may provide, to user device 108, in response to determining that the patient is in distress (e.g., in response to a patient distress level that satisfies at least one threshold level, etc.), an alert indicating that the patient is in distress. As an example, user device 108 may display the alert to a user (e.g., a physician, etc.), which may include information and/or data associated with a type of discomfort and/or distress experienced by the patient. For example, a user may take one or more actions to help improve the comfort of the patient in order to reduce the level of distress of the patient. In some non-limiting embodiments or aspects, step 906 of process 900 may be performed as part of and/or in a same or similar manner to step 312 and/or step 316 of process 300.

As shown in FIG. 9, at step 908, process 900 includes controlling a fluid injection system and/or an imaging system. For example, management system 110 may automatically control, in response to determining that the patient is in distress (e.g., in response to a patient distress level that satisfies at least one threshold level, etc.), at least one of (i) a fluid injection system to modify, pause, or stop a fluid media injection (and/or a test injection); and (ii) an imaging system to adjust a timing of an imaging operation (e.g., to delay or pause imaging until management system 110 determines that the patient is no longer in distress, etc.). In some non-limiting embodiments or aspects, step 908 of process 900 may be performed as part of and/or in a same or similar manner to step 312 and/or step 316 of process 300.

In some non-limiting embodiments or aspects, management system 110 may automatically or semi-automatically take action to control one or more devices of fluid injection system 102, imaging system 104, and/or sensor system 106 in an attempt to distract a patient that is in distress. For example, in response to determining that the patient is in distress (e.g., in response to a patient distress level that satisfies at least one threshold level, etc.), management system 110 may automatically control a haptic device (e.g., a patient bed or table, contact sensor device 400 and/or 800, a vibrator, an acupressure device, etc.), a speaker, and/or a display to distract the patient (e.g., to distract a patient experiencing nausea, to distract a patient from an IV placement, etc.).

Figure 10:
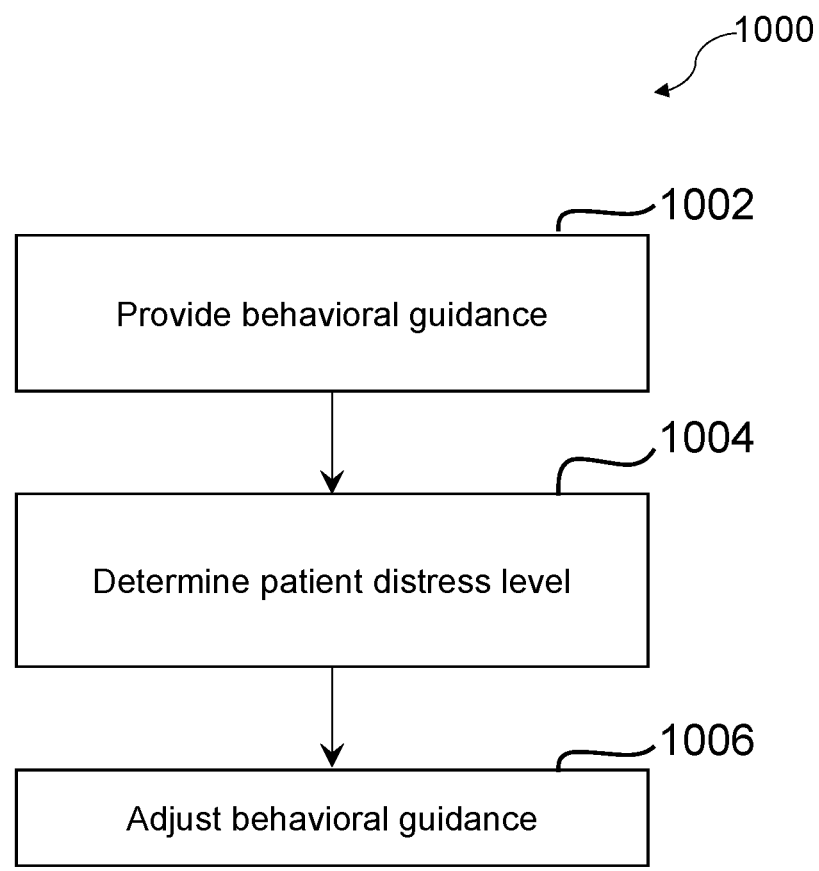
FIG. 10 is a flowchart of non-limiting embodiments or aspects of a process for safeguarding wellbeing of patients for fluid injection.

Referring now to FIG. 10, FIG. 10 is a flowchart of non-limiting embodiments or aspects of a process 1000 for promoting and/or safeguarding the wellbeing of patients for fluid injection. In some non-limiting embodiments or aspects, one or more of the steps of process 1000 may be performed (e.g., completely, partially, etc.) by management system 110 (e.g., one or more devices of management system 110, etc.). In some non-limiting embodiments or aspects, one or more of the steps of process 1000 may be performed (e.g., completely, partially, etc.) by a user or another device or a group of devices separate from or including management system 110, such as fluid injection system 102 (e.g., one or more devices of fluid injection system 102, etc.), imaging system 104 (e.g., one or more devices of imaging system 104, etc.), sensor system 106 (e.g., one or more devices of sensor system 106, etc.), user device 108 (e.g., one or more devices of a system of user device 108, etc.), and/or auxiliary system 112 (e.g., one or more devices of auxiliary system 112, etc.).

As shown in FIG. 10, at step 1002, process 1000 includes providing breathing, postural (e.g. lay still, hold position, etc.), and/or other behavioral guidance. For example, management system 110 may, control, with the at least one processor, at least one of a light (e.g., a light of injector 152, etc.), a display (e.g., injector user interface 156, etc.), a speaker, and a haptic device (e.g., a patient bed or table, contact sensor device 400 and/or 800, etc.) to provide at least one of visual instructions, audio instructions, and haptic instructions for guiding breathing of the patient (e.g., before, during, or after a contrast media injection).

An ability of a patient to control breathing and to remain still is useful for radiology imaging procedures. Power injector designs are typically highly focused on needs and interactions of the users (e.g., medical professional, etc.). Less attention, however, is typically placed on the patient and their interactions and perceptions, which may be overlooked during the development of a medical device. In a typical procedure, breathing guidance is typically instructed by the medical professional (e.g., via intercom). Also, many medical environments are perceived as cold (e.g., lacking affection and warmth, etc.). There are variety of patients who become overwhelmed with stress and anxiety leading up to and undergoing a medical procedure.

Figure 11:
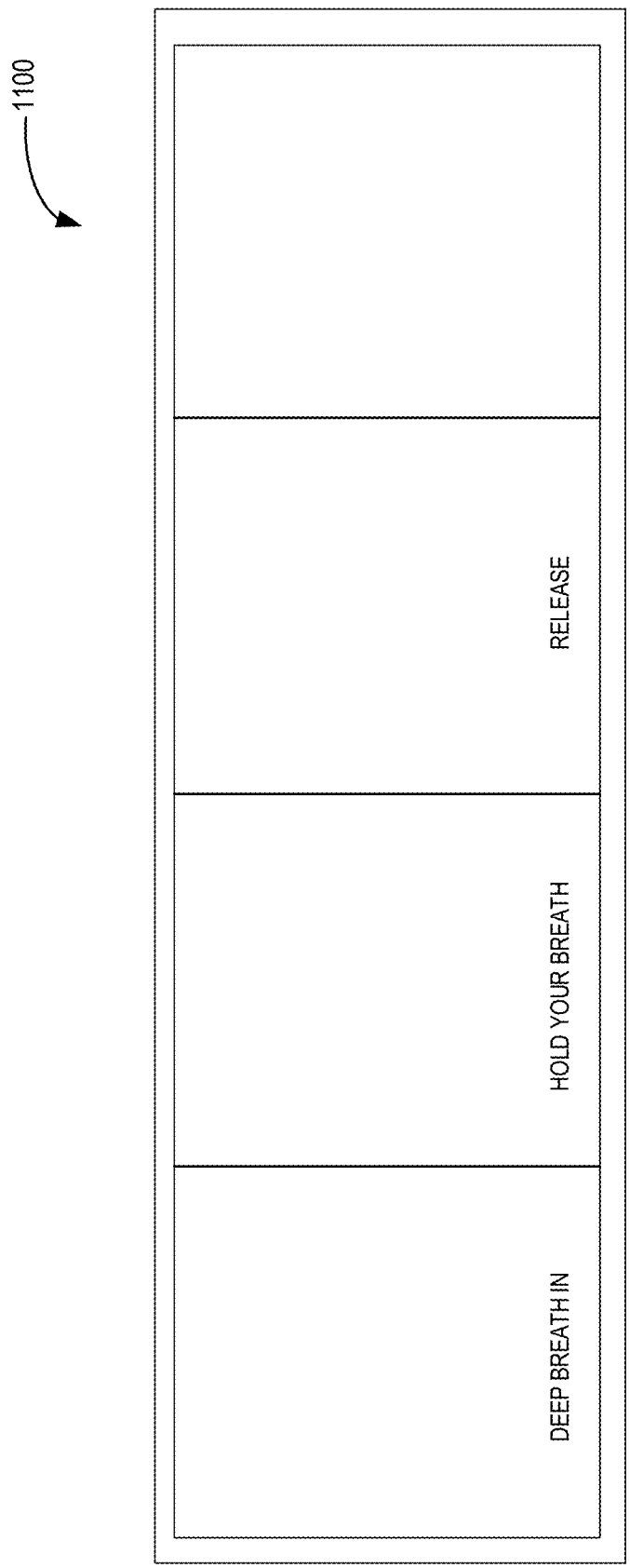
FIG. 11 illustrates non-limiting embodiments or aspects of visual instructions for guiding breathing of a patient.

Improving meditation practices with the use of illustration, lighting, and sound within the medical environment, such as a scan room of a radiology suite, may transform the patient's experience of the entire procedure. Patients typically lay supine during imaging procedures, seeing mostly the ceiling and the wall of the inner bore of the scanner. With no direct visual line, the use of colored lighting (e.g., blue=calm, etc.) and ambient sounds (e.g., soothing voice prompts, and white noise) may reach the patient to aid in relaxing them. Referring also to FIG. 11, FIG. 11 illustrates non-limiting embodiments or aspects of instructions 1100 for guiding breathing of a patient, which may be delivered in a form of an animation to a patient in a scan room via a display (e.g., an injector display, an imager display, a user device, etc.). As shown in FIG. 11, an animated halo (e.g., on a graphical user interface, as lighting from injector 152 and/or imager 158, etc.) illustrating shallow and deep breathing by widening and closing may be displayed to the patient.

As the halo widens from a starting state, audio instructions may prompt the patient to take a deep breath, with the illumination from the injector intensifying and with colored light glowing into the bore of the scanner. At the fully widened state, the display may remain at full illumination as the voice prompts the patient to hold their breath. When the patient is able to breathe out (e.g., due to an imaging operation ending or pausing, etc.), the halo may shrink to the starting state with the illumination becoming less intense. Optionally the halo may contain a number which counts down to let the patient know when they may breathe again. This gives the patient information on what is expected of them. Accordingly, a visual output with audio prompts may be used to demonstrate proper breathing for a patient undergoing and/or about to undergo a radiology procedure, such as a contrast media injection, an imaging scan, and/or the like, to calm the patient prior to a procedure and/or to provide breathing guidance during the procedure. In this way, a visual output and audio prompts may be used to soothe the patient from the scan room of a radiology suite by using mood lighting, calming voice prompts, ambient noise, and/or haptic feedback (e.g., a vibrator in contact sensor device 400 and/or 800 vibrating in time with the animation, etc.), which are commonly used in meditation, which may aid in relaxation for patients who feel tense and anxious. Variations in the guidance and/or the presentation thereof may be used to accommodate a variety of patients (e.g., every day, pediatric, cognitive disabilities, phobias, etc.).

In some non-limiting embodiments or aspects, instructions for guiding breathing of the patient may be provided outside of and/or prior to a patient entering a procedure or scan room. For example, the instructions may be used as an educational tool to inform and/or prepare patients and provided to the patients via an application for a patient care portal or system as described herein. In some non-limiting embodiments or aspects, the guidance be used to allow practice before the procedure, optionally in the imaging suite. Management system 110 in combination with sensors 164a and 164b may assess a patient's ability to follow the planned instructions. If it is determined by management system 110 that the patient cannot follow the planned instructions, the contrast injection and the imaging procedure may be modified to accommodate the patient.

In some non-limiting embodiments or aspects, management system 110 may adjust, based on a timing of an imaging operation of imaging system 104, the at least one of the visual instructions, the audio instructions, and the haptic instructions for guiding the breathing of the patient. For example, management system 110 may automatically adjust the instructions to instruct the patient to hold their breath when imaging system 104 (e.g., imager 158, etc.) is actively imaging the patient.

As shown in FIG. 10, at step 1004, process 1000 includes determining a distress level associated with a patient. For example, management system 10 may determine whether a patient is comfortable, becoming distressed, or is distressed (e.g., whether a patient distress level satisfies at least one threshold level, etc.). For example, management system 110 may determine, based on the sensor data determined after the fluid injection is started (e.g., based on sensor data determined via contact sensor device 400, based on sensor data determined via contact sensor device 800, etc.), a distress level of the patient and/or whether the patient is distressed. As an example, management system 110 may determine a change one or more parameters of the sensor data over a period of time, compare the change in the one or more parameters to at least one threshold change, and determine the distress level of the patient and/or that the patient is distressed in response to the change in the one or more parameters satisfying the at least one threshold change. In some non-limiting embodiments or aspects, step 1004 of process 1000 may be performed as part of and/or in a same or similar manner to step 904 of process 900.

In some non-limiting embodiments or aspects, management system 110 may determine, based on the sensor data determined after the fluid injection is started, whether a fluid injection and/or an image scan for the patient satisfies one or more compliance thresholds (e.g., a threshold associated with patient movement during an imaging scan, a threshold associated with a quality of the images acquired during the imaging scan, etc.). For example, management system 110 may process sensor data associated with a movement/motion of the patient during the scan and artifact generation in images of the scan to determine an effect of table motion.

As shown in FIG. 10, at step 1006, process 1000 includes adjusting behavioral guidance. For example, management system 110 may adjust, in response to determining that the patient is distressed (e.g., in response to a patient distress level that satisfies at least one threshold level, etc.), the at least one of the visual instructions, the audio instructions, and the haptic instructions for guiding the breathing and/or the positioning of the patient. As an example, management system 110 may provide audio and/or visual feedback to the patient associated with measured breathing of the patient and/or adjust a timing of the instructions and/or an imaging scan time to correspond to the instructions. In some non-limiting embodiments or aspects, step 1006 of process 1000 may be performed as part of and/or in a same or similar manner to step 312 and/or step 316 of process 300.

In some non-limiting embodiments or aspects, contact sensor device 400, 800 may remain in contact with a patient for some time after the fluid injection to provide information to management system 110 to enable management system 110 to assess the ongoing, post injection wellbeing of the patient and to monitor for the possibility of delayed adverse events, for example a delayed allergic reaction. Management system 110 may inform a user of the patient status (e.g., via user device 108, etc.) and may recommend additional monitoring time and/or other actions if the patient status or wellbeing is not what is optimal or sufficient for release.

This disclosure anticipates the continued improvement of the devices, systems, and processes described herein. As measurements are taken, data collected, and predictions compared to actual outcomes for more and more patients, the algorithms may be improved or replaced with more sophisticated algorithms, for example trained neural networks may replace the summed scores used in Tables 1-4. Initially, management system 110 may only provide predictions to healthcare workers and alert healthcare workers to a potential adverse event or discomfort. Management system 110 may do more and become more intelligent and rely less on healthcare workers as data is gathered by management system 110.

As an example, consider the measurement of sound or vibration via contact sensors 164a and/or non-contact sensors 164b. While it is common for a healthcare worker to place two fingers on the skin over the outlet or tip of the catheter to "feel" the vibration of fluid exiting the catheter at the start of a test injection or a fluid injection (e.g., a contrast media injection, etc.), the healthcare worker cannot continue to do that because they generally need to be out of the imaging suite when the imaging itself occurs. Thus, there is very little data about how these vibrations evolve over the time course of an injection. Some data has been taken on phantom and phantom/human hybrid setups. However, because adverse events such as extravasation or allergic reactions are so rare and phantom or animal models only go so far, it is anticipated that management system 110 may initially provide a capability which might be termed an a "remote electronic stethoscope" that enables the healthcare worker to remotely listen to or feel the sounds of an injection over the whole injection rather than only feeling the injection site only for a few seconds at the start of the injection. Initially, management system 110 may not make any judgement or take any action to change the injection or imaging study itself. However, as normal and abnormal injections are monitored and measured and related to the outcomes, management system 110 may provide a capability to alert the healthcare worker to the possible existence of an adverse event and/or alert the healthcare worker to the anticipation of an adverse event beginning, similar to the devices and systems of U.S. Patent Application Publication No. 2016/0224750A1, filed Jan. 29, 2016, the entire contents of which is hereby incorporated by reference. Management system 110 may recommend actions to the healthcare worker or may take actions which can be cancelled by the healthcare worker. As normal and abnormal injections are continued to be monitored and measured and related to the outcomes, management system 110 may become sufficiently sophisticated and/or trained in one or more areas that management system 110 may sense and act in response to situations in a manner in which humans are incapable. In addition, healthcare workers may gain confidence in management system 110 over time and with improvements and so all it to make more automatic recommendations and actions. In addition, various sensor electrical or physical arrangements may be improved based on learning from accumulated data.

The descriptions and disclosures herein make clear that the devices, systems, and methods may collect and assess information about any injection and ultimately assess any injections along a continuum of goodness or normalcy to existence of an adverse event. This is beyond the common two bucket, single threshold differentiation of normal and abnormal that has been used in past devices which are looking for abnormalities.

In many of the aspects and embodiments described herein, sensors 164a and/or 164b and management system 110 have been considered in relation to and in communication with other systems. In some non-limiting embodiments or aspects, sensors 164a and/or 164b management system 110 may be a standalone system. An example of this may include a remote electronic stethoscope function described herein. It may be a simple system which senses sound and amplifies and transmits the sensed and amplified sound so that a healthcare worker can hear the sounds emanating from the injection. A second example of a simple, standalone system is non-contact sensor 164b monitoring the injection site, enhancing selected aspects of the image, and transmitting them for the healthcare work to observe.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A system comprising:
   at least one processor programmed and/or configured to:
   obtain patient data associated with a patient;
   determine, based on the patient data, an initial risk prediction for the patient associated with a fluid injection to be administered to the patient, wherein the initial risk prediction includes a probability that the patient experiences at least one adverse event in response to the fluid injection, and wherein the at least one adverse event includes: an extravasation, a post-contrast acute kidney injury, an acute adverse event, a contrast media induced nephrotoxicity, and a thyrotoxicosis such that the initial risk prediction includes a probability that the patient experiences the extravasation, a probability that the patient experiences the post-contrast acute kidney injury, a probability that the patient experiences the acute adverse event, a probability that the patient experiences the contrast media induced nephrotoxicity, and a probability that the patient experiences the thyrotoxicosis;

provide, to a user device, before the fluid injection is administered to the patient, the initial risk prediction, wherein the initial risk prediction further includes at least one of: a prompt to administer a medication to the patient before the fluid injection, a prompt to adjust an injection protocol for the fluid injection, a prompt to adjust an imaging protocol for an imaging scan, a prompt to prepare the patient before the fluid injection, a prompt to observe and/or follow-up with the patient after the fluid injection, or any combination thereof;

obtain sensor data associated with the patient and determined after the fluid injection is started;

determine, based on the sensor data determined after the fluid injection is started, a current risk prediction for the patient associated with the fluid injection, wherein the current risk prediction includes a probability that the patient experiences the at least one adverse event in response to the fluid injection; and provide, to the user device, the current risk prediction.

2. The system of claim 1, wherein the at least one processor is further programmed and/or configured to:
automatically control, based on the current risk prediction, at least one of: (i) a fluid injection system to stop the fluid injection; and (ii) an imaging system to adjust a timing of an imaging operation.

3. The system of claim 1, wherein the patient data includes at least one of the following parameters associated with the patient: an age; a gender; a weight; a prior chemotherapy status; an estimated glomerular filtration rate (eGFR); a thyroid stimulating hormone (TSH) level; a Triiodothyronine (FT3) Thyroxine (FT4) ratio (FT3/FT4); a level of an environmental influence; a prior reaction to a previous fluid injection status; an atopic disorder status; a medical status associated with at least one of diabetes and hypertension; a congestive heart failure status; a hematocrit level; a renal failure status; a malignancy status; an implanted device for a central venous access status; a type of a medication; a type of fluid media to be administered in the fluid injection; an injection protocol associated with a fluid injection; a type of an imaging exam; a flow rate associated with the fluid injection; a catheter gauge associated with the fluid injection; a total volume of fluid associated with the fluid injection; a pressure curve associated with the fluid injection, a pressure limit curve associated with a fluid injection, an injection site location associated with the fluid injection; or any combination thereof.

4. The system of claim 1, wherein the sensor data includes at least one of the following parameters associated with the patient: a heart rate; a sound or vibration; a temperature; an oxygen saturation level; an electrocardiogram (ECG); a body fat/water-content ratio; a tissue impedance; a vessel distribution level; a vessel diameter; a hydration level; a hematocrit level; a skin resistivity; a blood pressure; a muscle tension level; a light absorptivity level; a motion level; an arm position; an arm circumference; a respiration rate; an amount of absorbed radiation; an electromyogram (EMG); a skin color; a surface vessel dilation amount; a bio-impedance; a light absorptivity; a hemoglobin level; an inflammation level; an environmental temperature of an environment surrounding the patient, a barometric pressure in the environment surrounding the patient; an ambient light level; an ambient sound level; or any combination thereof.

5. The system of claim 1, further comprising:
at least one sensor configured to determine, after the fluid injection is started, the sensor data associated with the patient.

6. The system of claim 5, wherein the at least one sensor is further configured to:
determine, after the fluid injection, the sensor data, and
wherein the at least one processor is further programmed and/or configured to:
determine, based on the sensor data determined after the fluid injection, the current risk prediction; and
provide, to the user device, after the fluid injection, the current risk prediction.

7. The system of claim 5, wherein the at least one adverse event includes the extravasation, and wherein the at least one processor is further programmed and/or configured to provide the current risk prediction by automatically controlling, in response to determining that the patient experiences the extravasation, the fluid injection system to stop the fluid injection.

8. The system of claim 5, wherein the at least one sensor includes at least one of: an image capture device; an accelerometer; a strain gauge; a global positioning system (GPS); a skin resistivity or conductance sensor; a heart rate monitor; a microphone; a thermal or temperature sensor; a pulse oximeter; a hydration sensor; a dosimeter; an ultrasound sensor; an acoustic sensor; one or more electrodes configured to measure at least one of a tissue impedance, an electromyogram (EMG), and an electrocardiogram (ECG); a microwave sensor; a mechanical impedance sensor; a chemical sensor; a force or pressure sensor; or any combination thereof.

9. A system comprising:
at least one sensor configured to determine, before a fluid injection associated with a patient is started, sensor data associated with the patient; and
at least one processor programmed and/or configured to:
obtain patient data associated with the patient; and
determine, based on the patient data and the sensor data, an initial risk prediction for the patient associated with the fluid injection to be administered to the patient, wherein the initial risk prediction includes a probability that the patient experiences at least one adverse event in response to the fluid injection, and wherein the at least one adverse event includes: an extravasation, a post-contrast acute kidney injury, an acute adverse event, a contrast media induced nephrotoxicity, and a thyrotoxicosis such that the initial risk prediction includes a probability that the patient experiences the extravasation, a probability that the patient experiences the post-contrast acute kidney injury, a probability that the patient experiences the acute adverse event, a probability that the patient experiences the contrast media induced nephrotoxicity, and a probability that the patient experiences the thyrotoxicosis; and
provide, to a user device, before the fluid injection is administered to the patient, the initial risk prediction, wherein the initial risk prediction further includes at least one of: a prompt to administer a medication to the patient before the fluid injection, a prompt to adjust an injection protocol for the fluid injection, a prompt to adjust an imaging protocol for an imaging scan, a prompt to prepare the patient before the fluid injection, a prompt to observe and/or follow-up with the patient after the fluid injection, or any combination thereof.

10. A system comprising:
at least one sensor configured to determine, after a fluid injection associated with a patient is started, sensor data associated with the patient; and
at least one processor programmed and/or configured to:
determine, based on the sensor data determined after the fluid injection is started, a current risk prediction for the patient associated with the fluid injection, wherein the current risk prediction includes a probability that the patient experiences at least one adverse event in response to the fluid injection, and wherein the at least one adverse event includes: an extravasation, a post-contrast acute kidney injury, an acute adverse event, a contrast media induced nephrotoxicity, and a thyrotoxicosis such that the current risk prediction includes a probability that the patient experiences the extravasation, a probability that the patient experiences the post-contrast acute kidney injury, a probability that the patient experiences the acute adverse event, a probability that the patient experiences the contrast media induced nephrotoxicity, and a probability that the patient experiences the thyrotoxicosis; and
provide, to the user device, the current risk prediction, wherein the at least one processor is further programmed and/or configured to provide the current risk prediction by automatically controlling, in response to determining that the patient experiences the extravasation, the fluid injection system to stop the fluid injection.

11. A system comprising:
at least one processor programmed and/or configured to:
obtain sensor data associated with a patient and determined after a fluid injection associated with the patient is started;
determine, based on the sensor data determined after the fluid injection is started, a current risk prediction for the patient associated with the fluid injection, wherein the current risk prediction includes a probability that the patient experiences at least one adverse event in response to the fluid injection, and wherein the at least one adverse event includes: an extravasation, a post-contrast acute kidney injury, an acute adverse event, a contrast media induced nephrotoxicity, and a thyrotoxicosis such that the current risk prediction includes a probability that the patient experiences the extravasation, a probability that the patient experiences the post-contrast acute kidney injury, a probability that the patient experiences the acute adverse event, a probability that the patient experiences the contrast media induced nephrotoxicity, and a probability that the patient experiences the thyrotoxicosis; and
provide, to the user device, the current risk prediction; and
automatically control, based on the current risk prediction, at least one of: (i) a fluid injection system to stop the fluid injection; and (ii) an imaging system to adjust a timing of an imaging operation.

12. A system comprising:
at least one processor programmed and/or configured to:
provide, via an application program interface (API), to at least one user device, information associated with a fluid injection to be administered to a patient;
receive, via the API, from the at least one user device, before the fluid injection, patient data associated with the patient, wherein the patient data includes at least one patient preference associated with the fluid injection, and wherein at least one piece of the patient data is used in a risk prediction for assessing a probability of the patient experiencing an adverse event during a fluid injection, and wherein the at least one adverse event includes the following adverse events: an extravasation, a post-contrast acute kidney injury, an acute adverse event, a contrast media induced nephrotoxicity, and a thyrotoxicosis such that the risk prediction includes a probability that the patient experiences the extravasation, a probability that the patient experiences the post-contrast acute kidney injury, a probability that the patient experiences the acute adverse event, a probability that the patient experiences the contrast media induced nephrotoxicity, and a probability that the patient experiences the thyrotoxicosis; and
at least one of a fluid injector and a medical imager, wherein parameters of at least one of an injection protocol of the fluid injection and an imaging protocol of the medical imager are adjusted based on the at least one piece of patient data.

13. A method comprising:
obtaining, with at least one processor, patient data associated with a patient;
determining, with the at least one processor, based on the patient data, an initial risk prediction for the patient associated with a fluid injection to be administered to the patient, wherein the initial risk prediction includes a probability that the patient experiences at least one adverse event in response to the fluid injection, and wherein the at least one adverse event includes: an extravasation, a post-contrast acute kidney injury, an acute adverse event, a contrast media induced nephrotoxicity, and a thyrotoxicosis such that the initial risk prediction includes a probability that the patient experiences the extravasation, a probability that the patient experiences the post-contrast acute kidney injury, a probability that the patient experiences the acute adverse event, a probability that the patient experiences the contrast media induced nephrotoxicity, and a probability that the patient experiences the thyrotoxicosis;
providing, with the at least one processor, to a user device, before the fluid injection is administered to the patient, the initial risk prediction;
determining, with at least one sensor, after the fluid injection is started, sensor data associated with the patient;
determining, with the at least one processor, based on the sensor data determined after the fluid injection is started, a current risk prediction for the patient associated with the fluid injection, wherein the current risk prediction includes a probability that the patient experiences the at least one adverse event in response to the fluid injection; and
providing, with the at least one processor, to the user device, the current risk prediction, wherein the initial risk prediction further includes at least one of: a prompt to administer a medication to the patient before the fluid injection, a prompt to adjust an injection protocol for the fluid injection, a prompt to adjust an imaging protocol for an imaging scan; a prompt to prepare the patient before the fluid injection, a prompt to observe and/or follow-up with the patient after the fluid injection, or any combination thereof.

14. The method of claim 13, wherein the patient data includes at least one of the following parameters associated with the patient: an age; a gender; a weight; a prior chemotherapy status; an estimated glomerular filtration rate (eGFR); a thyroid stimulating hormone (TSH) level; a Triiodothyronine (FT3) Thyroxine (FT4) ratio (FT3/FT4); a level of an environmental influence; a prior reaction to a previous fluid injection status; an atopic disorder status; a medical status associated with at least one of diabetes and hypertension; a congestive heart failure status; a hematocrit level; a renal failure status; a malignancy status; an implanted device for a central venous access status; a type of a medication; a type of fluid to be administered in the fluid injection; a type of the fluid injection; a type of an imaging exam; a flow rate associated with the fluid injection; a catheter gauge associated with the fluid injection; a total volume of fluid associated with the fluid injection; a pressure curve associated with the fluid injection, an injection site location associated with the fluid injection; or any combination thereof.

15. The method of claim 13, wherein the at least one adverse event includes at least one of: an extravasation, a post-contrast acute kidney injury, an acute adverse event, a contrast media induced nephrotoxicity, a thyrotoxicosis, or any combination thereof.

16. The method of claim 13, wherein the sensor data includes at least one of the following parameters associated with the patient: a heart rate; a sound or vibration; a temperature; an oxygen saturation level; an electrocardiogram (ECG); a body fat/water-content ratio; a tissue impedance; a vessel distribution level; a vessel diameter; a hydration level; a hematocrit level; a skin resistivity; a blood pressure; a muscle tension level; a light absorptivity level; a motion level; an arm position; an arm circumference; a respiration rate; an amount of absorbed radiation; an electromyogram (EMG); a skin color; a surface vessel dilation amount; a bio-impedance; a light absorptivity; a hemoglobin level; an inflammation level; an environmental temperature of an environment surrounding the patient, a barometric pressure in an environment surrounding the patient; an ambient light level; an ambient sound level; or any combination thereof.

17. The method of claim 13, further comprising:
determining, with the at least one sensor, during the fluid injection, the sensor data;
determining, with the at least one processor, based on the sensor data determined during the fluid injection, the current risk prediction for the patient associated with the fluid injection; and
providing, to the user device, during the fluid injection the current risk prediction.

18. The method of claim 13, further comprising:
determining, with the at least one sensor, after the fluid injection, the sensor data;
determining, with the at least one processor, based on the sensor data determined after the fluid injection, the current risk prediction for the patient associated with the fluid injection; and
providing, to the user device, after the fluid injection the current risk prediction.

19. The method of claim 13, wherein the at least one adverse event includes an extravasation, and wherein providing the current risk prediction further includes, in response to determining that the patient experiences the extravasation, automatically controlling, with the at least one processor, a fluid injection system to stop the fluid injection.

20. The method of claim 13, wherein the at least one sensor includes at least one of: an image capture device; an accelerometer; a strain gauge; a global positioning system (GPS); a skin resistivity or conductance sensor; a heart rate monitor; a microphone; a thermal or temperature sensor; a pulse oximeter; a hydration sensor; a dosimeter; an ultrasound sensor; an acoustic sensor; one or more electrodes configured to measure at least one of a tissue impedance, an electromyogram (EMG), and an electrocardiogram (ECG); a microwave sensor; a mechanical impedance sensor; a chemical sensor; a force or pressure sensor; or any combination thereof.

21. The method of claim 13, further comprising:
automatically controlling, with the at least one processor, based on the current risk prediction, at least one of: (i) a fluid injection system to stop the fluid injection; and (ii) an imaging system to adjust a timing of an imaging operation.

* * * * *